(12) United States Patent
Nishimura et al.

(10) Patent No.: US 11,298,372 B2
(45) Date of Patent: Apr. 12, 2022

(54) COMPOSITION FOR AMELIORATING LOSS OF HAIR AND GRAYING OF HAIR, AND USE THEREOF

(71) Applicant: National University Corporation Tokyo Medical and Dental University, Tokyo (JP)

(72) Inventors: Emi Nishimura, Tokyo (JP); Hiroyuki Matsumura, Tokyo (JP)

(73) Assignee: National University Corporation Tokyo Medical and Dental University, Tokyo (JP)

(*) Notice: Subject to any disclaimer, the term of this patent is extended or adjusted under 35 U.S.C. 154(b) by 0 days.

(21) Appl. No.: 16/885,930

(22) Filed: May 28, 2020

(65) Prior Publication Data

US 2020/0289541 A1 Sep. 17, 2020

Related U.S. Application Data

(63) Continuation of application No. 16/069,496, filed as application No. PCT/JP2017/000610 on Jan. 11, 2017, now Pat. No. 10,702,544.

(30) Foreign Application Priority Data

Jan. 12, 2016 (JP) .................. 2016-003424

(51) Int. Cl.
| | | |
|---|---|---|
| *A61K 31/713* | (2006.01) | |
| *A61K 38/55* | (2006.01) | |
| *A61K 36/05* | (2006.01) | |
| *A61K 36/14* | (2006.01) | |
| *A61K 36/47* | (2006.01) | |
| *A61K 36/48* | (2006.01) | |
| *A61K 36/54* | (2006.01) | |
| *A61K 8/97* | (2017.01) | |
| *A61K 31/506* | (2006.01) | |

(Continued)

(52) U.S. Cl.
CPC ............ *A61K 31/713* (2013.01); *A61K 8/97* (2013.01); *A61K 31/05* (2013.01); *A61K 31/16* (2013.01); *A61K 31/222* (2013.01); *A61K 31/355* (2013.01); *A61K 31/375* (2013.01); *A61K 31/381* (2013.01); *A61K 31/506* (2013.01); *A61K 31/7048* (2013.01); *A61K 31/7088* (2013.01); *A61K 36/04* (2013.01); *A61K 36/05* (2013.01); *A61K 36/14* (2013.01); *A61K 36/18* (2013.01); *A61K 36/185* (2013.01); *A61K 36/23* (2013.01); *A61K 36/28* (2013.01); *A61K 36/30* (2013.01); *A61K 36/424* (2013.01); *A61K 36/47* (2013.01); *A61K 36/48* (2013.01); *A61K 36/488* (2013.01); *A61K 36/489* (2013.01); *A61K 36/53* (2013.01); *A61K 36/54* (2013.01); *A61K 36/60* (2013.01); *A61K 36/718* (2013.01); *A61K 36/738* (2013.01); *A61K 36/74* (2013.01); *A61K 36/82* (2013.01); *A61K 38/55* (2013.01); *A61K 39/395* (2013.01); *A61K 45/00* (2013.01); *A61K 48/00* (2013.01); *A61P 17/14* (2018.01); *A61Q 5/00* (2013.01); *A61Q 7/00* (2013.01); *C12Q 1/37* (2013.01); *A61K 31/13* (2013.01); *A61K 36/00* (2013.01)

(58) Field of Classification Search
CPC .......................... A61K 31/713; A61P 17/14
See application file for complete search history.

(56) References Cited

U.S. PATENT DOCUMENTS

| | | | | |
|---|---|---|---|---|
| 6,013,279 A | * | 1/2000 | Klett-Loch | A61K 8/678 424/451 |
| 6,645,477 B1 | * | 11/2003 | Jarrousse | A61K 8/14 424/70.1 |

(Continued)

FOREIGN PATENT DOCUMENTS

| | | |
|---|---|---|
| CN | 1170034 | 1/1998 |
| CN | 105106932 | 12/2015 |

(Continued)

OTHER PUBLICATIONS

U.S. Appl. No. 16/069,496 , "Ex Parte Quayle Action", Dec. 26, 2019, 5 pages.

(Continued)

*Primary Examiner* — Kevin E Weddington
(74) *Attorney, Agent, or Firm* — Kilpatrick Townsend & Stockton LLP

(57) ABSTRACT

The present invention provides novel compositions for suppressing or improving hair loss, and compositions for suppressing or improving graying. More specifically, it provides agents that stabilize type XVII collagen expression, preferably agents that suppress the degradation of type XVII collagen by ELANE inhibitors and such, and compositions comprising a DNA repair-promoting agent or a DNA damage-suppressing agent as an active ingredient. Advantageous suppressive effects of hair loss and graying can be obtained when a composition comprising as an active ingredient a suppressive agent of type XVII collagen degradation such as an ELANE inhibitor is administered to a mammal. For the ELANE inhibitors, suppressive agents of type XVII collagen degradation and DNA repair-promoting agents, low-molecular compounds, polypeptides, proteins, antibodies, or nucleic acid medicine such as antisense oligos or siRNAs may be used. A method of screening for effective substances for suppression of hair loss and graying is also provided.

6 Claims, 45 Drawing Sheets

(51) Int. Cl.
  A61K 36/489    (2006.01)
  A61K 36/738    (2006.01)
  A61K 36/04     (2006.01)
  A61K 36/424    (2006.01)
  A61Q 5/00      (2006.01)
  A61K 48/00     (2006.01)
  A61K 31/7088   (2006.01)
  C12Q 1/37      (2006.01)
  A61K 36/30     (2006.01)
  A61K 36/74     (2006.01)
  A61K 36/23     (2006.01)
  A61K 36/60     (2006.01)
  A61K 36/185    (2006.01)
  A61Q 7/00      (2006.01)
  A61K 36/718    (2006.01)
  A61K 36/488    (2006.01)
  A61K 36/53     (2006.01)
  A61K 36/82     (2006.01)
  A61K 39/395    (2006.01)
  A61K 36/18     (2006.01)
  A61K 36/28     (2006.01)
  A61K 31/222    (2006.01)
  A61K 45/00     (2006.01)
  A61P 17/14     (2006.01)
  A61K 31/05     (2006.01)
  A61K 31/16     (2006.01)
  A61K 31/355    (2006.01)
  A61K 31/375    (2006.01)
  A61K 31/381    (2006.01)
  A61K 31/7048   (2006.01)
  A61K 31/13     (2006.01)
  A61K 36/00     (2006.01)

(56) References Cited

U.S. PATENT DOCUMENTS

| 10,702,544 B2 * | 7/2020 | Nishimura | A61K 36/28 |
| 2001/0048932 A1 | 12/2001 | Ahluwalia et al. | |
| 2004/0071647 A1 | 4/2004 | Jarrousse et al. | |
| 2005/0058611 A1 | 3/2005 | Fagot et al. | |
| 2007/0141175 A1 | 6/2007 | Gostine et al. | |
| 2014/0079686 A1 | 3/2014 | Barman et al. | |

FOREIGN PATENT DOCUMENTS

| EP | 1430933 | 6/2004 |
| JP | 62142108 | 6/1987 |
| JP | 2009161509 | 7/2009 |
| JP | 2011148792 | 8/2011 |
| JP | 2014231499 | 12/2014 |
| KR | 20040009776 | 1/2004 |
| KR | 20130115786 | 10/2013 |
| WO | 9962465 | 12/1999 |
| WO | 0166766 | 9/2001 |
| WO | 0234262 | 5/2002 |
| WO | 03103616 | 12/2003 |
| WO | 2008130130 | 10/2008 |
| WO | 2009016855 | 2/2009 |
| WO | 2010019450 | 2/2010 |
| WO | 2013031003 | 3/2013 |
| WO | 2014095289 | 6/2014 |
| WO | 2014178682 | 11/2014 |
| WO | 2015135927 | 9/2015 |

OTHER PUBLICATIONS

U.S. Appl. No. 16/069,496 , "Non-Final Office Action", dated Jul. 15, 2019, 9 pages.
U.S. Appl. No. 16/069,496 , "Notice of Allowance", dated Apr. 8, 2020, 6 pages.
Endo , "Sivelestat Sodium Hydrate", Pharma Medica, vol. 21, No. 1, 2003, pp. 124-125.
EP17738422.9 , "Extended European Search Report", dated Nov. 13, 2019, 20 pages.
EP17738422.9 , "Partial Supplementary European Search Report", dated Aug. 2, 2019, 22 pages.
Franzke et al., "Shedding of Collagen XVU/BP180 in Skin Depends on Both ADAM 1 0 and ADAM9", The Journal of Biological Chemistry, vol. 284, No. 35, Jun. 15, 2009, pp. 23386-23396.
Ishida et al., "Studies of the Active Substances in Herbs Used for Hair Treatment. H. Isolation of Hair R.egro,vth Substances,. Acetosyringone and Polyporusterone A and B, from Polyporus umbellatus Fries", Biological and Pharmaceutical Bulletin, vol. 22, No. 11, Jan. 29, 1999, pp. 1189-1192.
Jiang et al., "Rae/Rho Pathway Regulates Actin Depolymerization Induced by Aminoglycoside Antibiotics", Journal of neuroscience research, vol. 83, No. 8, Jun. 2006, pp. 1544-1551.
Labrousse et al., "The Metalloprotease-Directed Shedding of bp 180 (collagen xvii) From Human Keratinocytes In Culture Is Unaffected by Ceramide and Cell-Matrix Interaction", European Journal of Dermatology, vol. 12, No. 3, Jun. 2002, pp. 240-246.
Muijsers et al., "Apocynin Inhibits Peroxynitrite Formation by Murine Macrophages", British Journal of Pharmacology, vol. 130, No. 4, 2000, pp. 932-936.
Nishimura , Emi The Japanese Journal of Dermatology, vol. 121, No. 13, pp. 2643-2645, 2011.
PCT/JP2017/000610 , "International Preliminary Report on Patentability", dated Jul. 12, 2018, 18 pages.
PCT/JP2017/000610 , "International Search Report", dated Mar. 7, 2017, 10 pages.
PCT/JP2017/000610 , "Written Opinion", dated Mar. 7, 2017, 8 pages.
Seiberg , "Age Induced Hair Greying—the Multiple Effects of Oxidative Stress", International Journal of Cosmetic Science, vol. 35, No. 6, Jun. 14, 2013, pp. 532-538.
Sotiropoulou et al., "BCL-2 and Accelerated DNA Repair Mediates Resistance of Hair Follicle Bulge Stenl Cells to DNA-Damageinduced Cell Death", Nature Cell Biology, vol. 12, No. 6, 2010, pp. 572-582.
Stenn et al., "Controls of Hair Follicle Cycling", Physiological Reviews, vol. 81, No. 1, Jan. 2001, pp. 449-494.
Tanimura et al., "Hair Follicle Stem Cells Provide a Functional Niche for Melanocyte Stem Cells", Cell Stem Cell, vol. 8, Feb. 2011, pp. 177-187.
Umeki , "Effects of Non-Sterordal Antiinflammatory Drugs on Human Neutrophil Nadph Oxidase in Both Whole Cell And Cell-Free Systems", Biochemical Pharmacology, vol. 40, No. 3, Available Online at: :https://www.sciencedirect.com/science/article/pii/000629529090556Z/pdf?md5=24bbeb653768b97cf96e3b602de39943&pid=1-s2.0-000629529090556Z -main. pdf, Aug. 1, 1990, pp. 559-564.
Verraes et al., "Respective Contribution of Neutrophil Elastase and Matrix Metalloproteinase 9 in the Degradation of BP180 (Type XVII Collagen) in Human Bullous Pemphigoid", The Journal of Investigative Dermatology, vol. 117, No. 5, 2001, pp. 1091-1196.

* cited by examiner

COMPOSITION FOR AMELIORATING LOSS OF HAIR AND GRAYING OF HAIR, AND USE THEREOF

CROSS REFERENCE TO RELATED APPLICATIONS

The present application is a continuation of U.S. patent application Ser. No. 16/069,496, filed Jul. 11, 2018, which is a national-phase application under 35 U.S.C. 371 of International Application No. PCT/JP2017/000610 (filed Jan. 11, 2017), which is an application that claims the priority benefits of Japanese Patent Application No. 2016-003424 (filed Jan. 12, 2016). These applications are incorporated by reference in their entirety for all purposes.

TECHNICAL FIELD

The present invention relates to compositions for suppressing or improving hair loss, compositions for suppressing or improving graying, compositions for suppressing hair follicle miniaturization (shrinkage), compositions for treating or preventing alopecia, methods of screening for substances that suppress hair loss, graying or hair follicle miniaturization. More specifically, it relates to DNA repair-promoting agents, DNA damage-suppressing agents, and type XVII collagen expression-stabilizing agents, preferably suppressive compositions of hair loss, graying or hair follicle miniaturization which comprise a substance that suppresses type XVII collagen degradation or a substance that induces type XVII collagen expression, and a method of screening for hair loss suppressants (hair growth agents), graying suppressants, or suppressive agents of hair follicle miniaturization using the activity of suppressing type XVII collagen degradation as a reference.

BACKGROUND ART

With aging, functional or structural declines are seen in tissues and organs. Many different hypotheses have been proposed to understand aging at the tissue or individual level. Genes involved in aging phenotypes and/or individual longevity have been reported, yet the exact in vivo mechanism(s) underlying the progression of aging-associated changes at the tissue level is not sufficiently understood.

Intrinsic DNA damage that may be caused by errors in DNA replication, reactive oxygen species, telomere end problems, chromosomal abnormalities or such is known to accumulate in tissue-constituting cells, and they relate to tissue aging. Typical aging phenotypes such as graying and hair loss are known to be facilitated by not only intrinsic genome instability seen in premature aging syndromes, but also extrinsic genome instability caused by environmental factors such as radiation exposure.

Tissue atrophy due to genome instability has been explained with cellular senescence or cell death. However, typical senescent cells are not readily induced in skin tissues simply with genomic instability, but rather appear in papilloma and melanocytic nevi in the skin, and they are thought to relate to inhibition of carcinogenesis. Today, aging-associated changes in tissue stem cells (stem cell aging) are seen as one of the features of aging; however, the fate of aged tissue stem cells, influence of DNA damage on the fate, and also the role in the aging process of tissues and organs have not yet been made clear.

Hair follicle stem cells localize in the bulge region inside hair follicles, and they are responsible for hair regrowth at each hair cycle (Patent Document 1; Non-patent Document 1). It has been reported that mouse HFSCs generally do not display apparent decline, but in fact, the telogen phase becomes longer with age, and changes are seen in the cytokine signals in HFSCs, and their colony-forming ability is also reduced. On the other hand, mammals that live longer lose their hair and HFs with age.

Hair growth is generally classified into the growth phase (anagen), regressing phase (catagen) and resting phase (telogen) (Non-patent Document 2). In the case of human hair, after the growth phase continues for two to seven years, it goes through the regressing phase and resting phase, and then hair falls out.

The primary function of hair is protection from trauma or direct sunlight, prevention of loss of body temperature and such; and hair follicles also carry the role of reservoir for skin stem cells. Further, hair is also important in terms of mediating social communication, and decrease of hair volume may bring about reduction of quality of life in people.

Among alopecia, there are male pattern alopecia, female pattern alopecia, seborrheic alopecia, senile alopecia, alopecia areata, drug alopecia, scarring alopecia, postpartum alopecia occurring after childbirth, and such. Medicament alopecia and scarring alopecia include those iatrogenically induced by the side effects of cancer treatments with anti-cancer agents and X-ray radiation, respectively. However, ways of dealing with the alopecia have not been established as of now.

The major hair growing agents/hair tonics currently approved as pharmaceuticals include minoxidil and finasteride. Minoxidil is a pharmaceutical originally developed as an oral hypertensive drug that works mainly on blood vessel dilation. In patients receiving treatment of the hypertensive drug, vasodilation and hypertrichosis such as facilitation of hair root regeneration were observed; and thus, the pharmaceutical was newly developed as an external hair growth agent for medical use. Minoxidil promotes the production of cell growth factors (VEGF and such) from dermal papilla cells, and induces vasodilation by activating vascular smooth muscle ATP-sensitive K channels. This is known to transfer hair follicles from the resting phase to the initial growth phase, and has the effect of extending the growth phase and making the hair grow thick.

DHT (dihydrotestosterone) has the effect of inhibiting hair growth mainly in the frontal region and parietal region. Finasteride works by inhibiting type II 5-α reductase which is an enzyme that converts testosterone to DHT, and suppressing DHT synthesis. The pharmaceutical was developed by applying the drug for treatment of prostatic hypertrophy which is caused by male hormone as a therapeutic agent for androgenetic alopecia (AGA).

Despite that these pharmaceuticals are currently on the market, more effective medicaments are in demand for countermeasures against hair loss. Similarly, more effective medicaments are in demand for countermeasures against graying.

PRIOR ART DOCUMENTS

Patent Documents

[Patent Document 1] Japanese published unexamined patent application publication No.: 2009-161509

Non-Patent Documents

[Non-patent Document 1] Tanimura et al., Cell Stem Cell Vol. 8, February 2011, pp. 177-187

[Non-patent Document 2] K. S. Stenn and R. Paus, PHYSIOLOGICAL REVIEWS Vol. 81, No. 1, January 2001, pp. 449-494

SUMMARY OF THE INVENTION

Problems to be Solved by the Invention

One of the objectives of the present invention is to provide compositions for suppressing or improving hair loss, compositions for suppressing or improving graying, and compositions for suppressing hair follicle miniaturization. Further, another objective of the present invention is to provide a method of screening for substances that suppress or improve hair loss, graying or hair follicle miniaturization.

Means for Solving the Problems

The present inventors recognized accumulation of DNA damage in aged hair follicle stem cells in mice and humans, and reduction of type XVII collagen (COL17A1) expression in mouse hair follicle stem cells as a result of its degradation by X-ray radiation which is known to induce DNA damage; and generated a mouse deficient in COL17A1 specifically in hair follicle stem cells, and discovered that this can imitate aging-associated changes in the skin and hair follicles. Further, they elucidated that as a result of DNA damage response, neutrophil elastase (ELANE) induced in the keratinocytes of basal membrane which contains hair follicle stem cells is involved in the COL17A1 degradation caused by aging or X-ray radiation. It was confirmed that forcedly expressing COL17A1 in mouse hair follicles and basal cells of the epidermis suppresses aging-associated alterations in hair follicle stem cells so as to maintain stem cells, thereby postponing changes in the hair follicles and the whole skin. Based on the above, COL17A1 expressed by keratinocytes in the basal membrane such as hair follicle stem cells is thought to fight DNA damage accompanying aging or X-ray radiation and suppresses aging alterations in hair follicles and skin. It facilitates repair of DNA damage, suppresses DNA damage, and increases COL17A1 expression by suppressing its degradation to stably express COL17A1. This is thought to be helpful for the anti-aging of hair follicles and skin, suppression of hair loss and graying, and hair growth. The present invention is based on these findings, and specifically relates to the following:

[1] A composition for use in suppressing or improving hair loss, which comprises an agent that stabilizes type XVII collagen expression, preferably a suppressive agent of type XVII collagen degradation.
[2] A composition for use in suppressing or improving graying, which comprises an agent that stabilizes type XVII collagen expression, preferably a suppressive agent of type XVII collagen degradation.
[3] A composition for use in suppressing or improving hair follicle miniaturization, which comprises an agent that stabilizes type XVII collagen expression, preferably a suppressive agent of type XVII collagen degradation.
[4] A composition for use in treating or preventing alopecia, which comprises an agent that stabilizes type XVII collagen expression, preferably a suppressive agent of type XVII collagen degradation.
[5] The composition described in [4], wherein the alopecia is an alopecia in which hair progressively becomes thinner, and is in particular any alopecia selected from the group consisting of senile alopecia, male pattern alopecia, diffuse alopecia, female pattern alopecia, drug alopecia, and scarring alopecia.
[6] The composition described in any one of [1] to [5], wherein the suppressive agent of type XVII collagen degradation is an inhibitor of neutrophile elastase (ELANE).
[7] The composition described in [6], wherein the inhibitor of neutrophile elastase is selected from the group consisting of α1 antitrypsin (α1-AT), sivelestat sodium hydrate (Monosodium N-{2-[4-(2,2-dimethylpropanoyloxy)-phenylsulfonylamino]benzoyl}aminoacetate tetrahydrate; also called elaspol), ONO-6818 (2-(5-Amino-6-oxo-2-phenylhydropyrimidinyl)-N-[2-(5-tert-butyl-1,3,4-oxadiazol-2-yl)-1-(methylethyl)-2-oxoethyl]acetamide), Depelestat (Depelestat; also called EPI-hNE4 or DX-890).
[8] The composition described in [6], wherein the inhibitor of neutrophile elastase is a monoclonal antibody or a fragment thereof.
[9] The composition described in [6], wherein the inhibitor of neutrophile elastase is an antisense oligonucleotide.
[10] The composition described in [6], wherein the inhibitor of neutrophile elastase is an siRNA.
[11] The composition described in any one of [1] to [10], which is a pharmaceutical composition.
[12] The composition described in any one of [1] to [10], which is a cosmetic composition.
[13] The composition described in any one of [1] to [10], which is a beauty supplement.
[14] The composition described in any one of [1] to [13], which is an oral preparation.
[15] The composition described in any one of [1] to [13], which is an injectable preparation.
[16] The composition described in any one of [1] to [13], which is a dermatological preparation.
[17] A method for suppressing or improving hair loss in a mammal, which comprises administering to the mammal a suppressive agent of type XVII collagen degradation or stabilizing agent of type XVII collagen.
[18] A method for suppressing or improving graying in a mammal, which comprises administering to the mammal a suppressive agent of type XVII collagen degradation or stabilizing agent of type XVII collagen.
[19] A method for suppressing hair follicle miniaturization in a mammal, which comprises administering to the mammal a suppressive agent of type XVII collagen degradation or stabilizing agent of type XVII collagen.
[20] A method for treating or preventing alopecia in a mammal, which comprises administering to the mammal a suppressive agent of type XVII collagen degradation or stabilizing agent of type XVII collagen.
[21] The method described in [20], wherein the alopecia is an alopecia in which hair progressively becomes thinner, and is in particular any alopecia selected from the group consisting of senile alopecia, male pattern alopecia, diffuse alopecia, female pattern alopecia, drug alopecia, and scarring alopecia.
[22] A method for suppressing or improving hair loss in a mammal, which comprises administering to the mammal a suppressive agent of type XVII collagen degradation or stabilizing agent of type XVII collagen.
[23] A method for suppressing or improving graying in a mammal, which comprises suppressing type XVII collagen degradation.
[24] A method for suppressing hair follicle miniaturization in a mammal, which comprises suppressing type XVII collagen degradation.

[25] A method for treating or preventing alopecia in a mammal, which comprises suppressing type XVII collagen degradation.

[26] The method described in [25], wherein the alopecia is an alopecia in which hair progressively becomes thinner, and is in particular any alopecia selected from the group consisting of senile alopecia, male pattern alopecia, diffuse alopecia, female pattern alopecia, drug alopecia, and scarring alopecia.

[27] Use of a suppressive agent of type XVII collagen degradation in the manufacture of a medicament for suppressing or improving hair loss.

[28] Use of a suppressive agent of type XVII collagen degradation in the manufacture of a medicament for suppressing or improving graying.

[29] Use of a suppressive agent of type XVII collagen degradation in the manufacture of a medicament for suppressing hair follicle miniaturization.

[30] Use of a suppressive agent of type XVII collagen degradation in the manufacture of a medicament for treating or preventing alopecia.

[31] The use described in [30], wherein the alopecia is an alopecia in which hair progressively becomes thinner, and is in particular any alopecia selected from the group consisting of senile alopecia, male pattern alopecia, diffuse alopecia, female pattern alopecia, drug alopecia, and scarring alopecia.

[32] A method of screening for a substance effective for suppression or improvement of hair loss, suppression or improvement of graying, and/or suppression of hair follicle miniaturization, which comprises (i) contacting a test substance with neutrophil elastase in vitro, (ii) measuring the activity of neutrophil elastase (ELANE), and (iii) determining whether or not the test substance reduces the activity of neutrophil elastase (ELANE).

[33] A method of promoting hair loss, which comprises enhancing the activity of neutrophil elastase.

[34] A composition for use in suppressing or improving hair loss, which comprises an inhibitor of neutrophil elastase.

[35] A composition for use in suppressing or improving graying, which comprises an inhibitor of neutrophil elastase.

[36] A composition for use in suppressing hair follicle miniaturization, which comprises an inhibitor of neutrophil elastase.

[37] A composition for use in treating or preventing alopecia, which comprises an inhibitor of neutrophil elastase.

[38] The composition described in [37], wherein the alopecia is an alopecia in which hair progressively becomes thinner, and is in particular any alopecia selected from the group consisting of senile alopecia, male pattern alopecia, diffuse alopecia, female pattern alopecia, drug alopecia, and scarring alopecia.

[39] A pharmaceutical composition for use in treating or preventing alopecia in which hair progressively becomes thinner, in particular, any alopecia selected from the group consisting of senile alopecia, male pattern alopecia, diffuse alopecia, female pattern alopecia, drug alopecia, and scarring alopecia, which comprises the type XVII collagen protein or a nucleic acid encoding thereof, or an agent that stabilizes or stably expresses type XVII collagen.

[40] A method for treating or preventing alopecia in which hair progressively becomes thinner, in particular, any alopecia selected from the group consisting of senile alopecia, male pattern alopecia, diffuse alopecia, female pattern alopecia, drug alopecia, and scarring alopecia, which comprises the type XVII collagen protein or a nucleic acid encoding thereof, or an agent that stabilizes or stably expresses type XVII collagen.

[41] A pharmaceutical composition for use in treating or preventing alopecia that undergoes the process of progressive hair thinning (hair follicles miniaturization) (senile alopecia, male pattern alopecia, diffuse alopecia, female pattern alopecia, drug alopecia, scarring alopecia and such), which comprises (i) a compound or nucleic acid that increases or stabilizes the expression of type XVII collagen (COL17A1) in hair follicle stem cells or keratinocytes, or (ii) a compound or nucleic acid that increases type XVII collagen-expressing cells.

[42] A method of screening for a compound useful for treatment or prevention of alopecia in which hair progressively becomes thinner, in particular, any alopecia selected from the group consisting of senile alopecia, male pattern alopecia, diffuse alopecia, female pattern alopecia, drug alopecia, and scarring alopecia, and/or suppression of graying, which comprises (i) contacting the compound with hair follicle stem cells or keratinocytes in vitro, (ii) investigating change in the amount of type XVII collagen expression in the hair follicle stem cells or keratinocytes, and (iii) identifying the compound that increases or stabilizes the amount of type XVII collagen expression in the hair follicle stem cells or keratinocytes.

[43] A composition for use in suppressing or improving hair loss, which comprises a DNA damage repair-promoting agent or a DNA damage-suppressing agent.

[44] A composition for use in suppressing or improving graying, which comprises a DNA damage repair-promoting agent or a DNA damage-suppressing agent.

[45] A composition for use in suppressing hair follicle miniaturization, which comprises a DNA damage repair-promoting agent or a DNA damage-suppressing agent.

[46] A composition for use in treating or preventing alopecia, which comprises a DNA damage repair-promoting agent or a DNA damage-suppressing agent.

[47] The composition described in [46], wherein the alopecia is an alopecia in which hair progressively becomes thinner, and is in particular any alopecia selected from the group consisting of senile alopecia, male pattern alopecia, diffuse alopecia, female pattern alopecia, drug alopecia, and scarring alopecia.

[48] The composition described in any one of [43] to [47], wherein the DNA damage repair-promoting agent or DNA damage-suppressing agent is one, two or more types of extracts selected from the group consisting of *Gigartina tenella* extract, *Sarcandra glabra* extract, *Saraca dives* extract, *Cudrania pubescens* extract, *Taxodium distichum* extract, *Ludwigia octovalis* extract, *Deutzianthus tonkinensis* extract, *Alchornea trewioides* extract, *Berchemia polyphylla* extract, *Glochidion puberum* extract, *Sassafras tzumu* extract, *Cinchona* extract, comfrey extract, *Coffea* extract, *Pueraria* root extract, burdock extract, *Coptis* root extract, *Sophora angustifolia* extract, *Chlorella vulgaris* extract, *Lavandula vera* extract, *Oenothera biennis* extract, rose extract, *Gynostemma* extract, *Rabdosia japonica* extract, *Lamium album* extract, carrot extract, Japanese linden extract, *Sanguisorba officinalis, Lotus* extract, *Tea* extract, and okra extract.

[49] A method for suppressing or improving hair loss in a mammal, which comprises promoting repair of DNA damage or suppressing DNA damage, preferably administering to the mammal a DNA damage repair-promoting agent or a DNA damage-suppressing agent.

[50] A method for suppressing or improving graying in a mammal, which comprises promoting repair of DNA damage or suppressing DNA damage, preferably administering to the mammal a DNA damage repair-promoting agent or a DNA damage-suppressing agent.

[51] A method for suppressing hair follicle miniaturization in a mammal, which comprises promoting repair of DNA damage or suppressing DNA damage, preferably administering to the mammal a DNA damage repair-promoting agent or a DNA damage-suppressing agent.

[52] A method for treating or preventing alopecia in a mammal, which comprises promoting repair of DNA damage or suppressing DNA damage, preferably administering to the mammal a DNA damage repair-promoting agent or a DNA damage-suppressing agent.

[53] Use of a DNA damage repair-promoting agent or DNA damage-suppressing agent in the manufacture of a medicament for suppressing or improving hair loss.

[54] Use of a DNA damage repair-promoting agent or DNA damage-suppressing agent in the manufacture of a medicament for suppressing or improving graying.

[55] Use of a DNA damage repair-promoting agent or DNA damage-suppressing agent in the manufacture of a medicament for suppressing hair follicle miniaturization.

[56] Use of a DNA damage repair-promoting agent or DNA damage-suppressing agent in the manufacture of a medicament for treating or preventing alopecia.

[57] A method of screening for a compound useful for treatment or prevention of alopecia in which hair progressively becomes thinner, in particular, any alopecia selected from the group consisting of senile alopecia, male pattern alopecia, diffuse alopecia, female pattern alopecia, drug alopecia, and scarring alopecia, and/or suppression of graying, which comprises (i) contacting the compound with hair follicle cells or keratinocytes in vitro, (ii) investigating change in the DNA damage-repairing ability in the hair follicle stem cells or keratinocytes, and (iii) identifying the compound that increases the DNA damage-repairing ability in the hair follicle stem cells or keratinocytes.

[58] A composition for use in suppressing or improving hair loss, which comprises an MMP inhibitor.

[59] A composition for use in suppressing or improving graying, which comprises an MMP inhibitor.

[60] A composition for use in suppressing hair follicle miniaturization, which comprises an MMP inhibitor.

[61] A composition for use in treating or preventing alopecia, which comprises an MMP inhibitor.

[62] The composition described in [61], wherein the alopecia is any alopecia selected from the group consisting of senile alopecia, male pattern alopecia, diffuse alopecia, female pattern alopecia, drug alopecia, and scarring alopecia.

[63] The composition described in any of [58] to [62], wherein the MMP inhibitor is a compound selected from the group consisting of Marimastat, Batimastat, PD166793, Ro32-3555, WAY170523, UK370106, TIMP1, TIMP2, TIMP3 and TIMP4.

[64] A composition for use in suppressing or improving hair loss, which comprises an NADPH oxidase inhibitor.

[65] A composition for use in suppressing or improving graying, which comprises an NADPH oxidase inhibitor.

[66] A composition for use in suppressing hair follicle miniaturization, which comprises an NADPH oxidase inhibitor.

[67] A composition for use in treating or preventing alopecia, which comprises an NADPH oxidase inhibitor.

[68] The composition described in [67], wherein the alopecia is any alopecia selected from the group consisting of senile alopecia, male pattern alopecia, diffuse alopecia, female pattern alopecia, drug alopecia, and scarring alopecia.

[69] The composition described in any one of [64] to [68], wherein the NADPH oxidase inhibitor is a compound selected from the group consisting of apocynin, AEBSF, GK-136901, ML171, VAS2870 and VAS3947.

[70] A composition for use in suppressing or improving hair loss, which comprises an oxidation inhibitor.

[71] A composition for use in suppressing or improving graying, which comprises an oxidation inhibitor.

[72] A composition for use in suppressing hair follicle miniaturization, which comprises an oxidation inhibitor.

[73] A composition for use in treating or preventing alopecia, which comprises an oxidation inhibitor.

[74] The composition described in [73], wherein the alopecia is any alopecia selected from the group consisting of senile alopecia, male pattern alopecia, diffuse alopecia, female pattern alopecia, drug alopecia, and scarring alopecia.

[75] The composition described in any one of [70] to [74], wherein the oxidation inhibitor is a compound selected from the group consisting of ascorbic acid, edaravone, α-tocopherol, glutathione, catechin, and resveratrol.

[76] A composition for use in suppressing or improving hair loss, which comprises an ADAM inhibitor.

[77] A composition for use in suppressing or improving graying, which comprises an ADAM inhibitor.

[78] A composition for use in suppressing hair follicle miniaturization, which comprises an ADAM inhibitor.

[79] A composition for use in treating or preventing alopecia, which comprises an ADAM inhibitor.

[80] The composition described in [79], wherein the alopecia is any alopecia selected from the group consisting of senile alopecia, male pattern alopecia, diffuse alopecia, female pattern alopecia, drug alopecia, and scarring alopecia.

[81] The composition described in any one of [76] to [80], wherein the ADAM inhibitor is a compound selected from the group consisting of TAPI-2, Secophenol, GI254023X, Erythrolosamine, TIMP1, TIMP2, TIMP3 and TIMP4.

MODE FOR CARRYING OUT THE INVENTION

Figure 1A:
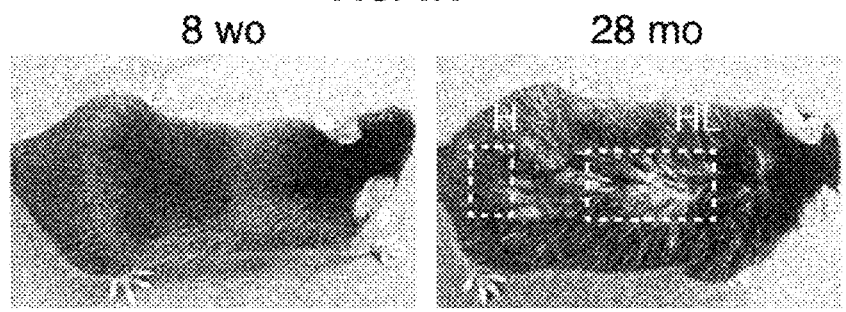
FIG. 1A Representative photos of young mice (8 weeks of age) and aged mice (28 months of age) are shown.

The present invention is explained in detail below. The present inventors discovered that the expression of type XVII collagen (Col17A1) is reduced in aged hair follicle stem cells in mice and humans, and that the reduction of its expression in mouse hair follicle stem cells is caused by Col17A1 degradation as a result of irradiation. Further, it has been made clear that neutrophil elastase (ELANE) is involved in Col17A1 degradation. By forcedly expressing COL17A1 in hair follicles and basal cells of the epidermis, change of hair follicle stem cells due to aging is suppressed and stem cells are maintained, and delay of change in the hair follicles and the whole skin is confirmed. Based on the above, COL17A1 expressed by hair follicle stem cells is thought to suppress aging-associated changes in hair follicles and skin accompanied by aging and irradiation; and for example, it should be understandable to skilled artisans that suppression of its degradation using an inhibitor of neutrophil elastase is anti-aging for the skin and hair follicles, and is effective for the suppression or improvement of graying and suppression or improvement of hair loss (hair growth). Here, "suppression of hair loss or graying" used in the present specification is understood to include termination or delay of the progression of hair loss or graying. Further, "improvement of hair loss or graying" is understood to include reversing the progression of hair loss or graying, i.e., promotion of hair increase or hair turning black.

Hair Loss-Suppressing Compositions

One of the embodiments of the present invention relates to a composition for use in suppressing or improving hair loss, which comprises an agent that stabilizes type XVII collagen expression, preferably an agent that suppresses type XVII collagen degradation. As described above, the inventors discovered that due to COL17A1 degradation, hair follicle stem cells lose their stem cell signature and induce epidermal differentiation in the niche, and they undergo terminal differentiation to keratinocytes and are released from the skin surface; and as a result, this causes gradual hair follicle miniaturization or hair loss. Thus, it is understood by skilled artisans that hair loss (hair thinning) can be suppressed or improved by suppressing the reduction of type XVII collagen using a suppressive agent of type XVII collagen degradation (for example, an ELANE inhibitor). An example of the suppressive agent of type XVII collagen degradation is an inhibitor of neutrophil elastase (ELANE) which fragments type XVII collagen. That is, one of the embodiments of the present invention includes a composition for use in suppressing or improving hair loss, which comprises an inhibitor of neutrophil elastase. The stabilizing agent of type XVII collagen expression, suppressive agent of type XVII collagen degradation or inhibitor of neutrophil elastase can be, for example, a low-molecular compound, or a macromolecule such as a polypeptide, a protein, an antibody or a nucleic acid.

Graying-Suppressing Compositions

One of the embodiments of the present invention relates to a composition for use in suppressing or improving graying, which comprises an agent that stabilizes type XVII collagen expression, preferably an agent that suppresses type XVII collagen degradation. It is known that type XVII collagen is required for the maintenance of melanocyte stem cells (MSC) (Non-patent Document 1). Thus, a skilled artisan would understand that suppressing the reduction of type XVII collagen by using a suppressive agent of type XVII collagen degradation (for example, an ELANE inhibitor) can suppress or improve graying. An example of the suppressive agent of type XVII collagen degradation is an inhibitor of neutrophil elastase (ELANE) which fragments type XVII collagen. That is, one of the embodiments of the present invention includes a composition for use in suppressing or improving graying, which comprises an inhibitor of neutrophil elastase. The stabilizing agent of type XVII collagen expression, suppressive agent of type XVII collagen degradation or inhibitor of neutrophil elastase can be, for example, a low-molecular compound, or a macromolecule such as a polypeptide, a protein, an antibody or a nucleic acid.

Hair Follicle Miniaturization-Suppressing Compositions

Figure 7A:
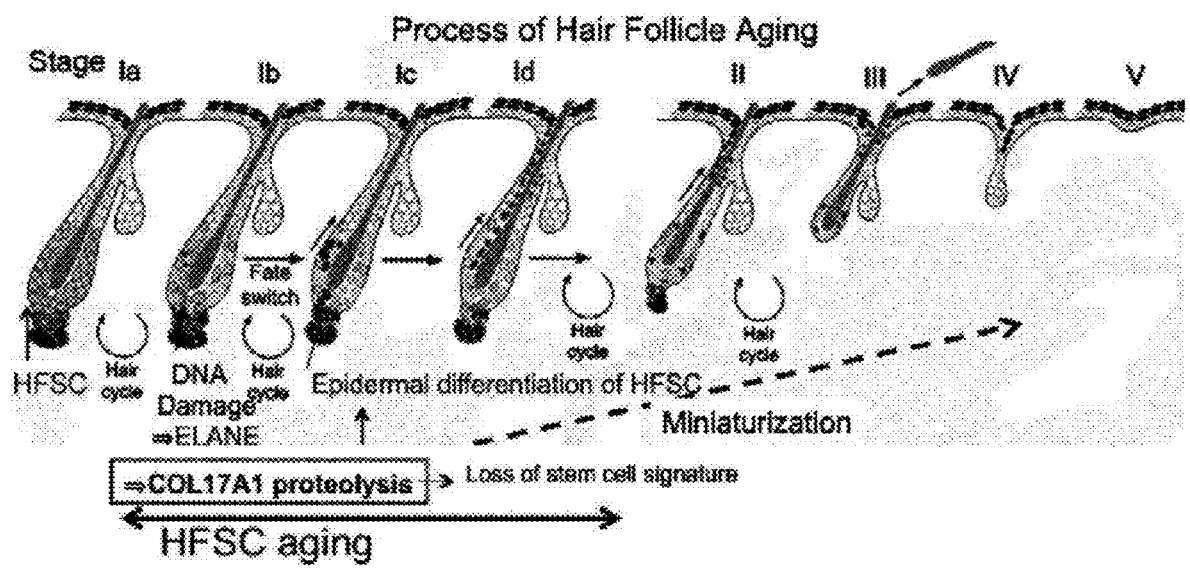
FIG. 7A It is a schematic diagram for the mechanism of hair follicle aging.
Figure 7B:
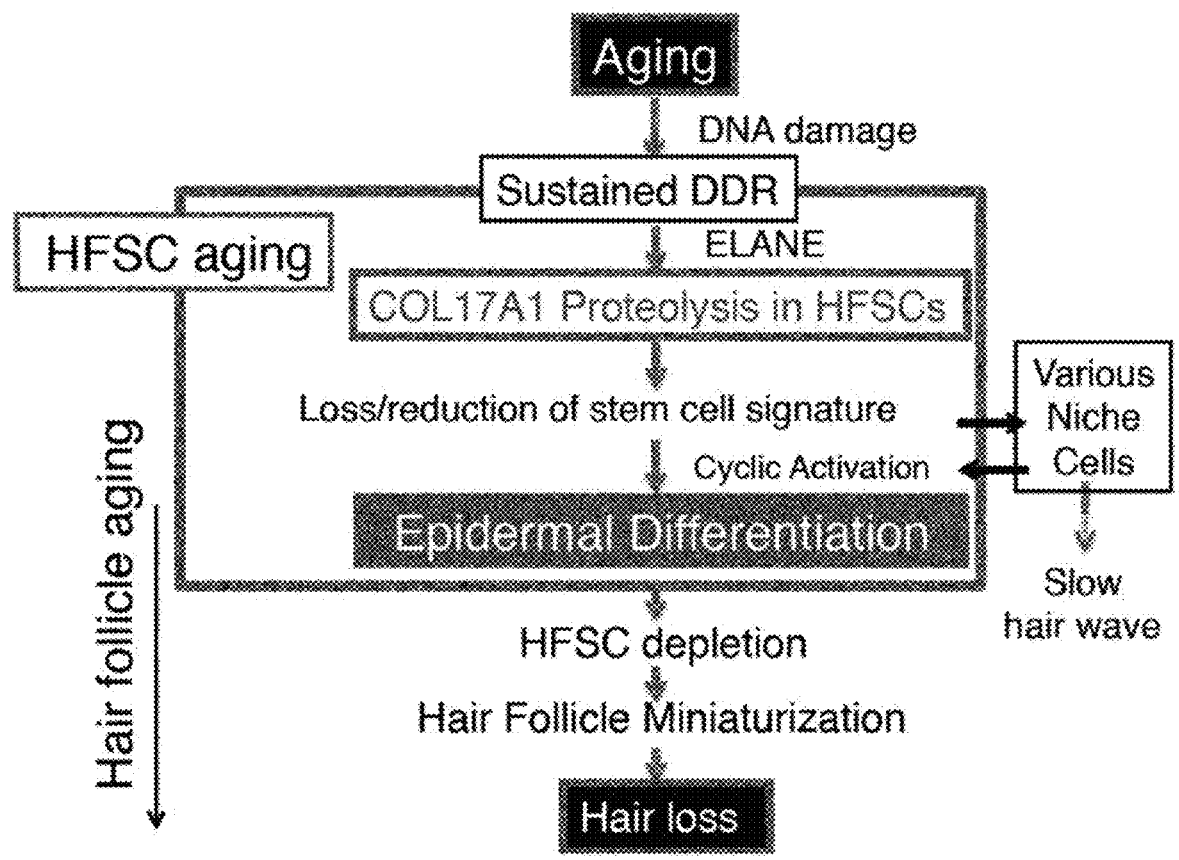
FIG. 7B It is a schematic diagram for the mechanism of hair follicle aging.

One of the embodiments of the present invention relates to a composition for use in suppressing hair follicle miniaturization, which comprises an agent that stabilizes type XVII collagen expression, preferably an agent that suppresses type XVII collagen degradation. "Miniaturized hair follicles" refers to hair follicles that have become smaller because the anagen phase of hair in the hair cycle is shortened. FIGS. 7A and 7B show the schematic diagram of hair follicle aging. The pool of hair follicle stem cells maintains the telogen state with increasing age (Stage Ia). Hair follicle stem cells showing a DNA damage response induce COL17A1 degradation through induction of the ELANE protease expression (Stage Ib). These hair follicle stem cells which have a weakly positive COL17A1 expression lose their stem cell signature and induce epidermal differentiation in the niche. These "aged" hair follicle stem cells move towards the epidermis through hair follicle junctions with hair cycling. These undergo terminal differentiation to keratinocytes and are released from the skin surface, causing gradual hair follicle miniaturization, hair thinning or hair loss. Thus, it is understood by skilled artisans that hair follicle miniaturization can be suppressed by suppressing the reduction of type XVII collagen using a suppressive agent of type XVII collagen degradation (for example, an ELANE inhibitor). An example of the suppressive agent of type XVII collagen degradation is an inhibitor of neutrophil elastase (ELANE) which fragments type XVII collagen. That is, one of the embodiments of the present invention includes a composition for use in suppressing hair follicle miniaturization, which comprises an inhibitor of neutrophil elastase. The stabilizing agent of type XVII collagen expression, suppressive agent of type XVII collagen degradation or inhibitor of neutrophil elastase can be, for example, a low-molecular compound, or a macromolecule such as a polypeptide, a protein, an antibody or a nucleic acid.

Compositions for Treatment/Prevention of Alopecia

One of the embodiments of the present invention relates to a composition for use in treating or preventing alopecia, which comprises an agent that stabilizes type XVII collagen expression, preferably an agent that suppresses type XVII collagen degradation. The target alopecia may be male pattern alopecia, seborrheic alopecia, senile alopecia, alopecia areata, drug alopecia caused by administration of an anti-cancer agent or such, scarring alopecia, postpartum alopecia occurring after childbirth, and mental-disorder alopecia; and among them, it can be in particular any one selected from the group of alopecia in which hair progressively becomes thinner, specifically senile alopecia, male pattern alopecia, diffuse alopecia, female pattern alopecia, drug alopecia, and scarring alopecia, without being limited thereto. An example of the suppressive agent of type XVII collagen degradation is an inhibitor of neutrophil elastase (ELANE) which fragments type XVII collagen. That is, one of the embodiments of the present invention includes a composition for use in treating or preventing alopecia, which comprises an inhibitor of neutrophil elastase. The stabilizing agent of type XVII collagen expression, suppressive agent of type XVII collagen degradation or inhibitor of neutrophil elastase can be, for example, a low-molecular compound, or a macromolecule such as a polypeptide, a protein, an antibody or a nucleic acid.

Suppressive Agents of Type XVII Collagen Degradation

Type XVII collagen (COL17A1/BP180/BPAG2) is a transmembrane-protein cell adhesion molecule, and is a hemidesmosome protein which is one of the cell adhesions in the epithelial tissue. The inventors discovered that type XVII collagen in hair follicle bulges is degraded by neutrophil elastase (ELANE) inhibitor. Thus, an ELANE inhibitor can be used as a suppressive agent of type XVII collagen degradation. It is understood by skilled artisans that inhibitors of other enzymes that degrade type XVII collagen may be similarly used as an ELANE inhibitor.

Neutrophil Elastase (ELANE) Inhibitors

Neutrophil elastase (ELANE, EC3.4.21.37) is a neutral protease with a molecular weight of about 30,000, and is present in azurophil granules (lysosomes). Neutrophil elastase (ELANE) inhibitors may be ones that inhibit the activity of ELANE or ones that suppress its expression. Further, the ELANE inhibitors may be selective ELANE inhibitors or non-selective ELANE inhibitors. The ELANE inhibitor can be, for example, a low-molecular compound, or a macromolecule such as a polypeptide, a protein, an antibody or a nucleic acid.

Low-Molecular Inhibitors

As low-molecular compounds that inhibit ELANE, for example, sivelestat sodium hydrate (Monosodium N-{2-[4-(2,2-dimethylpropanoyloxy)-phenylsulfonylamino] benzoyl}aminoacetate tetrahydrate; also called Elaspol), and ONO-6818 (2-(5-Amino-6-oxo-2-phenylhydropyrimidinyl)-N-[2-(5-tert-butyl-1,3,4-oxadiazol-2-yl)-1-(methylethyl)-2-oxoethyl]acetamide) are known. These inhibitory low-molecular compounds of neutrophil elastase can be used in the form of a pharmaceutically acceptable salt or derivative.

Polypeptide/Protein Inhibitors

As a polypeptide or protein that inhibits ELANE, for example, α1-antitrypsin (α1-AT; A1AT) is known. α1-antitrypsin is a glycoprotein consisted of 394 amino acids with a molecular weight of 51,000, and inhibits the function of elastase by binding to the active site of elastase or trypsin in a nearly irreversible manner. The sequence of α1-antitrypsin is public knowledge, and an α1-antitrypsin variant with the introduction of one or more mutations may be used as an ELANE inhibitor.

For another ELANE-inhibiting polypeptide, Depelestat (also called EPI-hNE4 or DX-890) is known. Depelestat is a powerful and selective small-protein ELANE inhibitor identified by the phage display method. It is understood by skilled artisans that other artificial ELANE inhibitors identified by the phage display method or such may be similarly used. Further, as an inhibitor from natural source, an inhibitor of elastase activity containing a fermented product of Japanese basil leaf (Japanese published unexamined patent application publication No.: 2006-61091), a fermented product of parsley (Japanese published unexamined patent application publication No.: 2006-75085), or a fermented product of bell pepper (Japanese published unexamined patent application publication No.: 2006-76926) may be used.

Antibodies

The ELANE inhibitor may be an anti-ELANE antibody. For the anti-ELANE antibody, a polyclonal antibody or monoclonal antibody can be used, and it is preferable to use a monoclonal antibody. As long as it is an antibody that has an inhibitory activity towards ELANE, it does not have to be full-length, and an antibody fragment can also be used. The mammalian animal from which the antibody is derived is not particularly limited, and a human antibody, mouse antibody, rat antibody, rabbit antibody, goat antibody or such can be used. When it is used for human, any of a human antibody, humanized antibody and chimera antibody can be used, and it is preferred that it is a human antibody. Further, the antibody or antibody fragment may comprise a peptide sequence identified by screening using a phage display method or such.

Antisense Oligonucleotides

The ELANE inhibitor may be an anti-ELANE antisense oligonucleotide. As the antisense oligonucleotide, for example, an oligonucleotide of 10-50 bases can be designed based on the nucleotide sequence of the ELANE gene. The antisense oligonucleotide may contain RNA, DNA or another modified nucleic acid. The antisense oligonucleotide may be completely complementary to the target sequence, or it may contain one or more mismatches. The nucleotide sequence of the ELANE gene is already known, and for example, it can be retrieved from a database such as GenBank:

ELANE elastase, neutrophil expressed [*Homo sapiens* (human)]
Gene ID: 1991
mRNA: NM_001972.2
Elane elastase, neutrophil expressed [*Mus musculus* (house mouse)]
Gene ID: 50701
mRNA: NM_015779.2 siRNAs

The ELANE inhibitor may be an siRNA targeting ELANE. The nucleotide sequence of the ELANE gene is already known, and for example, it can be retrieved from a database such as GenBank. The siRNA design method is already known to skilled artisans.

Stabilizing Agents of Type XVII Collagen Expression

In the context of the present specification, an agent that stabilizes type XVII collagen expression includes an inducer of type XVII collagen expression. The inventors discovered that MMP inhibitors, NADPH oxidase inhibitors, oxidation inhibitors, and ADAM inhibitors increase type XVII collagen expression. Therefore, in the compositions and methods of the present invention, an MMP inhibitor, an NADPH oxidase inhibitor, an oxidation inhibitor and/or an ADAM inhibitor can be used as an active ingredient. Accordingly, the embodiments of the present invention include compositions for use in suppressing or improving hair loss, compositions for use in suppressing or improving graying, compositions for use in suppressing hair follicle miniaturization, and compositions for use in treating or preventing alopecia, which comprise an MMP inhibitor, a NADPH oxidase inhibitor, an oxidation inhibitor and/or an ADAM inhibitor.

An MMP inhibitor is, for example, Marimastat, Batimastat, PD166793, Ro32-3555, WAY170523, UK370106, TIMP1, TIMP2, TIMP3, TIMP4 or such, without being limited thereto. An NADPH oxidase inhibitor is, for example, apocynin, AEBSF, GK-136901, ML171, VAS2870, VAS3947 or such, without being limited thereto. An oxidation inhibitor is, for example, ascorbic acid, edaravone, α-tocopherol, glutathione, catechin, resveratrol or such, without being limited thereto. An ADAM inhibitor is, for example, TAPI-2, Secophenol, GI254023X, Erythrolosamine, TIMP1, TIMP2, TIMP3, TIMP4 or such, without being limited thereto.

Pharmaceutical Compositions

One of the embodiments of the present invention relates to pharmaceutical compositions characterized in comprising an agent that stabilizes type XVII collagen expression, preferably an agent that suppresses type XVII collagen degradation, more specifically an ELANE inhibitor or an agent that promotes DNA damage repair or an agent that suppresses DNA damage as an active ingredient. In other words, one of the embodiments of the present invention relates to use of an agent that stabilizes type XVII collagen expression, preferably an agent that suppresses type XVII collagen degradation, more specifically use of an ELANE inhibitor or use of an agent that promotes DNA damage repair or an agent that suppresses DNA damage in the manufacturing of a medicament. For the ELANE inhibitor that serves as an active ingredient, for example, a low-molecular compound, polypeptide, protein, antibody, antisense oligonucleotide, siRNA or such as the ones described above can be used. The pharmaceutical compositions of the present invention can be made in any arbitrary form such as tablet, powder, liquid and semi-solid, and can contain an appropriate excipient or additive in addition to the ELANE inhibitor. The pharmaceutical compositions of the present invention may be combined with another active ingredient such as minoxidil, finasteride or such. The blending quantity of each ingredient can be appropriately determined within the acceptable range for pharmaceuticals. Further, the amount of the composition to be administered can be appropriately determined according to the type of medicinal agent to be used and the subject to be administered with. Also with respect to the route of administration, it can be appropriately determined depending on the type of medicinal agent to be used and the subject to be administered with.

The pharmaceutical compositions of the present invention can be used to treat or prevent alopecia or hair thinning. The type of alopecia is an alopecia in which hair progressively becomes thinner, specifically senile alopecia, male pattern alopecia, diffuse alopecia, female pattern alopecia, drug alopecia, and scarring alopecia, without being limited thereto.

Compositions for Cosmetic Purposes

One of the embodiments of the present invention relates to cosmetic compositions characterized in comprising an agent that stabilizes type XVII collagen expression, preferably an agent that suppresses type XVII collagen degradation, more specifically an ELANE inhibitor or an agent that promotes DNA damage repair or an agent that suppresses DNA damage as an active ingredient. In other words, one of the embodiments of the present invention relates to use of an agent that stabilizes type XVII collagen expression, preferably an agent that suppresses type XVII collagen degradation, more specifically use of an ELANE inhibitor or use of an agent that promotes DNA damage repair or an agent that suppresses DNA damage in the manufacturing of a medicament. For the ELANE inhibitor that serves as an active ingredient, for example, a low-molecular compound, polypeptide, protein, antibody, antisense oligonucleotide, siRNA or such as the ones described above can be used. The cosmetic compositions of the present invention can be made in any arbitrary form such as liquid, emulsion, gel, and cream. The content of the medicinal agent can be appropriately determined according to the type of medicinal agent to be used and the subject to be applied with.

Beauty Supplements

One of the embodiments of the present invention relates to beauty supplements characterized in comprising an agent that stabilizes type XVII collagen expression, preferably an agent that suppresses type XVII collagen degradation, more specifically an ELANE inhibitor or an agent that promotes DNA damage repair or an agent that suppresses DNA damage as an active ingredient. In other words, one of the embodiments of the present invention relates to use of an agent that stabilizes type XVII collagen expression, preferably an agent that suppresses type XVII collagen degradation, more specifically use of an ELANE inhibitor or use of an agent that promotes DNA damage repair or an agent that suppresses DNA damage in the manufacturing of a medicament. For the ELANE inhibitor that serves as an active ingredient, for example, a low-molecular compound, polypeptide, protein, antibody, antisense oligonucleotide, siRNA or such as the ones described above can be used. The cosmetic compositions of the present invention can be made in any arbitrary form such as tablet, powder and liquid. The beauty supplements of the present invention may be prepared to be, for example, ingested orally one to three times a day, before, during or after meals.

Methods for Suppressing Hair Loss, Methods for Suppressing Graying, and Such

One of the embodiments of the present invention relates to methods for suppressing or improving hair loss, graying or hair follicle miniaturization in a mammal. Such methods may include suppressing type XVII collagen degradation, more specifically, for example, administering a suppressive agent of type XVII collagen degradation such as an ELANE inhibitor to the mammal. Alternatively, such methods may include stabilizing (increasing) the expression of type XVII collagen, more specifically, for example, administering an MMP inhibitor such as Marimastat, an NADPH oxidase inhibitor such as apocynin and/or an oxidation inhibitor such as ascorbic acid to the mammal. The mammal includes, for example, human, monkey, mouse, rat, rabbit, sheep, goat, *Lama*, horse, mink, *fox*, stoat, raccoon, *Chinchilla, Sea* otter, otter, beaver, and seal. The amount to be administered can be appropriately determined according to the type of medicinal agent to be used and the subject to be administered with. With respect to the route of administration, it can also be appropriately determined according to the type of medicinal agent to be used and the subject to be administered with. A preferred route of administration is, for example, application or spraying of a liquid preparation, lotion preparation or cream preparation to the area of hair loss, subcutaneous injection of a liquid preparation, or oral administration of a solid preparation or liquid preparation. A patch containing the medicinal agent may be prepared and applied to the skin.

Screening Methods

One of the embodiments of the present invention relates to a method of screening for substances effective for suppression or improvement of hair loss, suppression or improvement of graying, and/or suppression of hair follicle miniaturization. Such screening method may include the following steps of i to iii:

(i) contacting a test substance with neutrophil elastase in vitro, (ii) measuring the activity of neutrophil elastase activity, and (iii) determining whether or not the test substance reduces the neutrophil elastase activity.

Measurement of the neutrophil elastase activity can be carried out using any arbitrary method known to skilled artisans. Substances identified by the above screening method are useful as ingredients of the compositions of the present invention for use in suppression or improvement of hair loss, suppression or improvement of graying, and/or suppression of hair follicle miniaturization. Further, in the methods of the present invention for suppressing or improving hair loss, suppressing or improving graying, and/or suppressing hair follicle miniaturization in a mammal, they are also useful as substances to be administered to the mammal.

Hair Loss-Promoting Methods

One of the embodiments of the present invention relates to a method of promoting hair loss, which comprises enhancing the activity of neutrophil elastase. Such method comprises administering a composition that enhances the neutrophil elastase activity or neutrophil elastase itself (nucleic acid or protein). Another embodiment of the present invention includes hair loss-promoting compositions comprising a substance that enhances the expression or activity of neutrophil elastase.

Compositions and Methods for Treating/Preventing Alopecia in which Hair Progressively Becomes Thinner Compared to male pattern alopecia, female pattern alopecia and senile alopecia, alopecia with a strong pattern signature is seen in relatively younger age. However, it is known that it subsequently becomes diffuse with age and is hardly distinguished from senile alopecia, and many cases of complications are seen. Not only in the case of classical senile alopecia, but when any of male pattern alopecia, female pattern alopecia, alopecia areata reaches the chronic stage, hair changes seen when hair follicles have miniaturized are shown, such as progressive thinning of the remaining hair and significant hair loss. While there are various factors ad causes, they are surmised to reflect hair follicle changes based on the depletion of hair follicle stem cells called hair follicle miniaturization. Thus, in addition to the treatment methods for the underlying causes in any of the treatments, it is thought that in cases that are inclined to become chronic, it is effective to use in combination an agent that suppresses hair follicle miniaturization itself in addition to the corresponding medicinal agent for the respective alopecia. For example, in male pattern alopecia, there are cases of insufficient response if only male hormone-dependent hair loss is suppressed by suppressing DHC production through oral administration of finasteride or such. In these cases, countermeasures based on the present invention are thought to be effective.

One of the embodiments of the present invention relates to pharmaceutical compositions for use in treating or preventing alopecia in which hair progressively becomes thinner, in particular, any alopecia selected from the group consisting of senile alopecia, male pattern alopecia, diffuse alopecia, female pattern alopecia, drug alopecia, and scarring alopecia, which are characterized in comprising an agent that promotes the repair of DNA damage accompanying hair cycling, a DNA damage-suppressing agent, type XVII collagen protein or a nucleic acid encoding thereof, or an agent that stabilizes type XVII collagen or an agent that allows its stable expression. In other words, one of the embodiments of the present invention relates to use of an agent that promotes the repair of DNA damage accompanying hair cycling, a DNA damage-suppressing agent, type XVII collagen protein or a nucleic acid encoding thereof, or an agent that stabilizes type XVII collagen or an agent that allows its stable expression in the manufacturing of medicaments. As described above, the inventors discovered that when there is a deficiency of COL17A1 due to neutrophil elastase (ELANE) induced by DNA damage as a result of aging, hair cycle progression, X-ray irradiation or such, or other COL17A1 degrading enzymes, hair follicle stem cells lose their stem cell signature and induce epidermal differentiation in the niche, and they undergo terminal differentiation to keratinocytes and are released from the skin surface; and as a result, this causes gradual hair follicle miniaturization or hair loss. Thus, it is understood by skilled artisans that it may be possible to treat or prevent alopecia such as senile alopecia or male pattern alopecia by stabilizing or increasing the quantity of type XVII collagen in hair follicle stem cells using a DNA damage repair-promoting agent, a DNA damage-suppressing agent, type XVII collagen protein or a nucleic acid encoding thereof, or an agent or a nucleic acid that induces or stabilizes its expression. In previous prior art reports, it is said that COL17A1 can be normalized by supplementing COL17A1 in congenital COL17A1 deficiency, while nothing was known about the relationship between aging-associated hair loss and type XVII collagen. Gradual hair follicle miniaturization has been considered as a feature of male pattern alopecia, and since it has been confirmed that it progresses with age, it is thought that aging-associated progression in cases of male pattern alopecia or female pattern alopecia may be suppressed or improved by promoting the function of repairing DNA damage, suppressing DNA damage, recovering or stabilizing type XVII collagen expression, or increasing type XVII collagen-expressing cells. Thus, one of the embodiments of the present invention relates to pharmaceutical compositions for use in treating or preventing alopecia that undergoes the process of progressive hair thinning (hair follicles miniaturization) (senile alopecia, male pattern alopecia and female pattern alopecia), which are characterized in comprising a compound or nucleic acid that promotes the function of repairing DNA damage, suppressing DNA damage, or increasing the expression of type XVII collagen (COL17A1) or cells expressing thereof in cells such as hair follicle stem cells or keratinocytes, and a method of treating or preventing alopecia that undergoes the process of progressive hair thinning (hair follicles miniaturization) (senile alopecia, male pattern alopecia, and female pattern alopecia), which comprises (i) a compound or nucleic acid that increases or stabilizes the expression of type XVII collagen (COL17A1) in cells such as hair follicle stem cells or keratinocytes, (ii) a compound or nucleic acid that increases type XVII collagen-expressing cells, or (iii) a compound or nucleic acid that promotes the repair of DNA damage or suppresses DNA damage in cells such as hair follicle stem cells or keratinocytes.

One of the embodiments of the present invention relates to a method of treating or preventing alopecia in which hair progressively becomes thinner, in particular, any alopecia selected from the group consisting of senile alopecia, male pattern alopecia, diffuse alopecia, female pattern alopecia, drug alopecia, and scarring alopecia, which comprises administering the type XVII collagen protein or a nucleic acid encoding thereof to a subject. The subject in this treatment/prevention method is a mammal, and typically a human. The gene sequence of type XVII collagen is public knowledge, and a variant of type XVII collagen with the introduction of one or more mutations may also be used. Methods for producing such a variant are public knowledge to those skilled in the art.

Further, one of the embodiments of the present invention relates to a method of treating or preventing alopecia in which hair progressively becomes thinner, in particular, any alopecia selected from the group consisting of senile alopecia, male pattern alopecia, diffuse alopecia, female pattern alopecia, drug alopecia, and scarring alopecia, which comprises administering a DNA damage repair-promoting agent or a DNA damage-suppressing agent to a subject. For the DNA damage repair-promoting agent used in the compositions or methods described in the present specification, for example, *Gigartina tenella* extract (reference to Japanese published unexamined patent application publication No.: 2006-273761), *Cinchona* extract (reference to WO2013/031003) or such can be used. The ability of DNA damage repair-promoting agent to repair DNA damage can be assessed using any arbitrary method known to skilled artisans such as the host-cell reactivation assay. For the DNA damage-suppressing agent used in the compositions or methods described in the present specification, for example, *Sarcandra glabra* extract, *Saraca dives* extract, *Cudrania pubescens* extract, *Taxodium distichum* extract, *Ludwigia octovalis* extract, *Deutzianthus tonkinensis* extract, *Alchornea trewioides* extract, *Berchemia polyphylla* extract, *Glochidion puberum* extract, *Sassafras tzumu* extract (reference to Japanese published unexamined patent application publication No.: 2008-247854), *Cinchona* extract, comfrey extract, *Coffea* extract, *Pueraria* root extract, burdock extract, *Coptis* root extract, *Sophora angustifolia* extract, *Chlorella vulgaris* extract, *Lavandula vera* extract, *Oenothera biennis* extract, rose extract, *Gynostemma* extract, *Rabdosia japonica* extract, *Lamium album* extract, carrot extract, Japanese linden extract, *Sanguisorba officinalis*, *Lotus* extract, *Tea* extract, and okra extract (WO2013/031003). The DNA damage-suppressing ability of a DNA damage-suppressing agent can be assessed using any arbitrary method known to skilled artisans such as COMET assay or assay of detecting DNA damage focus induced in DNA damage response.

Further, one of the embodiments of the present invention relates to a method of screening for compounds that are useful for the treatment or prevention of alopecia in which hair progressively becomes thinner, in particular, any alopecia selected from the group consisting of senile alopecia, male pattern alopecia, diffuse alopecia, female pattern alopecia, drug alopecia, and scarring alopecia, and/or suppression of graying. Such screening method comprises (i) contacting a compound with hair follicle stem cells or keratinocytes in vitro, (ii) investigating change in the amount of type XVII collagen expression in the hair follicle stem cells, and (iii) identifying the compound that increases or stabilizes the amount of type XVII collagen expression in hair follicle stem cells or keratinocytes. Measurement of the quantity of type XVII collagen expression can be carried out using any arbitrary method known to skilled artisans. Substances identified by the above screening method are useful as ingredients of the pharmaceutical compositions of the present invention for use in treatment or prevention of alopecia such as senile alopecia or male pattern alopecia. Further, in the methods of the present invention for treating or preventing alopecia such as senile alopecia or male pattern alopecia, they are also useful as substances to be administered to the subject.

The above-mentioned screening method may comprise (i) contacting a compound with hair follicle stem cells or keratinocytes in vitro, (ii) investigating change in the DNA damage-repairing ability in the hair follicle stem cells or keratinocytes, and (iii) identifying the compound that increases the DNA damage-repairing ability in the hair follicle stem cells or keratinocytes. Measurement of the quantity of type XVII collagen expression can be carried out using any arbitrary method known to skilled artisans. Assessment of change in the DNA damage-repairing ability can be carried out using any arbitrary method known to skilled artisans, for example, host-cell reactivation assay. Substances identified by such screening method are useful as ingredients of the pharmaceutical compositions of the present invention for use in treatment or prevention of alopecia such as senile alopecia or male pattern alopecia. Further, in the methods of the present invention for treating or preventing alopecia such as senile alopecia or male pattern alopecia, they are also useful as substances to be administered to the subject.

Hereinbelow, the present invention will be explained in detail with the Examples, without being limited thereto in any way.

EXAMPLES

Figure 1B:
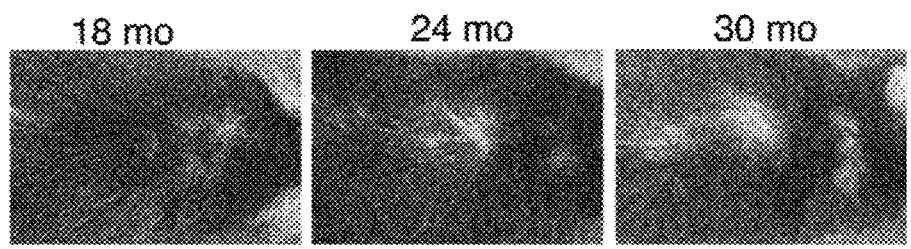
FIG. 1B The photos show that in aged mice (≥18 months of age), hair loss is characteristically observed on the neck and body trunk of the back.
Figure 1C:
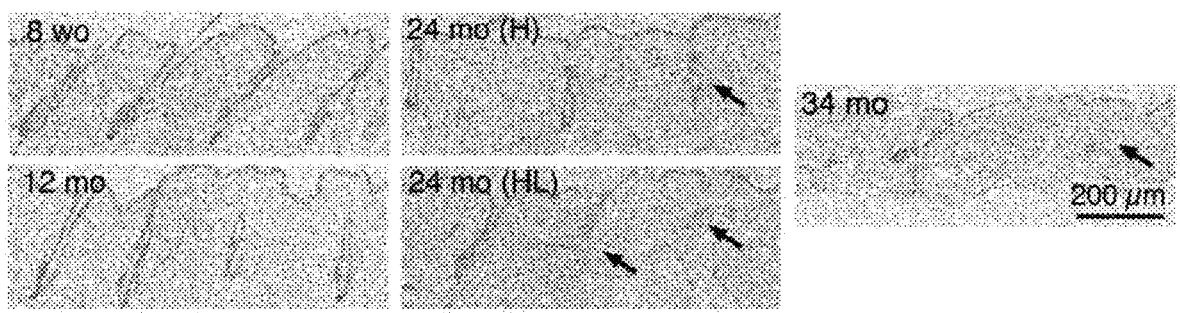
FIG. 1C They are representative photos of hematoxylin and eosin stained dorsal skin of young mice (8 weeks of age), middle-aged mice (12 months of age), and aged mice (24 and 34 months of age).
Figure 1D:
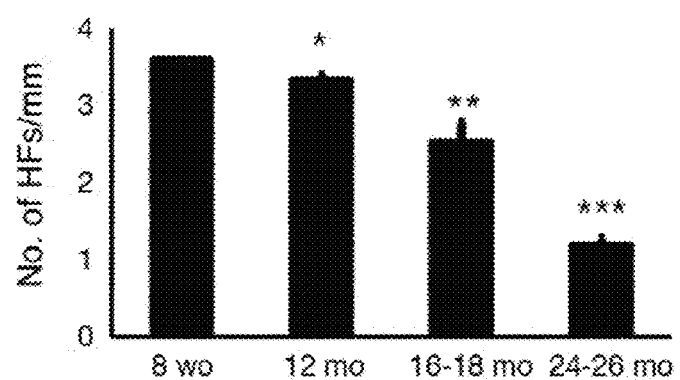
FIG. 1D It is a graph that shows the number of hair follicles per mm.
Figure 1E:
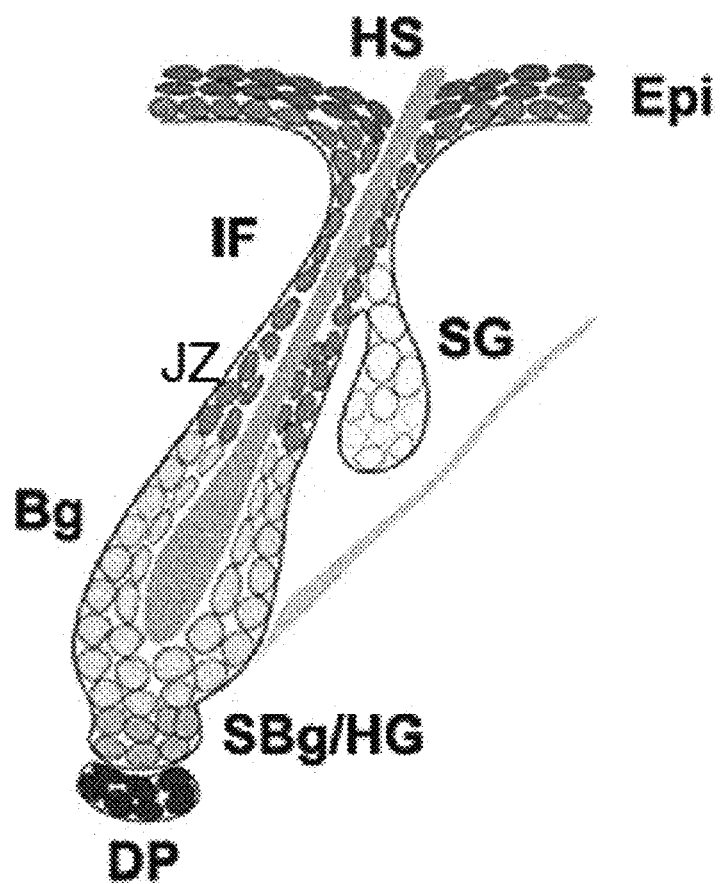
FIG. 1E It is a schematic diagram of hair follicles in the telogen phase.
Figure 1F:
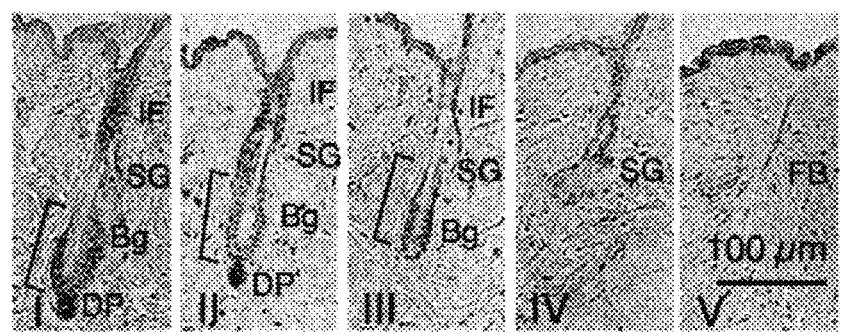
FIG. 1F It is a photo showing staging of chronological hair follicle aging.
Figure 1G:
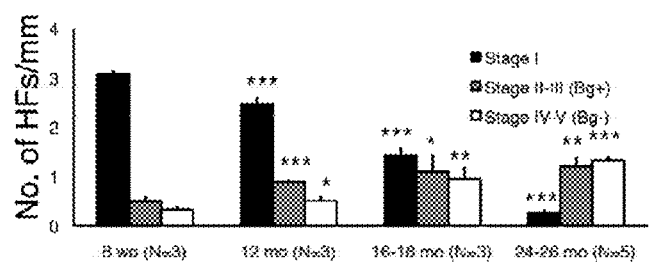
FIG. 1G The graph shows the number of each hair follicle stages per mm.
Figure 1H:
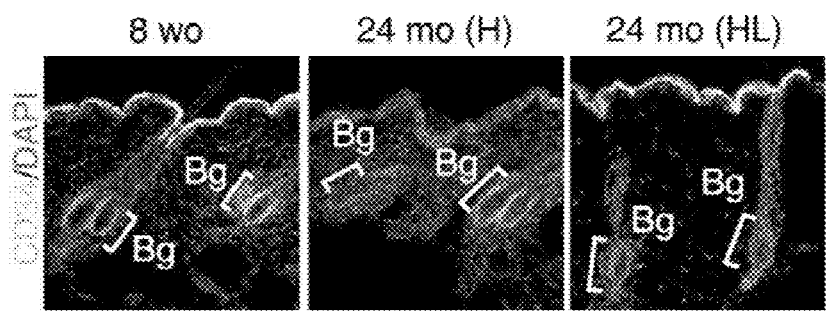
FIG. 1H It shows immunostaining images with the hair follicle stem cell marker CD34 at 8 weeks and at 24 months of areas with hair follicles (H) and areas without hair follicles (HL).
Figure 1I:
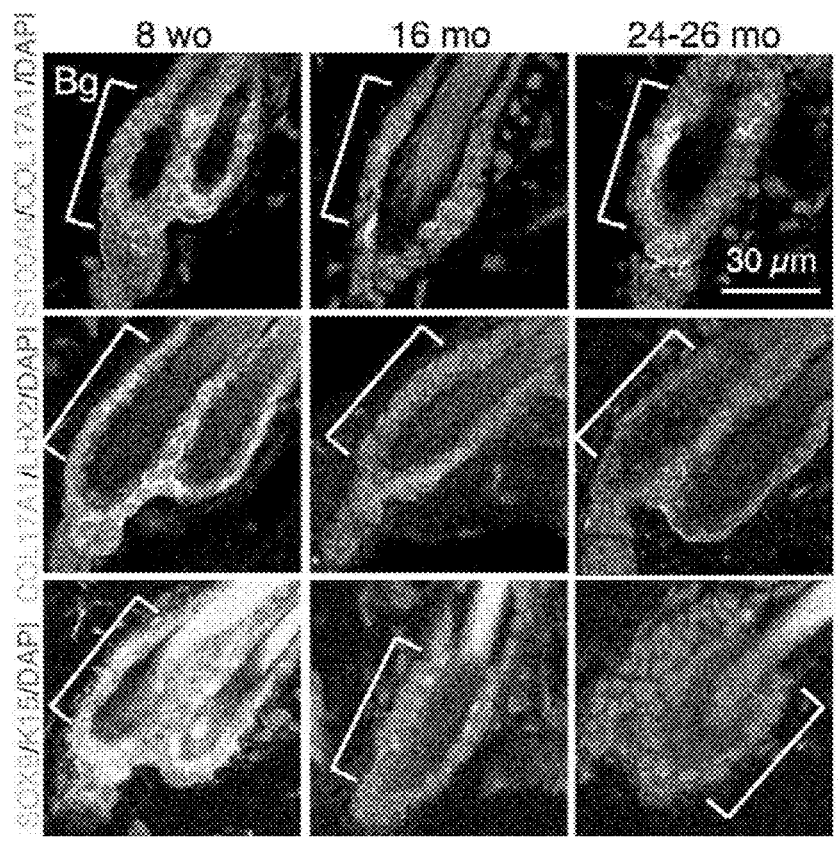
FIG. 1I They are immunostaining images for hair follicle stem cell markers COL17A1, LHX2, and SOX9 at 8 weeks, 16 months, and 24 to 26 months.
Figure 1J:
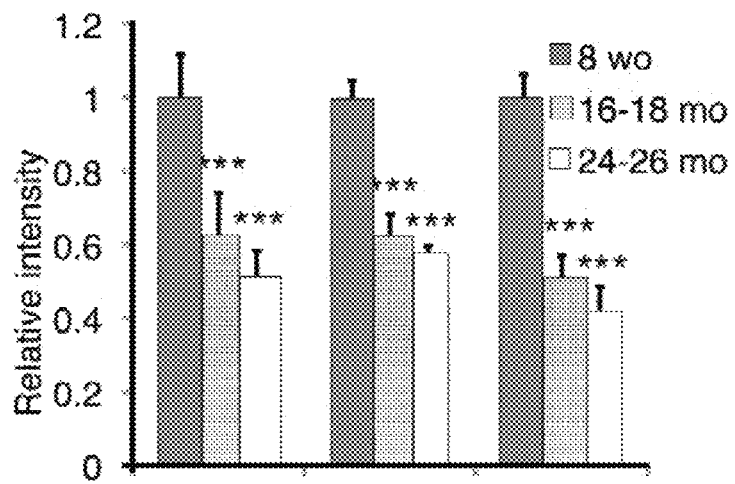
FIG. 1J It shows a quantitative analysis of fluorescence intensity of immunostaining with hair follicle stem cell markers COL17A1, K15, and S100A6 in 8-week-old, 16-month-old, and 24- to 26-month-old mice.
Figure 1K:
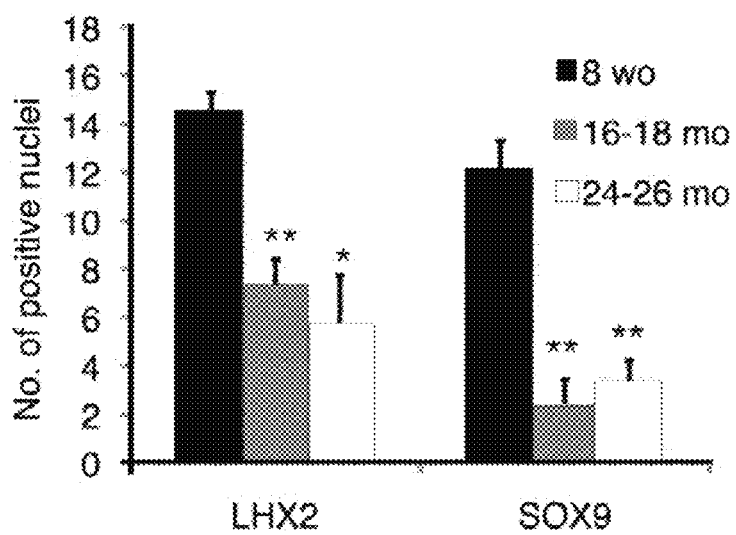
FIG. 1K It shows a quantitative analysis of the amount of nuclear-positive cells by immunostaining with hair follicle stem cell markers LHX2 and SOX9 in 8-week-old, 16-month-old, and 24- to 26-month-old mice.
Figure 1L:
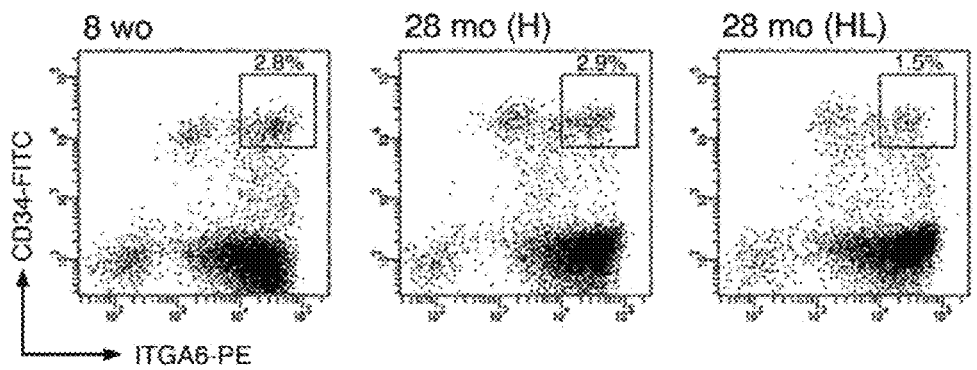
FIG. 1L It shows an analysis of the FACS fractions of hair follicle stem cells (CD34-strongly positive, ITGA6-strongly positive, SCA-I-negative) in 8-week-old and in 28-month-old mice.

Example 1: Analysis of the Loss of Hair Follicle Stem Cell Signature and Hair Follicle Miniaturization which Precede Aging-Associated Hair Thinning and Hair Loss FIGS. 1A to 1G show aging-associated hair loss and hair follicle miniaturization in C57BL/6 wild-type mouse. FIG. 1A shows representative photos of young mice (8 week of age) and aged mice (28 months of age). FIG. 1B shows that in aged mice (≥18 months of age), hair loss is characteristically observed on the neck and body trunk of the back. When observed over time, the hair loss appeared to expand as it diffused from side to side and top and down. FIG. 1C shows representative photos of hematoxylin and eosin stained dorsal skin of young mice (8 weeks old), middle-aged mice (12 months old), and aged mice (24 and 34 months old). The arrows show miniaturized hair follicles. FIG. 1D is a graph that shows the number of hair follicles per mm. FIG. 1E is a schematic diagram of hair follicles in the telogen phase. HS shows hair shaft (hair root). IF shows infundibular hair follicle. SG shows sebaceous gland. JZ shows hair follicle junctional zone. Bg shows hair bulge (bulge). sBg/HG shows hair bud (sub-bulge). DP shows derma papilla. FIG. 1F is a photo showing staging of chronological hair follicle aging, and shows representative histological images at different hair follicle stages. Stage I: hair follicles with standard structure and size; Stage II: shortened (miniaturized) hair follicles including derma papilla; Stage III: miniaturized hair follicles with complete loss of the derma papilla; Stage IV: miniaturized hair follicles retaining sebaceous glands with loss of hair follicle bulge and hair shaft; Stage V: complete disappearance of hair follicles, occasionally with mild fibrosis. FIG. 1G is a graph showing the number of each hair follicle stage per mm. More than 100 hair follicles from multiple samples were examined for each group. FIGS. 1H to 1K show reduction of hair follicle stem cell markers with aging. FIG. 1H shows immunostaining images with the hair follicle stem cell marker CD34 at 8 weeks and at 24 months of areas with hair follicles (H) and areas without hair follicles (HL). FIG. 1I shows immunostaining images of Stage I at 8 weeks, 16 months, and 24 to 26 months for hair follicle stem cell markers COL17A1, LHX2, and SOX9. FIG. 1J shows a quantitative analysis of fluorescence intensity of immunostaining with hair follicle stem cell markers COL17A1, K15, and S100A6 in 8-week-old, 16-month-old, and 24- to 26-month-old mice. Stages I and II from each group were examined (N=3 mice). FIG. 1K shows a quantitative analysis of the number of LHX2+ and SOX9+ nuclei in bulge cells of 8-week-old, 16-month-old, and 24-month-old mice. FIG. 1L shows FACS analyses of the CD34-strongly positive, ITGA6-strongly positive, SCA-I-negative fraction to detect hair follicle stem cells in young (8-week-old) and aged (28-month-old) mice. At 28 months of age, the hair follicle stem cell fraction in areas with hair follicles (H) is maintained, while there is a reduction in areas without hair follicles.

Figure 2A:
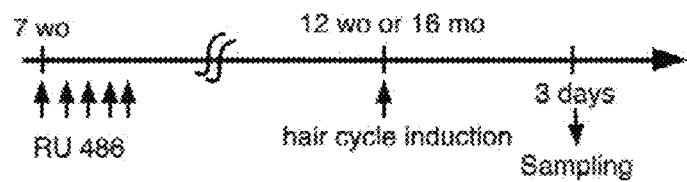
FIG. 2A It shows an experimental design for genetic fate analysis of hair follicle stem cell-derived cells.
Figure 2B:
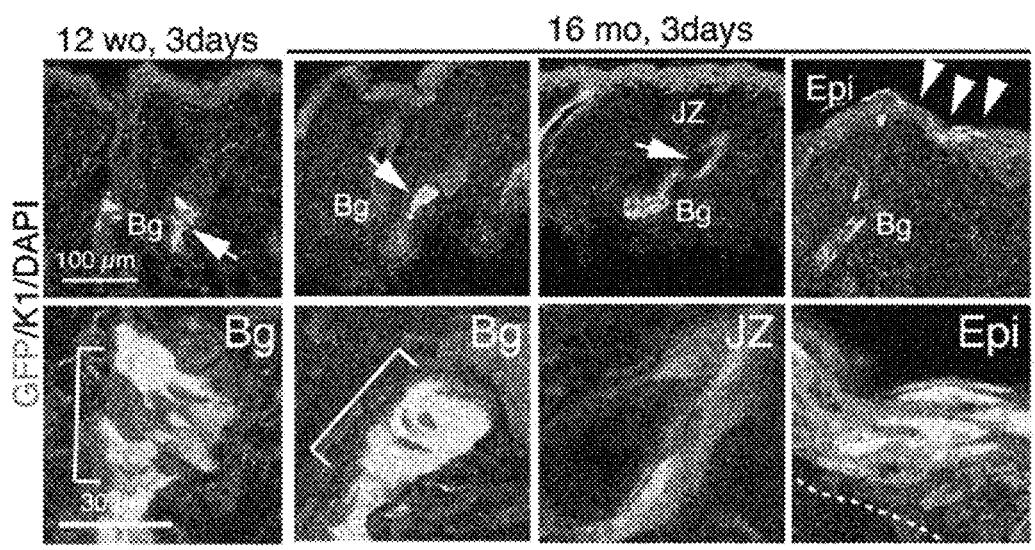
FIG. 2B Immunostaining images for EGFP expression and Keratin 1 in K15-crePR; CAG-CAT-EGFP mice after hair cycling induction.
Figure 2C:
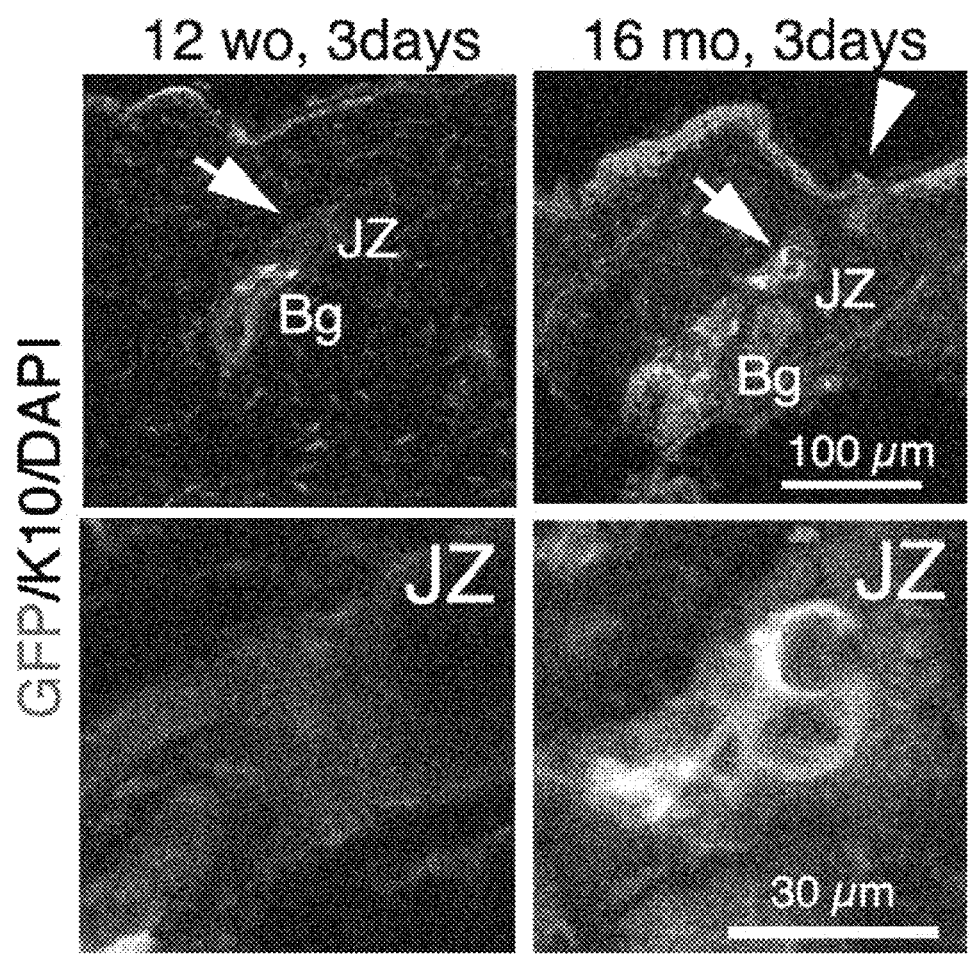
FIG. 2C Immunostaining images for EGFP expression and Keratin 10 in K15-crePR; CAG-CAT-EGFP mice after hair cycling induction.
Figure 2D:
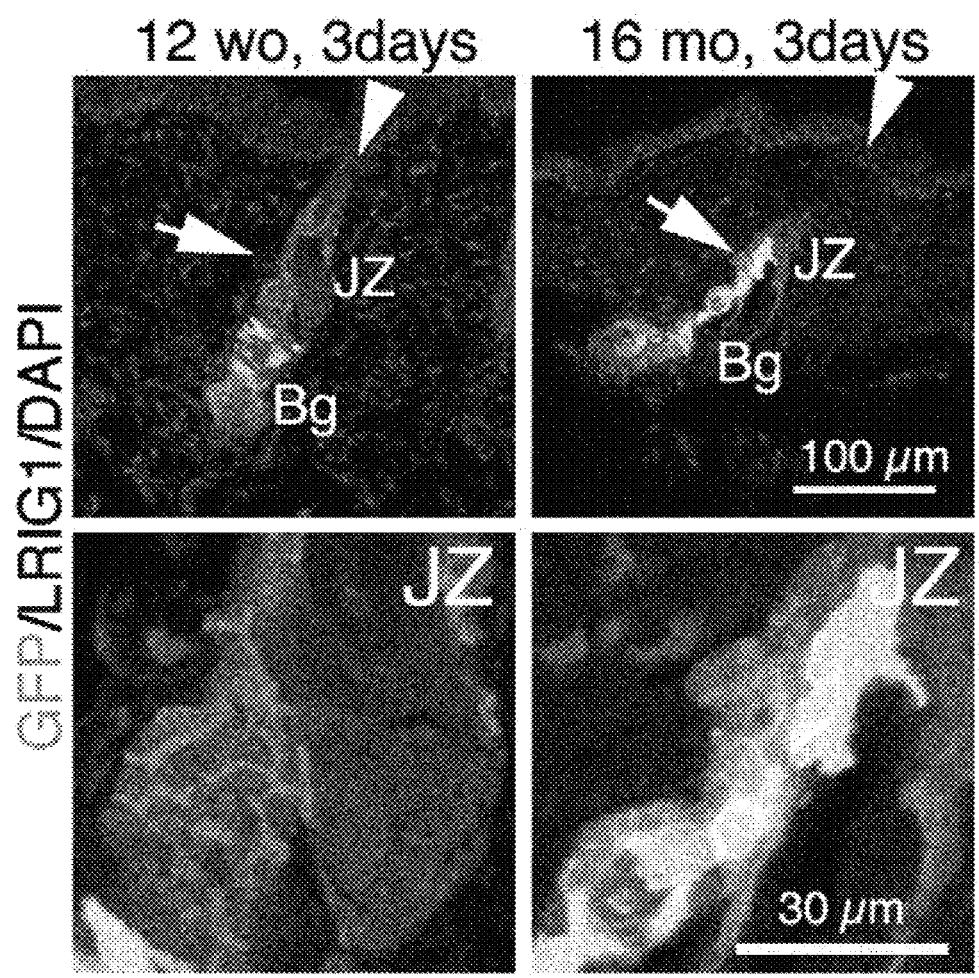
FIG. 2D Immunostaining images for EGFP expression and LRIG1 in K15-crePR; CAG-CAT-EGFP mice after hair cycling induction.
Figure 2E:
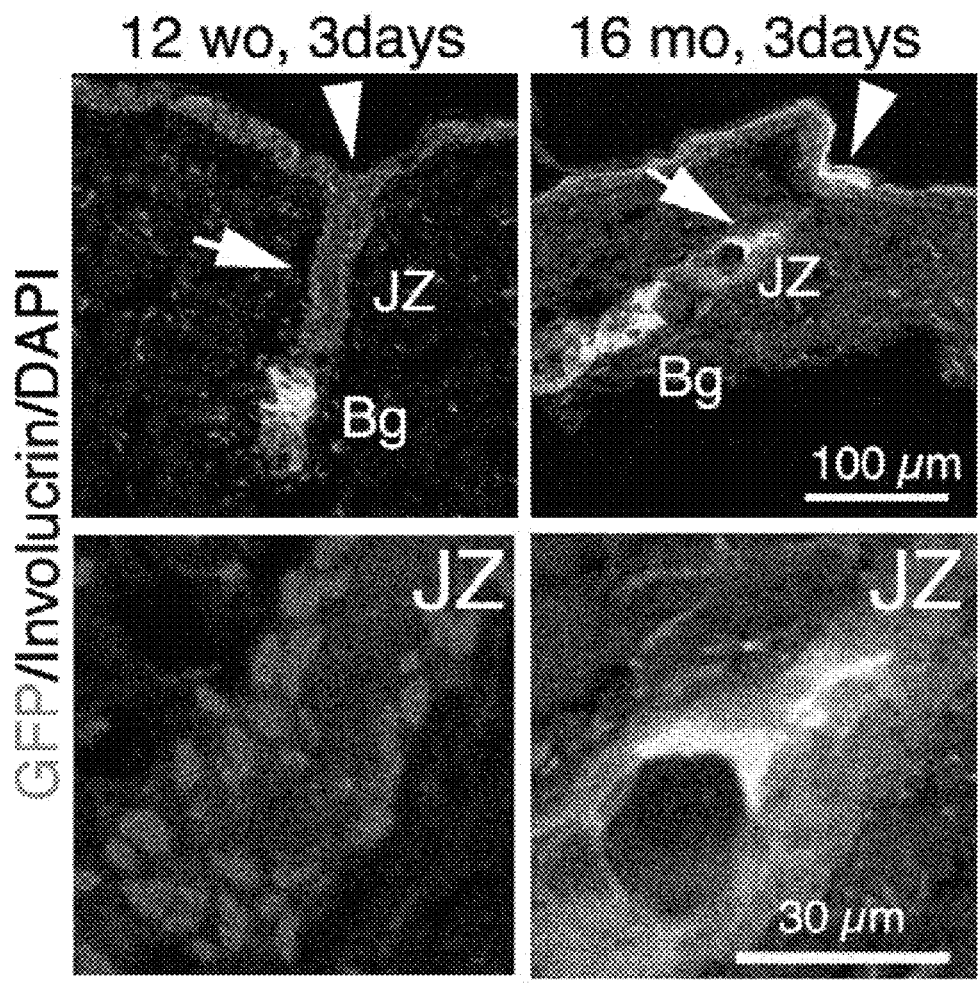
FIG. 2E Immunostaining images for EGFP expression and Involucrin in K15-crePR; CAG-CAT-EGFP mice after hair cycling induction.
Figure 2F:
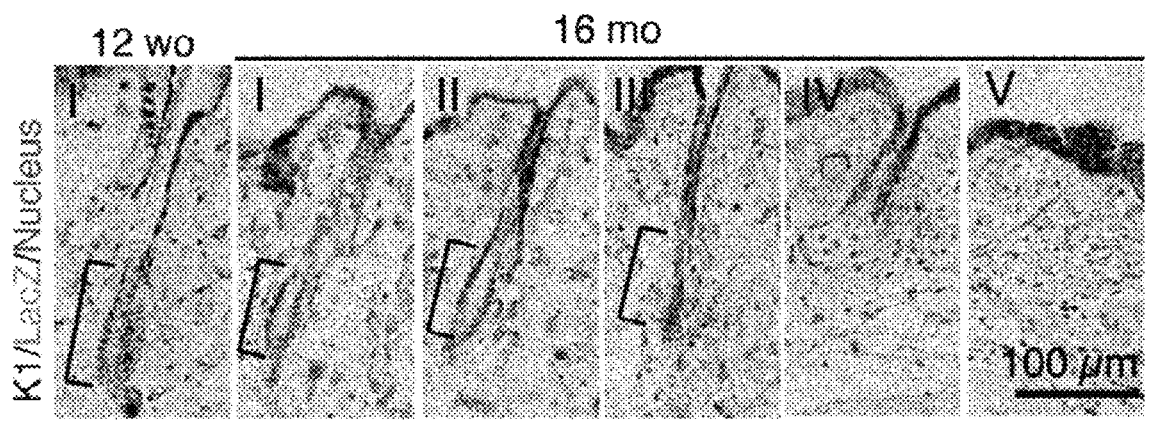
FIG. 2F The photo shows that hair follicle stem cell-derived LacZ+ cells appear in the bulge (Bg) cells at Stages I to III, the junctional zone (JZ) cells at Stages III to IV, and the epidermal cells (Epi) at Stage V.
Figure 2G:
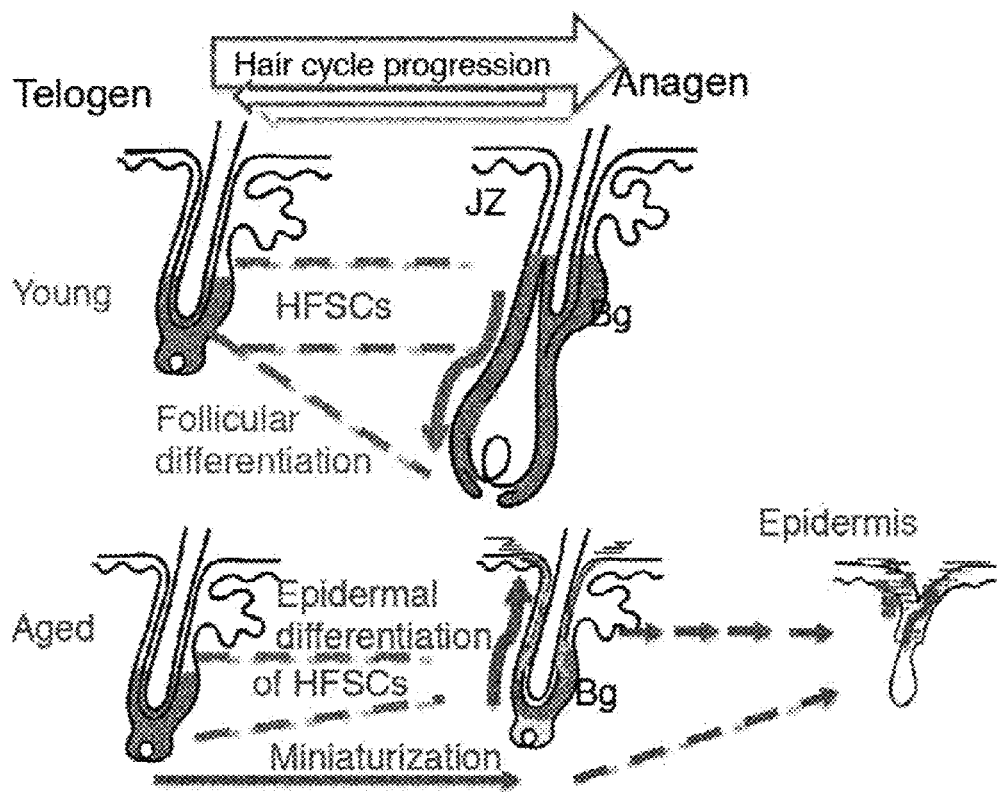
FIG. 2G It is a schematic diagram for the fate of hair follicle stem cells.
Figure 2H:
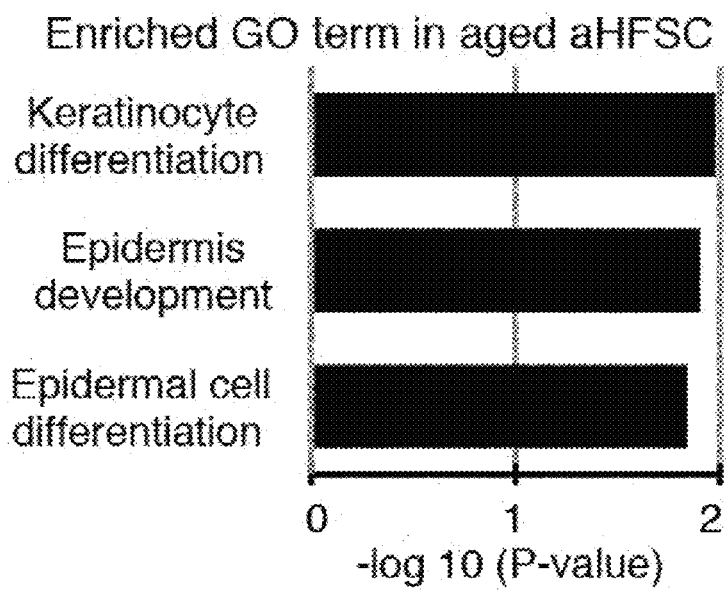
FIG. 2H It shows an ontology analysis of genes that have changed 2 fold or more by microarray comparison between young (8 weeks of age) and aged (25-26 months of age) hair follicle stem cells after hair cycling induction.
Figure 2I:
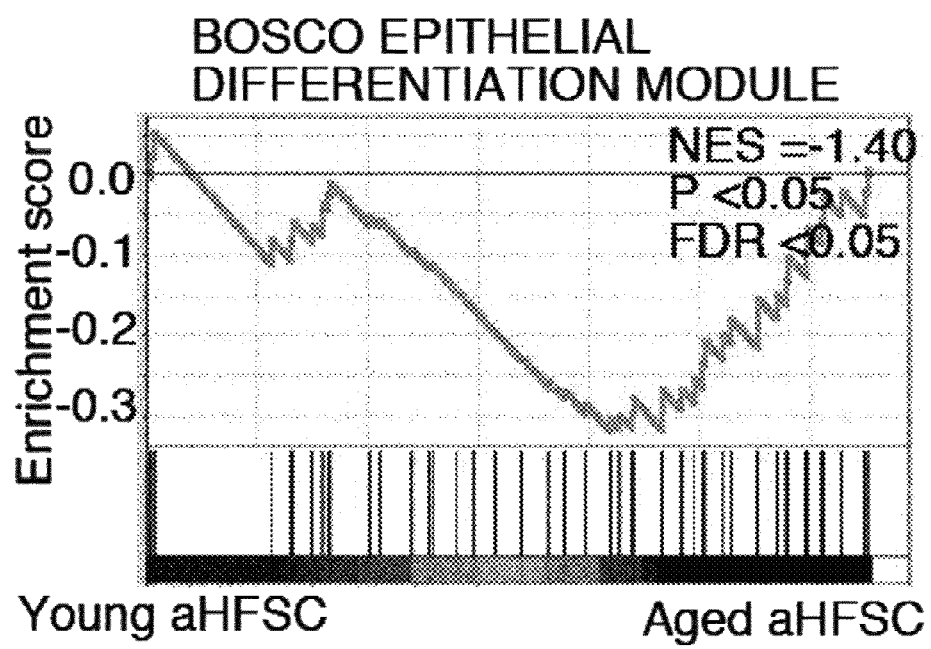
FIG. 2I It shows Gene Set Enrichment Analysis (GSEA) of young versus aged hair follicle stem cells with gene sets for "epithelial differentiation" after hair cycling induction by microarray comparison.
Figure 2J:
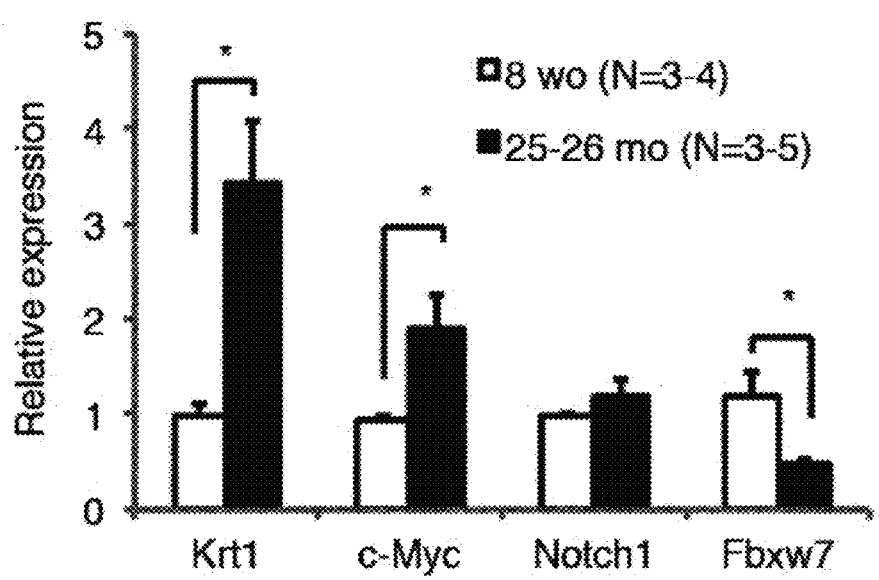
FIG. 2J It shows a quantitative RT-PCR analysis of K1, c-Myc, Notch1, and Fbxw7 gene expression in the hair follicle stem cell fraction from 8-week-old and 25-26-month-old mice.

Example 2: Epidermal Differentiation of Aged Hair Follicle Stem Cells Underlies the Stepwise Progression of Hair Follicle Aging FIG. 2A shows an experimental design for genetic fate analysis of hair follicle stem cell-derived cells. RU486 (mifepristone) was applied on K15-crePR; CAG-CAT-EGFP and K15-crePR; ROSA26R mice at 7 weeks to induce EGFP or LacZ expression in hair follicle stem cells. At 12 weeks (young) or 16 months (aged) of age, skin samples were collected 3 days after hair cycling induction. FIGS. 2B to 2E show immunostaining images for EGFP expression and Keratin 1 (FIG. 2B), Keratin 10 (FIG. 2C), LRIG1 (FIG. 2D), and Involucrin (FIG. 2E) in K15-crePR; CAG-CAT-EGFP mice after hair cycling induction. Keratin 1, Keratin 10, LRIG1 and Involucrin were induced at 16 months after hair cycling induction in the bulge (Bg) or junctional zone (JZ) of hair follicle stem cell-derived cells (shown by arrows). In addition, some of these Keratin 1+ cells appeared in the epidermis (FIG. 2B). FIG. 2F shows results of similar experiments performed using K15-crePR; ROSA26R mice. Immunostaining with Keratin 1 and LacZ revealed that hair follicle stem cell-derived LacZ+ cells are distributed to the bulge (Bg) cells at Stages I to III, the junctional zone (JZ) cells at Stages III to IV, and the epidermal cells (Epi) at Stage V. FIG. 2G is a schematic diagram for the fate of hair follicle stem cells. Young hair follicle stem cells differentiate to hair follicle cells, whereas aged hair follicle stem cells undergo epidermal differentiation, thereby causing hair follicle miniaturization. FIG. 2H shows an ontology analysis of genes that have changed 2 fold or more by microarray comparison between young (8-week-old) and aged (25-26-month-old) hair follicle stem cells after hair cycling induction. The ontology of "epithelial differentiation" in aged hair follicle stem cells was dominantly detected. FIG. 2I shows Gene Set Enrichment Analysis (GSEA) of young versus aged hair follicle stem cells with gene sets for "epithelial differentiation" from microarray comparison. FIG. 2J shows a quantitative RT-PCR analysis of K1, c-Myc, Notch1, and Fbxw7 gene expression in the hair follicle stem cell fraction of 8-week-old and 25-26-month-old mice. Three to five mice (N=3 to 5) for each group, and 2 groups of samples were used.

Figure 3A:
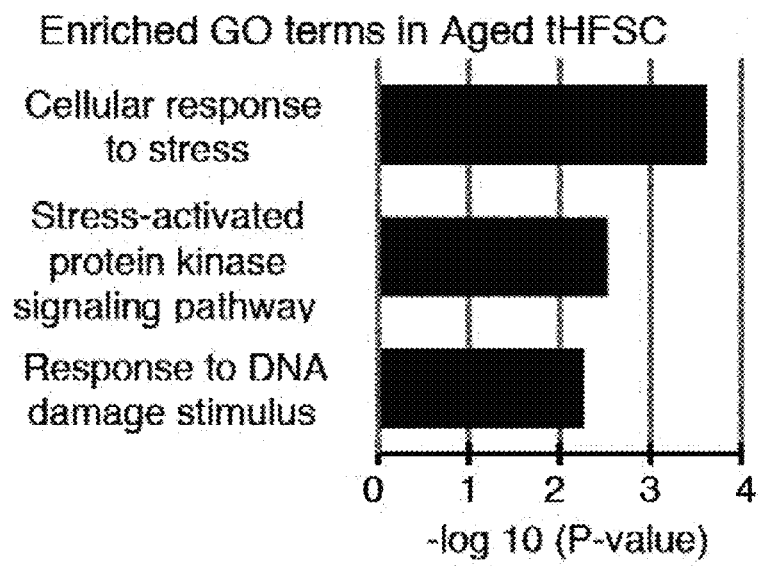
FIG. 3A It shows an ontology analysis for DNA damage response/DNA damage repair in genes up-regulated or down-regulated 2-fold or more in aged (24-25-month-old) hair follicle stem cells by microarray comparison.
Figure 3B:
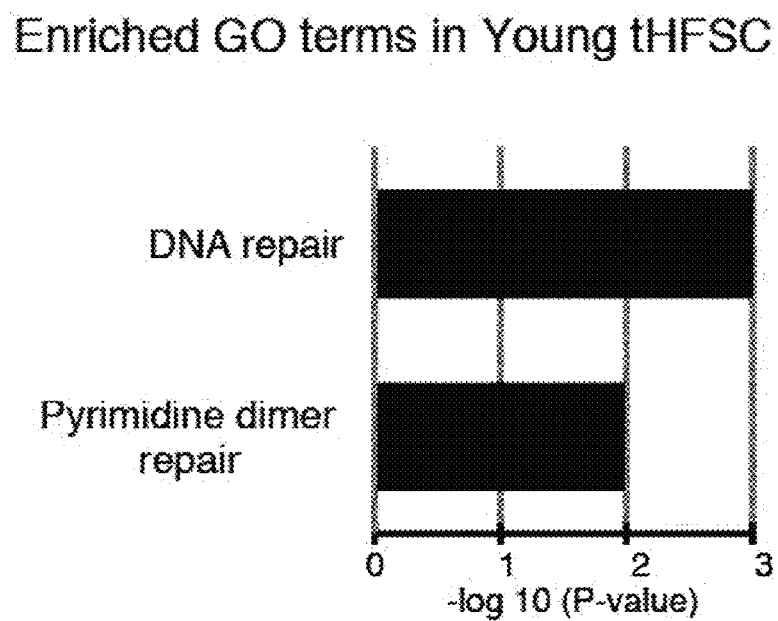
FIG. 3B It shows an ontology analysis for DNA damage response/DNA damage repair in genes up-regulated or down-regulated 2-fold or more in young (8-week-old) hair follicle stem cells by microarray comparison.
Figure 3C:
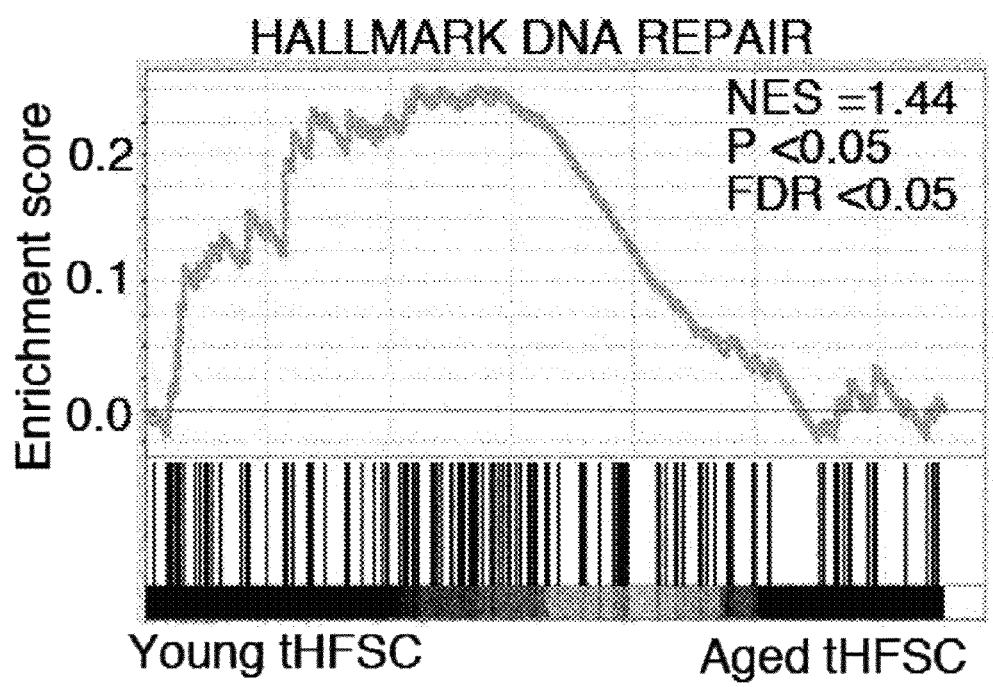
FIG. 3C It shows Gene Set Enrichment Analysis (GSEA) of "DNA repair"-related gene sets by microarray comparison of young and aged hair follicle stem cells.
Figure 3D:
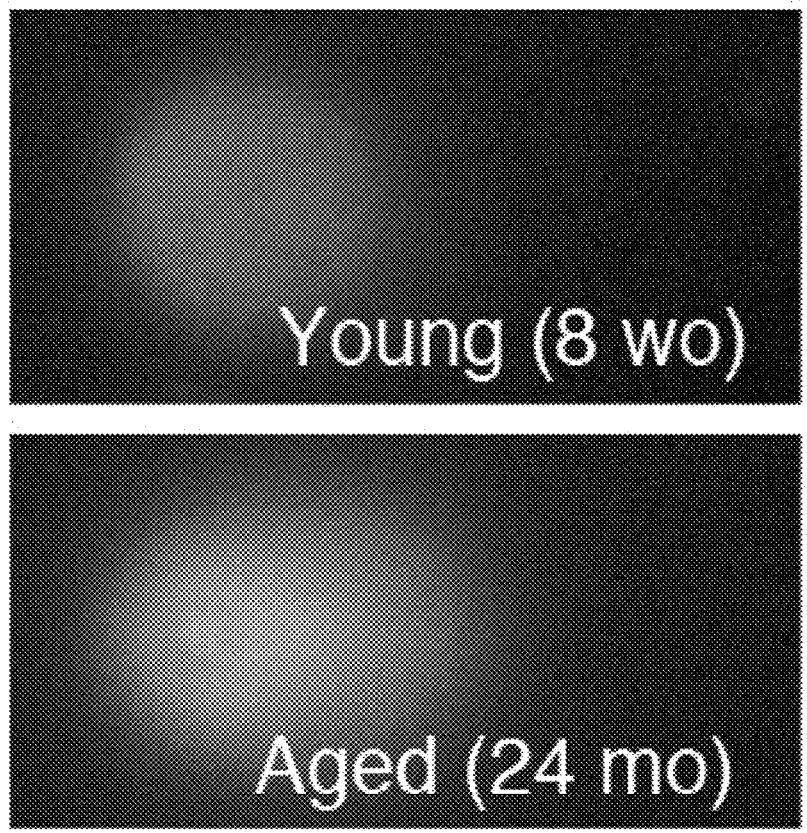
FIG. 3D It is an image of representative damaged DNA fragments (tail moments) stained with cyber green.
Figure 3E:
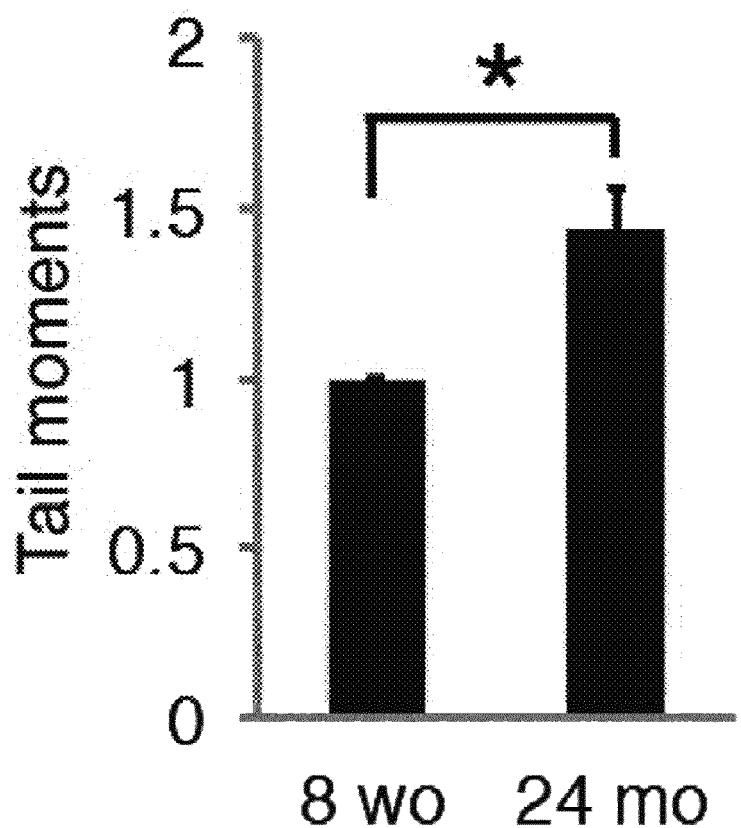
FIG. 3E It is a graph showing frequency of tail moments in young (8-week-old) and aged (24-month-old) hair follicle stem cells.
Figure 3F:
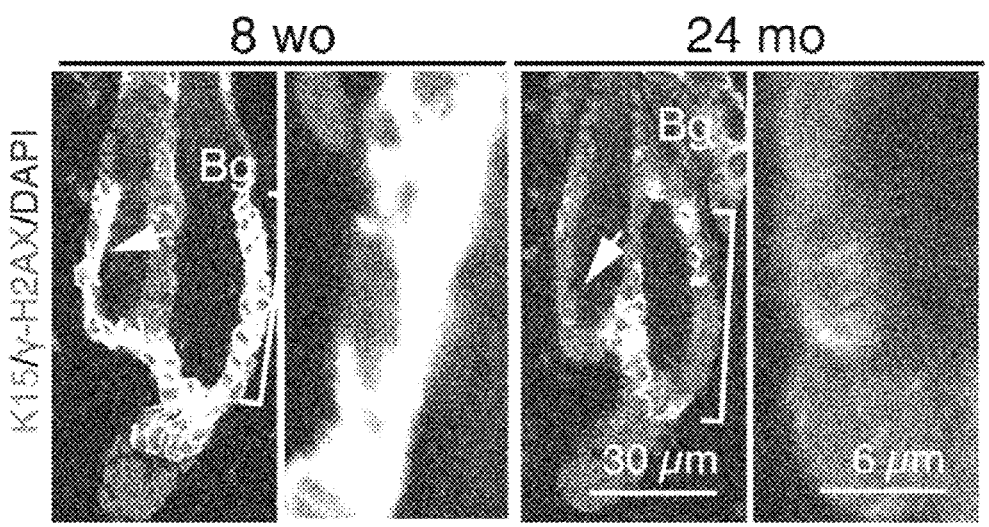
FIG. 3F It shows representative staining images for the DNA damage response marker γ-H2AX in the young (8-week-old) and aged (24-month-old) bulges and sub-bulges.
Figure 3G:
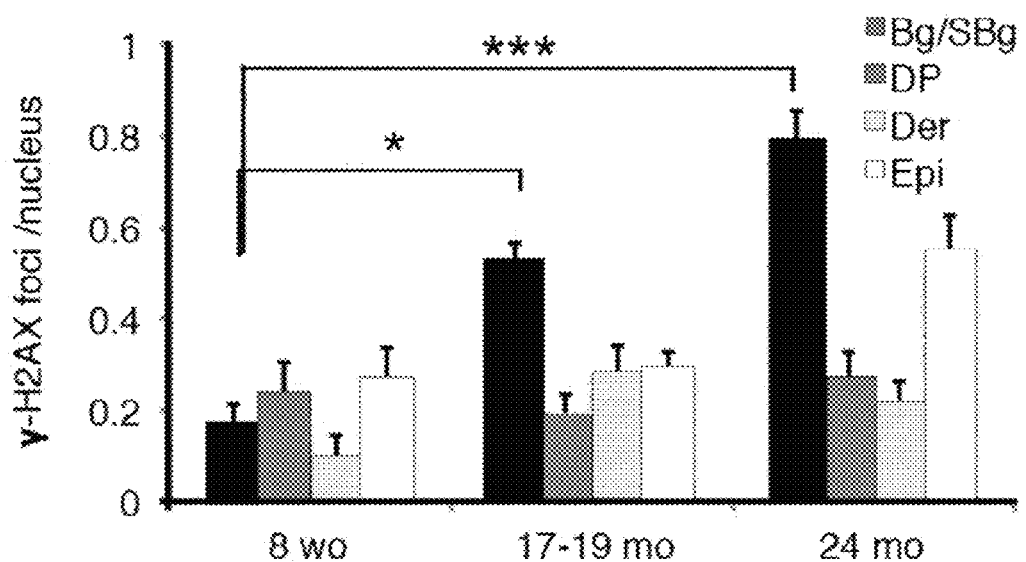
FIG. 3G It is a graph showing nuclear accumulation of γ-H2AX foci in bulges, sub-bulges, hair matrix, epidermis and epithelium.

Example 3: Accumulation of DNA Damage and Sustained DNA Damage Repair in Aged Hair Follicle Stem Cells FIGS. 3A and 3B show an ontology analysis for DNA damage response/DNA damage repair in genes up-regulated or down-regulated 2-fold or more between young (8-week-old) and aged (24-25-month-old) hair follicle stem cells by microarray comparison. The DNA damage repair ability is high at young age, while the DNA damage response is high in aged cells. FIG. 3C shows Gene Set Enrichment Analysis (GSEA) of young versus aged hair follicle stem cells with DNA repair-related gene sets from microarray comparison of young and aged hair follicle stem cells. The expression of the "DNA repair"-related gene sets is high in young cells. FIGS. 3D to 3E show results of DNA damage detection (Comet) analysis of young (8-week-old) and aged (24-month-old) hair follicle stem cells. FIG. 3D is an image of representative damaged DNA fragments (tail moments) stained with cyber green. FIG. 3E is a graph showing frequency of tail moments in young (8-week-old) and aged (24-month-old) hair follicle stem cells. Result of the Comet Assay shows that DNA damage accumulates in hair follicle stem cells with aging. FIG. 3F shows representative staining images for the DNA damage response marker γ-H2AX in the young (8-week-old) and aged (24-month-old) bulges and sub-bulges. FIG. 3G is a graph showing nuclear accumulation of γ-H2AX foci in bulges, sub-bulges, hair matrix, epidermis and epithelium. Two to four mice (N=2-4) were used for each age group. γ-H2AX foci were not observed in any cell population at 8 weeks, but they were significantly increased in the bulges and sub-bulges after 17 months.

Figure 4A:
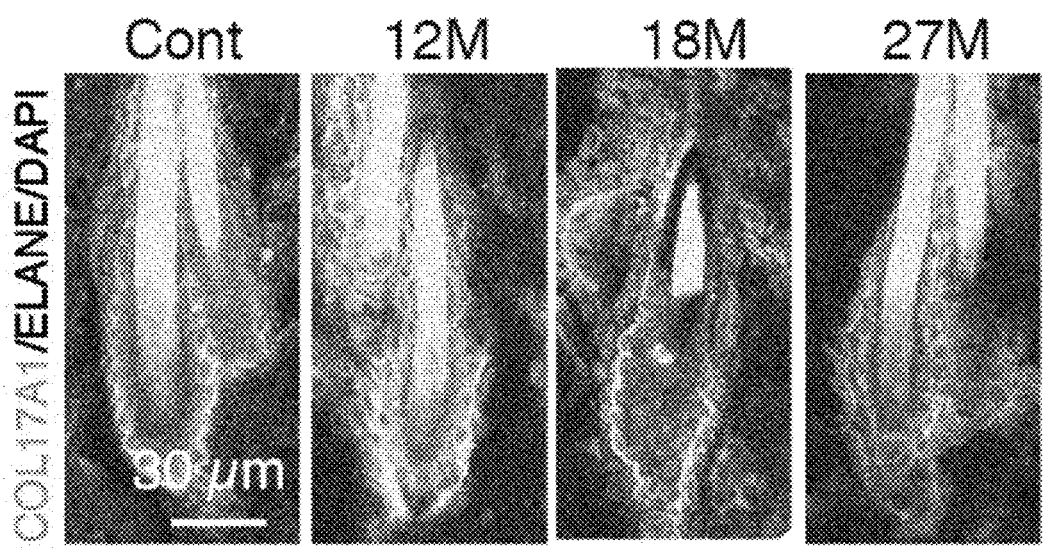
FIG. 4A They are immunostaining images for COL17A1 and ELANE in the hair follicle bulges of young (8-week-old), presenile (12 to 16-month-old), and aged (27-month-old) mice.
Figure 4B:
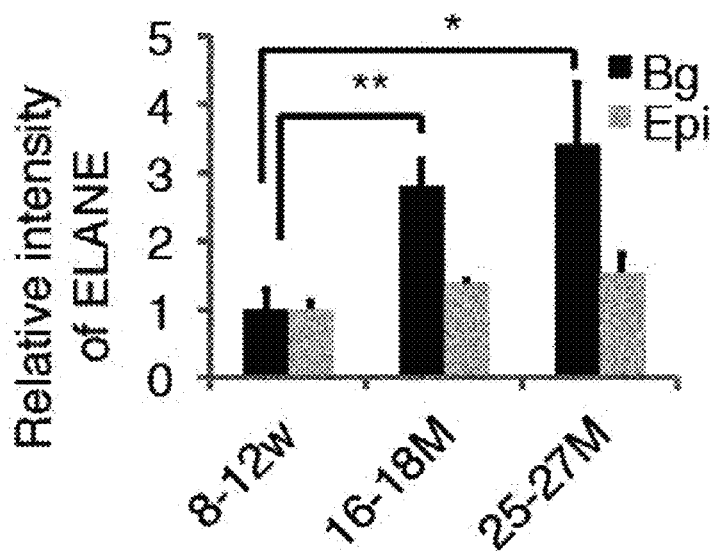
FIG. 4B It shows a quantitative analysis of fluorescence intensity of ELANE in the bulges and epidermis of 8-week-old, 12- to 16-month-old, and 27-month-old mice.
Figure 4C:
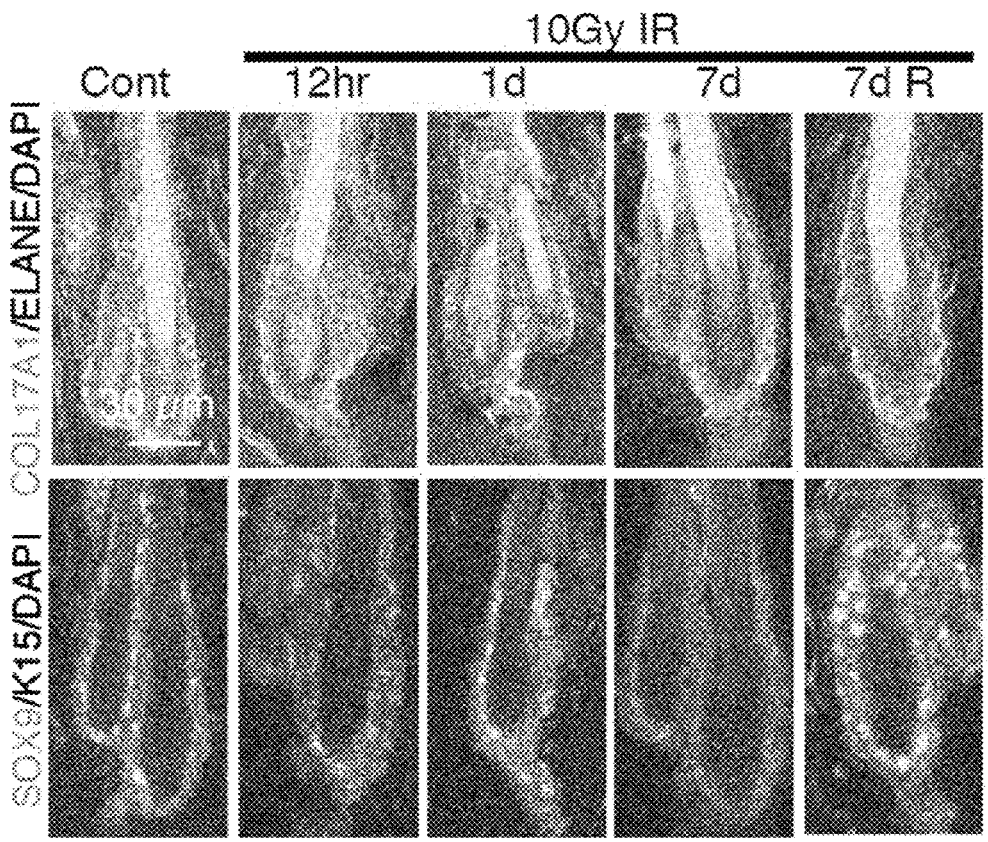
FIG. 4C They are immunostaining images of COL17A1, ELANE, SOX9 and Keratin 15 in the hair follicle bulges 12 hours, 1 day, and 7 days after 10-Gy irradiation.
Figure 4D:
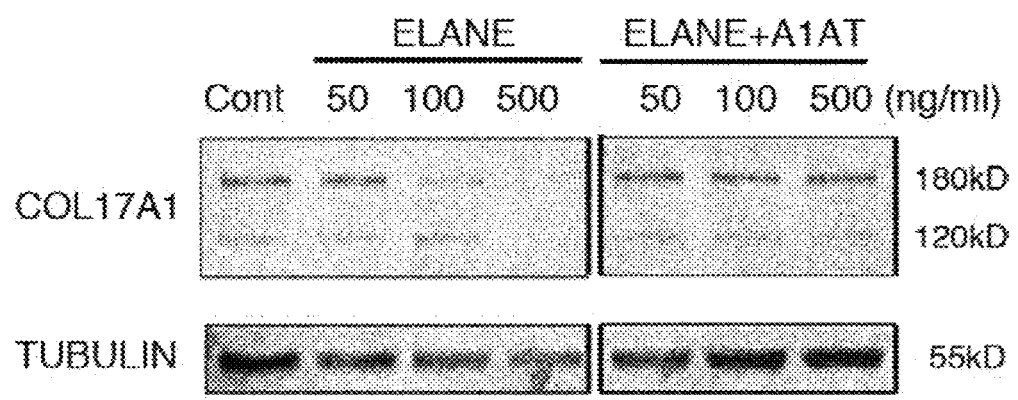
FIG. 4D It is a photo showing Western-blot analysis of primary keratinocytes.
Figure 4E:
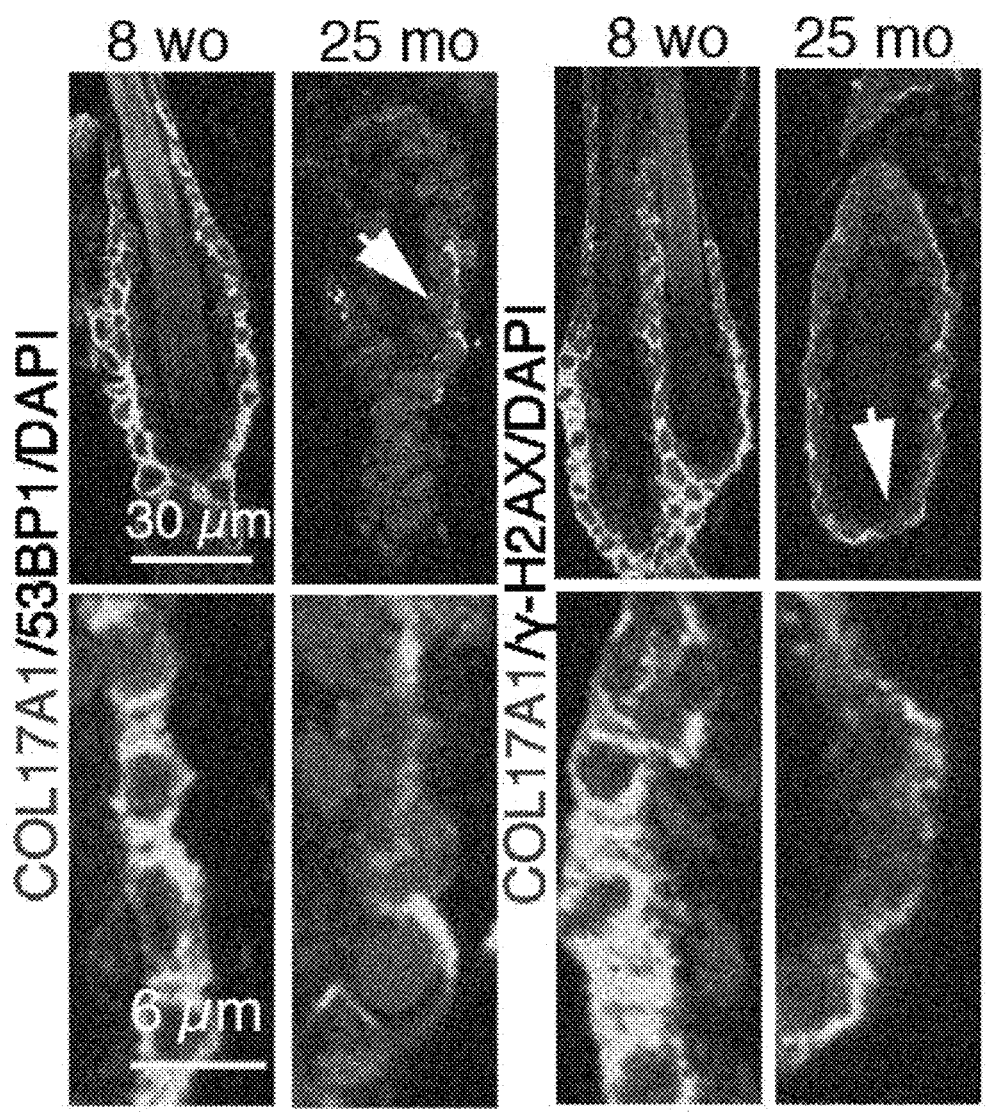
FIG. 4E They are immunofluorescence images of 53BP1 and γ-H2AX foci in COL17A1+ bulges from young (8-week-old) and aged (25-month-old) mice.
Figure 4F:
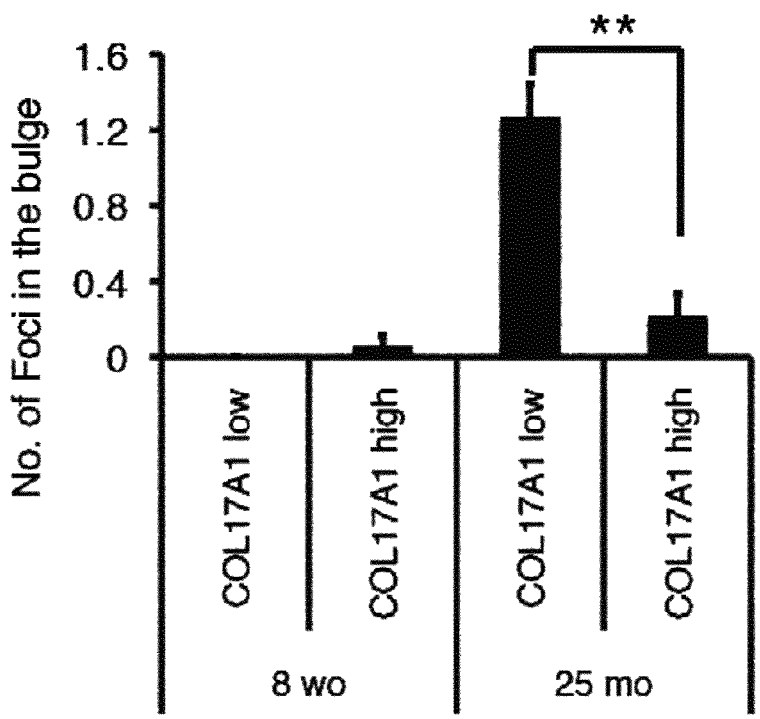
FIG. 4F It is a graph showing the number of 53BP1 foci in the COL17A1-weakly positive and COL17A1-positive areas in the bulge areas of 8-week-old and 25-month-old mice.
Figure 4G:
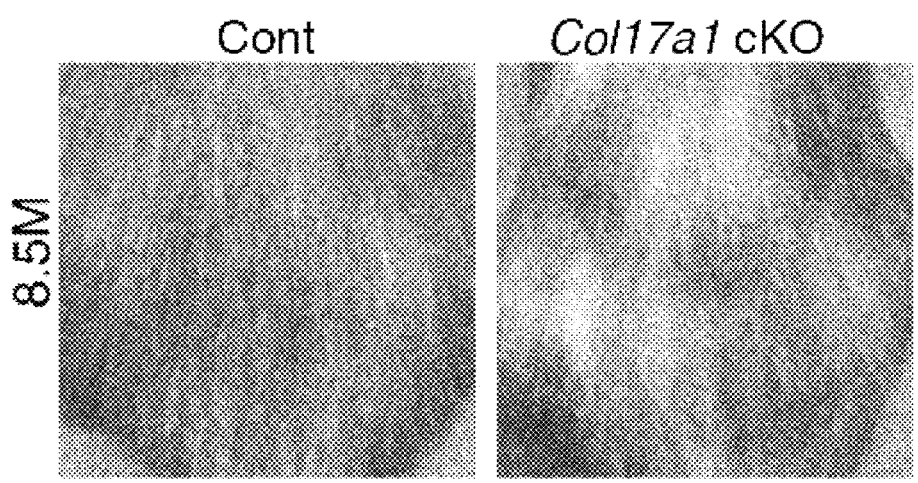
FIG. 4G It is a photo of hair coats on the backs of control and Col17a1 cKO mice at 8.5 months of age.
Figure 4H:
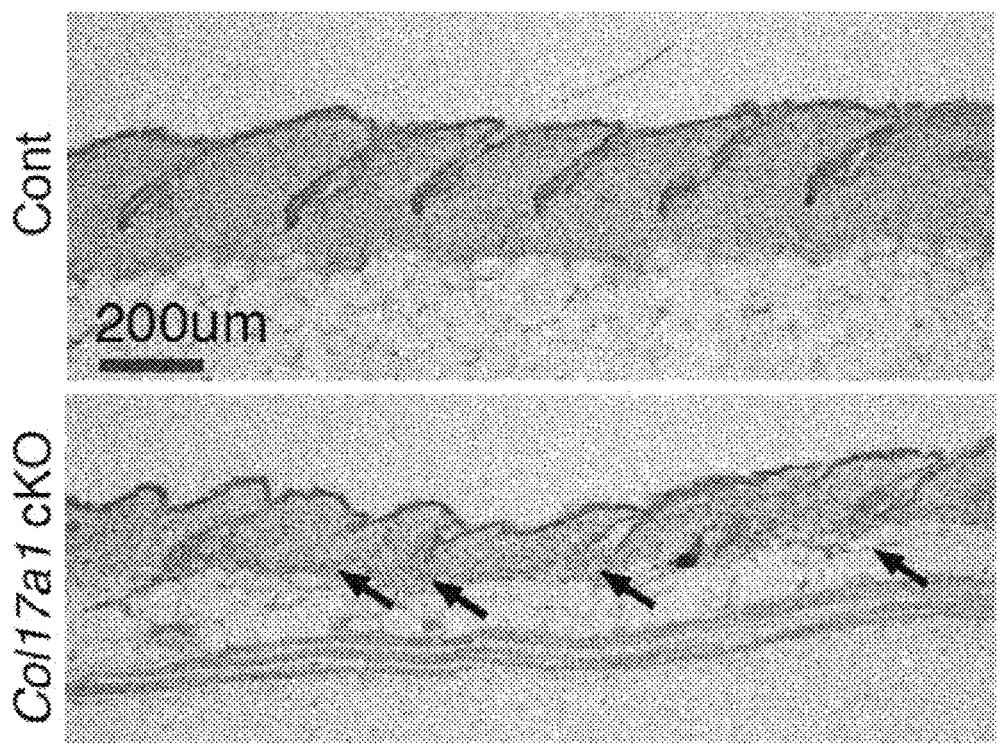
FIG. 4H They are histological images of the control and COL17A1 cKO mice.
Figure 4I:
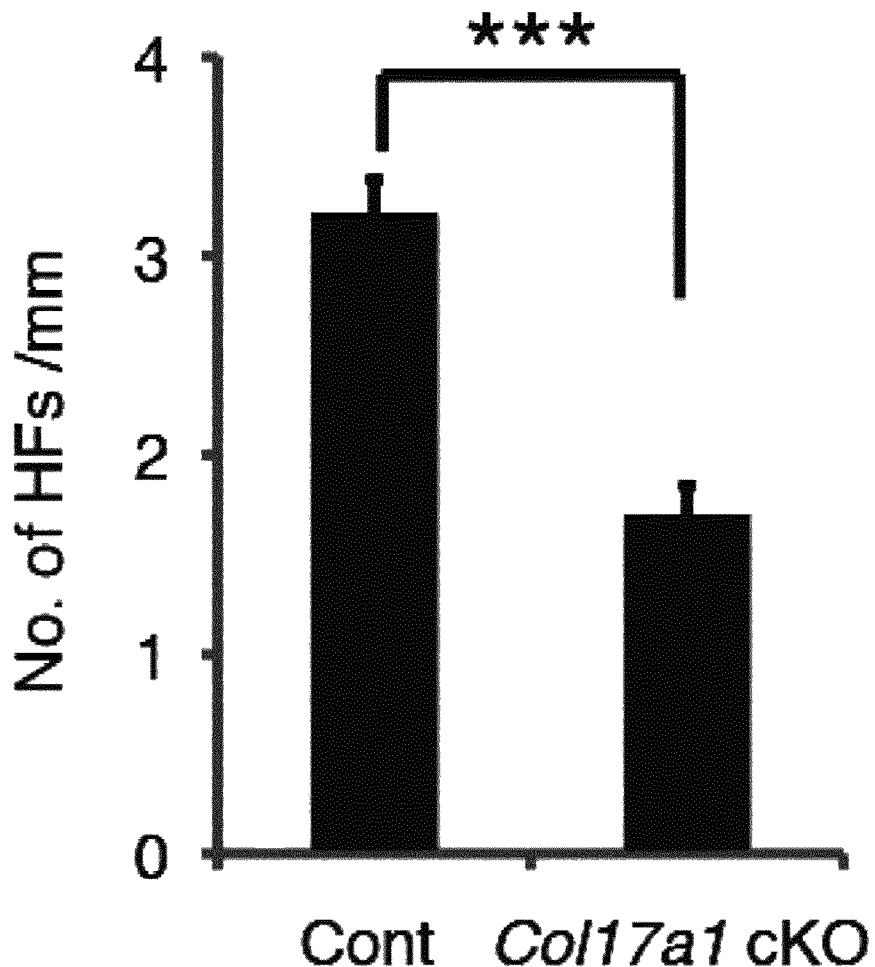
FIG. 4I It is a graph showing the number of hair follicles per mm.
Figure 4J:
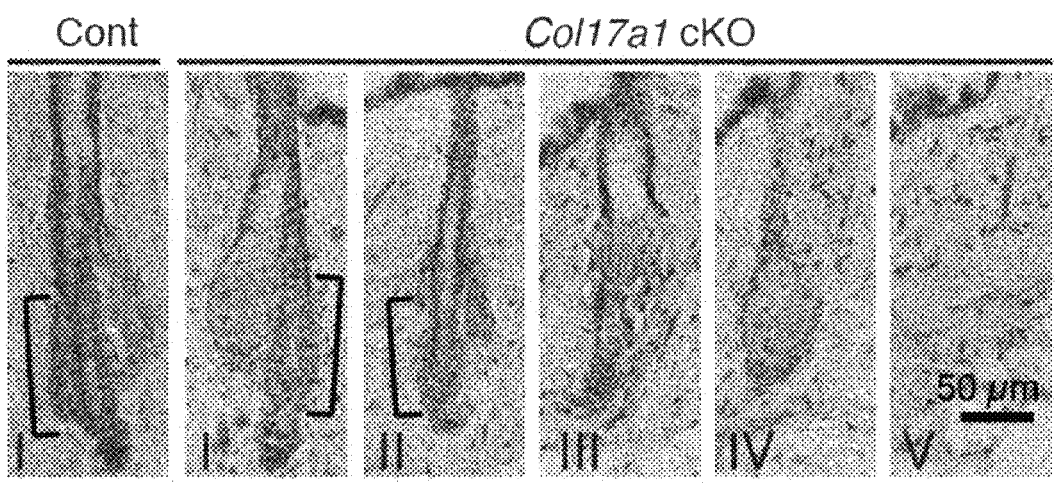
FIG. 4J It is a photo showing staging of the representative miniaturized hair follicles in COL17A1 cKO mice that morphologically show similar philological aging.
Figure 4K:
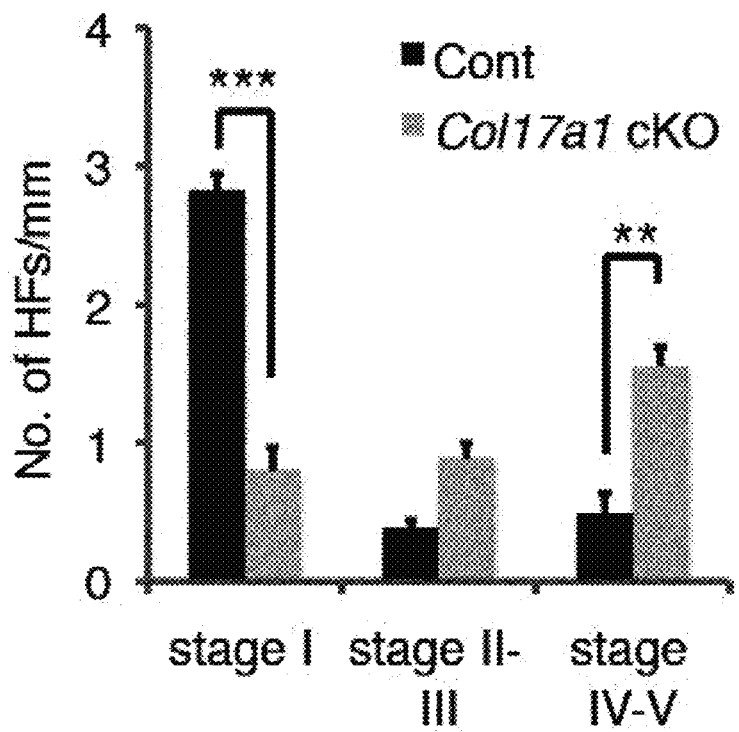
FIG. 4K It is a graph showing the number of each hair follicle stage per mm.
Figure 4L:
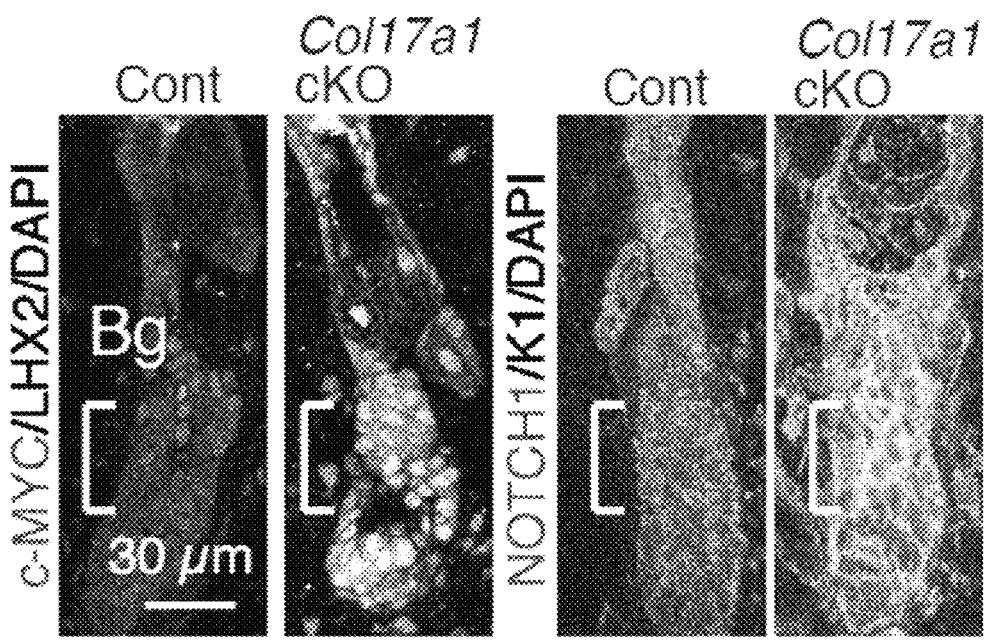
FIG. 4L They are immunostaining images for c-MYC and LHX2 or NOTCH1 and Keratin 1 in the control and in COL17A1 cKO mice at 12 weeks of age after hair cycling induction.
Figure 4M:
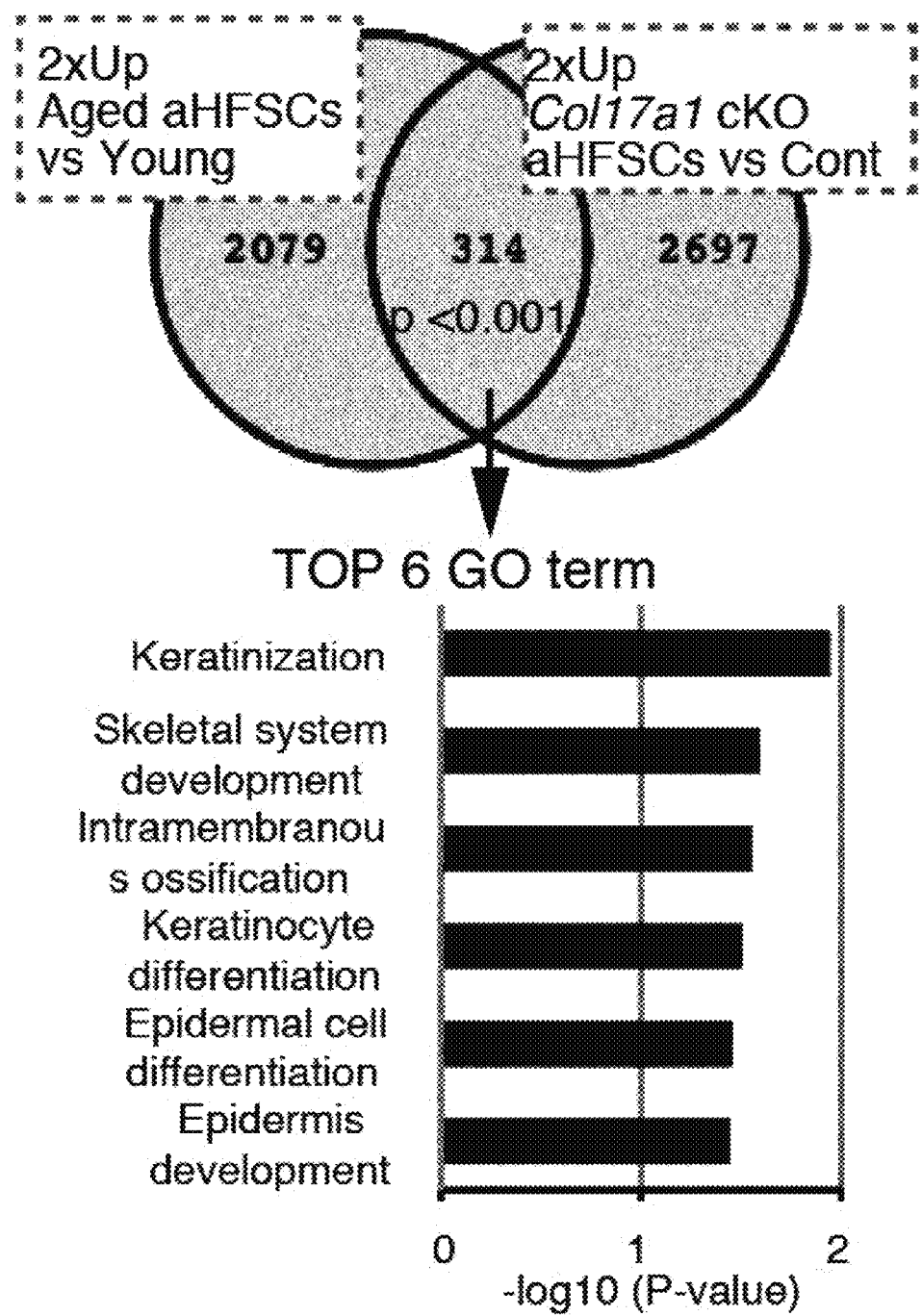
FIG. 4M It is a Venn diagram showing overlap between ≥2-fold increased genes in aged versus young mice and ≥2-fold increased genes in the control versus COL17a1 cKO mice.
Figure 4N:
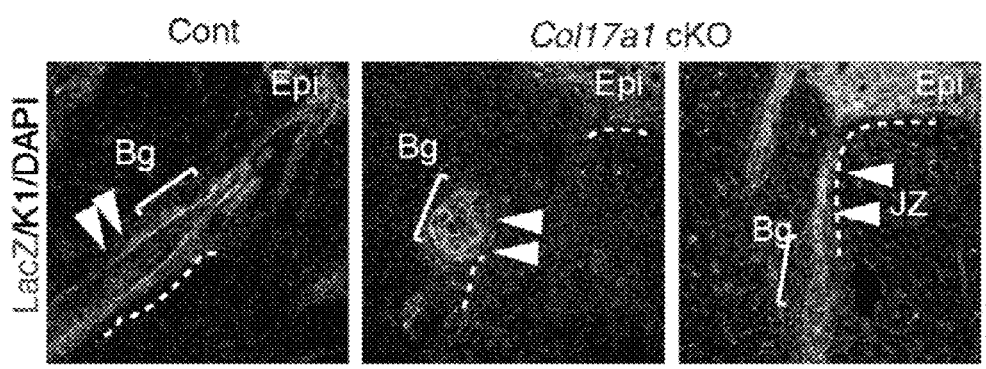
FIG. 4N It is a photo showing genetic fate analysis of LacZ-labeled hair follicle stem cells with COL17A1 deficiency.

Example 4: DNA Damage Response-Induced Proteolysis of COL17A1 in Hair Follicle Stem Cells (HFSC) Induces Dynamic Hair Follicle Miniaturization Through Epidermal Differentiation FIGS. 4A to 4C show aging or DNA damage response-induced COL17A1 proteolysis by ELANE. FIG. 4A shows immunostaining images for COL17A1 and ELANE in the hair follicle bulges of young (8-week-old), presenile (12 to 16-month-old), and aged (27-month-old) mice. Three mice (N=3) were used for each group. This analysis shows that ELANE was induced ectopically in aged hair follicle stem cells, while it was not detected in young hair follicle stem cells. Examples of proteases other than ELANE are ADAM (a disintegrin and metalloprotease) and MMP (matrix metalloproteinase). Accordingly, inhibitors of these proteases may be used as active ingredients in the present invention. FIG. 4B shows a quantitative analysis of fluorescence intensity of ELANE in the bulges and in the epidermis of 8-week-old, 12- to 16-month-old, and 27-month-old mice. Immunohistochemistry analysis shows that ELANE was significantly abnormally induced in about 40% of the bulge areas in 16-month-old hair follicles, and 60% in 24-month-old hair follicles. FIG. 4C shows immunostaining images of COL17A1, ELANE, SOX9 and Keratin 15 in the hair follicle bulges 12 hours, 1 day, and 7 days after 10-Gy irradiation. "7d" indicates typical hair follicles that have lost COL17A1 expression and other stem cell markers with ELANE induction, whereas "7d R" indicates typical hair follicles that have restored or maintained original stem cell marker expression at 7 days after 10-Gy irradiation. FIG. 4D shows Western-blot analysis of primary keratinocytes. The ELANE-treated primary keratinocytes shows that the 180 kD COL17A1 and its shed form of the 120 kD ectodomain were both quickly degraded by ELANE in vitro. COL17A1 was degraded in a dose-dependent manner 2 hours after adding ELANE or its inhibition factor A1AT. The degradation was completely suppressed by the protease inhibitor α1-antitrypsin (A1AT), and this strongly suggests that efficient proteolysis of COL17A1 by ELANE induced in hair follicle stem cells in response to DNA damage. FIG. 4E shows immunofluorescence images of 53BP1 and γ-H2AX foci in COL17A1+ bulges from young (8-week-old) and aged (25-month-old) mice. The foci were seen in the COL17A1-weakly positive area. FIG. 4F is a graph showing the number of 53BP1 foci in the COL17A1-weakly positive and COL17A1-positive areas in the bulge areas of 8-week-old and 25-month-old mice. 53BPI foci were significantly observed in the COL17A1-weakly positive area in the 25-month-old bulge regions. FIGS. 4G to 4M show analysis results of hair follicle stem cell-specific COL17A1 deficient (COL17AlcKO) mice. FIG. 4G is a photo of hair coats on the backs of control and Col17a1 cKO mice at 8.5 months of age. Hair loss and graying not seen in the control mice after depilation were seen in the COL17A1 cKO mice. FIG. 4H shows histological images of the control and COL17A1 cKO mice. Miniaturization of hair follicles was found in a COL17A1 cKO mouse (arrows). FIG. 4I is a graph showing the number of hair follicles per mm. FIG. 4J shows staging of the representative miniaturized hair follicles in COL17A1 cKO mice that morphologically show similar philological aging. FIG. 4K is a graph showing the number of each hair follicle stage per mm. In COL17A1 cKO mice, hair follicle miniaturization was seen from a young age in weeks. FIGS. 4L to 4M show induction of epidermal differentiation concomitant with the up-regulation of c-MYC and NOTCH1 expression by COL17A1 cKO deficiency. FIG. 4L shows immunostaining images for c-MYC and LHX2 or NOTCH1 and Keratin 1 in the control and in COL17A1 cKO mice at 12 weeks of age after hair cycling induction. c-MYC expression was ectopically induced in the LHX2+ bulge area of COL17A1 cKO mice. NOTCH1+ Keratin 1+ cells were found in the bulge area of COL17A1 cKO mice. FIG. 4M is a Venn diagram showing overlap between ≥2-fold increased genes in aged versus young mice and ≥2-fold increased genes in the control versus COL17A1 cKO mice. The gene ontology analysis was carried out for the common genes, and the ontology of "epidermal differentiation" and "keratinization" was detected among the top 6. FIG. 4N shows genetic fate analysis of LacZ-labeled hair follicle stem cells with COL17A1 deficiency. Keratin 1+ LacZ+ hair follicle stem cell-derived cells appear ectopically in the junctional zone and in the epidermis in Col17a1 cKO mice.

Figure 5A:
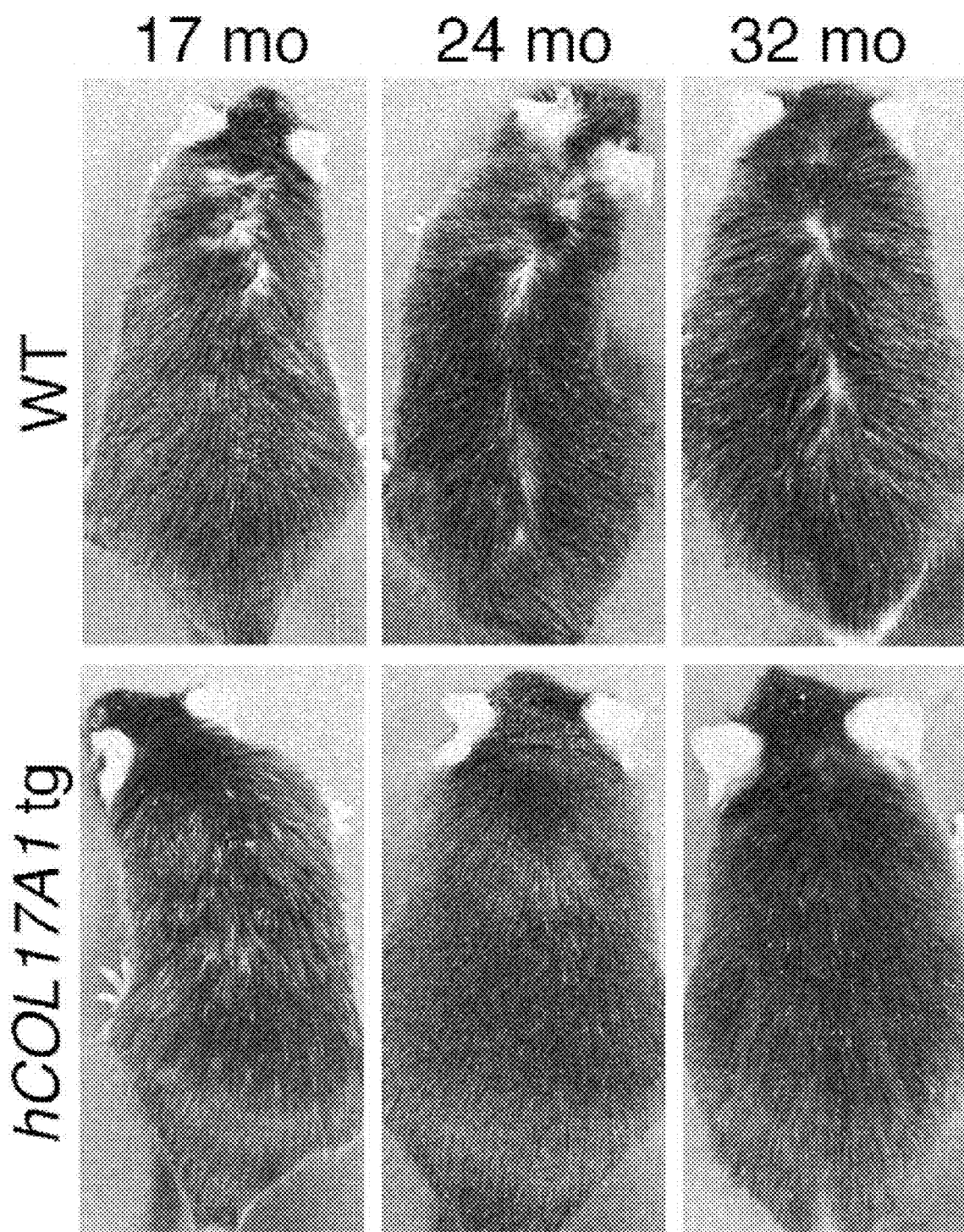
FIG. 5A They are photos of hair coats on the backs of wild-type and human COL17A1 transgenic (hCOL17A1 tg) mice at 17 months, 24 months, and 32 months of age.
Figure 5B:
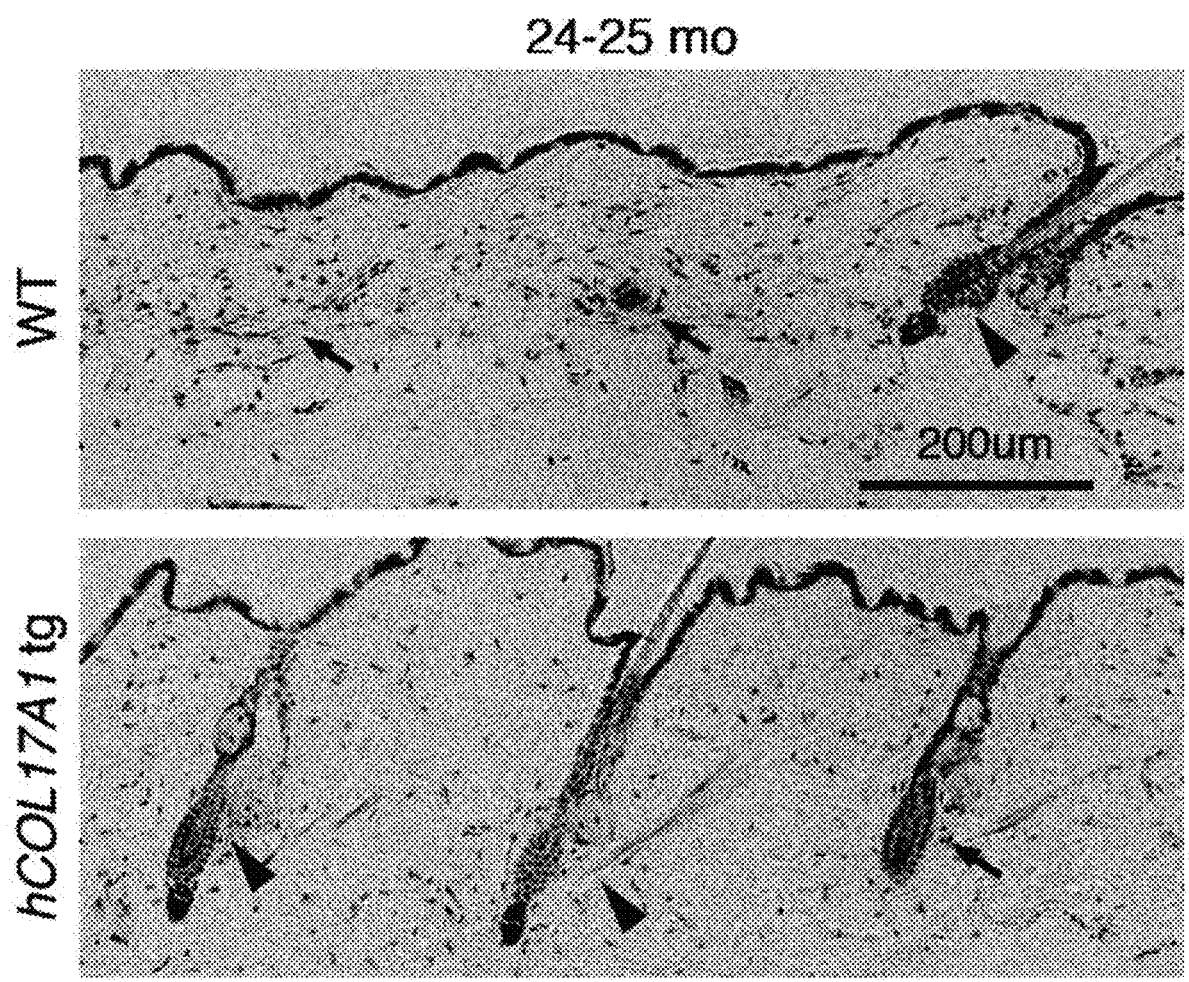
FIG. 5B They are histological images of wild-type mice and hCOL17A1 tg mice at 24 to 25 months of age.
Figure 5C:
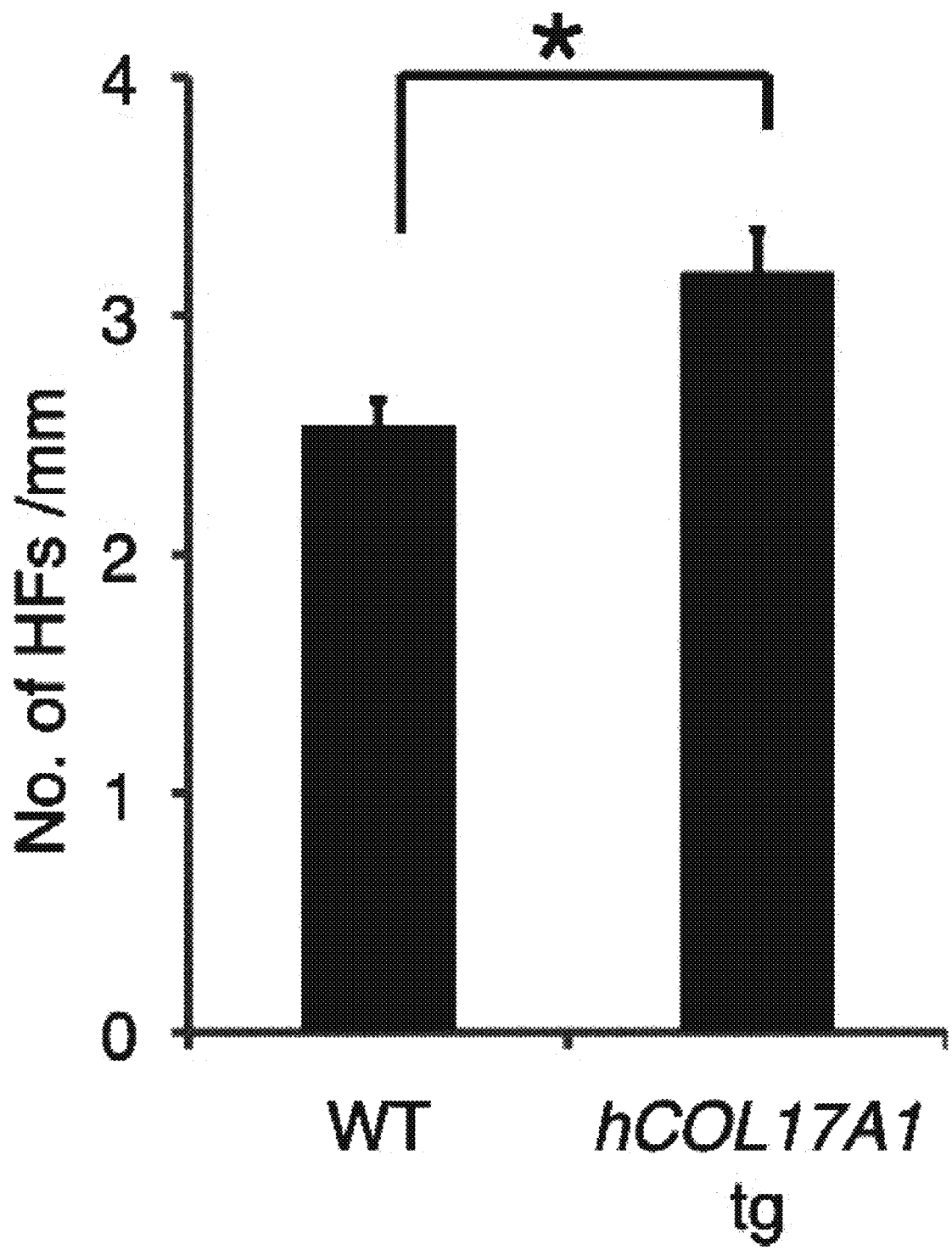
FIG. 5C It is a graph showing hair follicle number per mm in wild-type mice and hCol17a1 tg mice at 24 to 25 months of age.
Figure 5D:
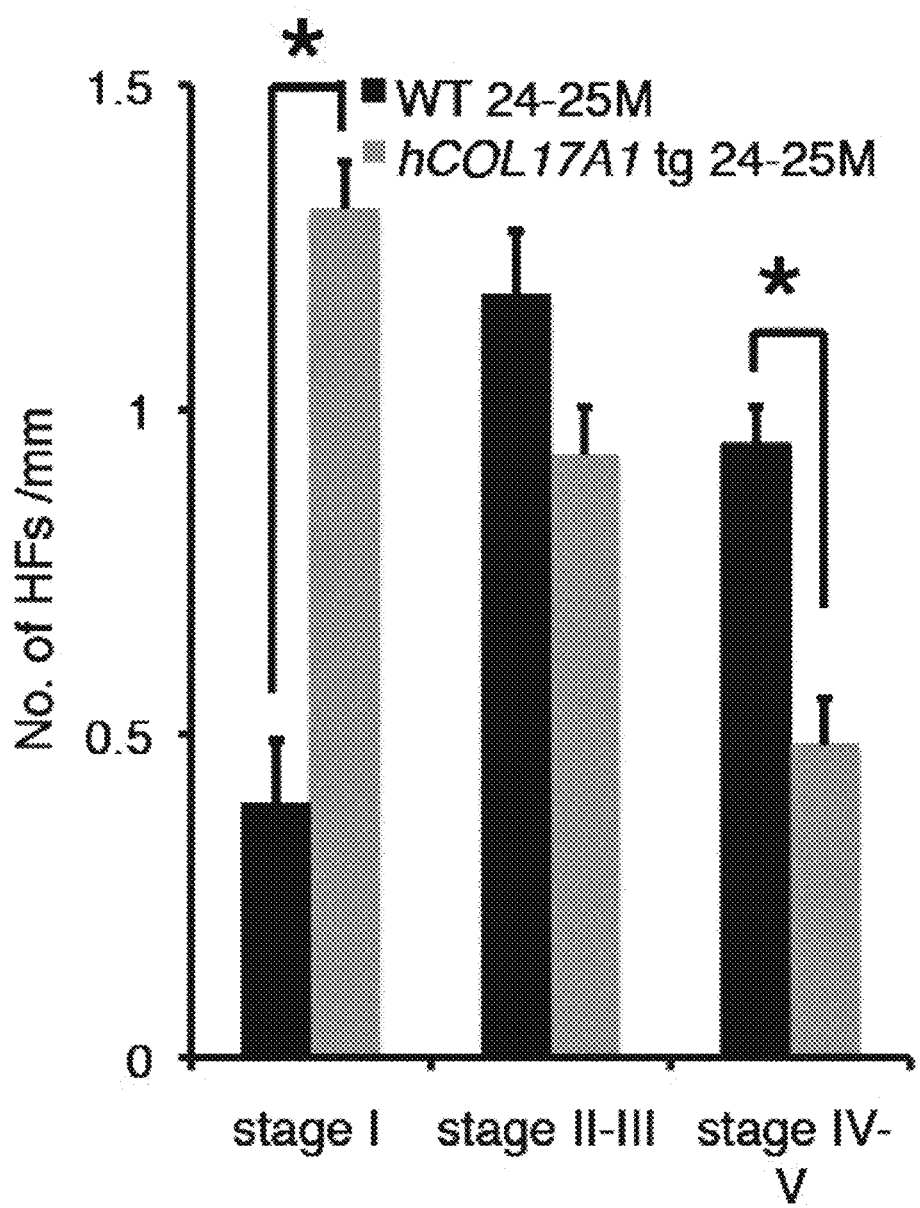
FIG. 5D It is a graph showing the number of hair follicles at each hair follicle stage per mm in wild-type mice and hCOL17A1 tg mice at 24 to 25 months of age.
Figure 5E:
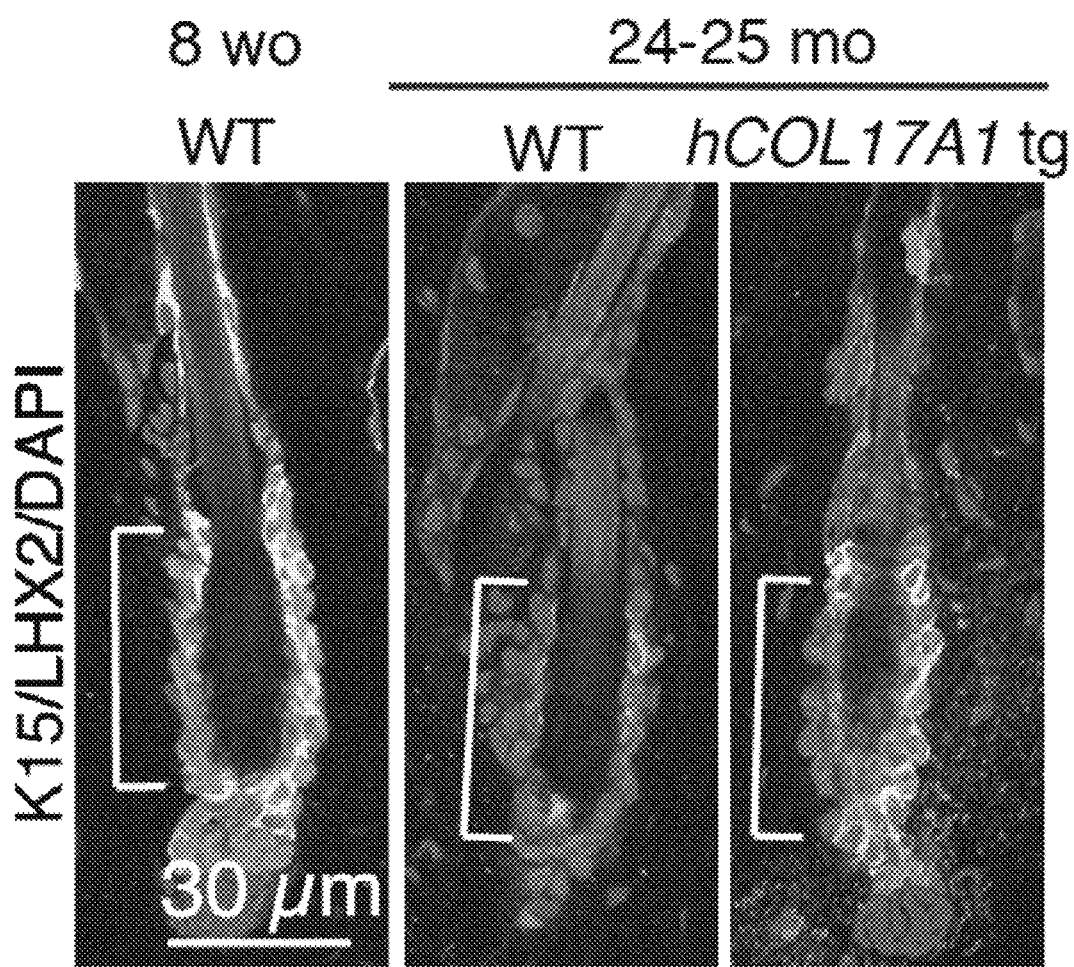
FIG. 5E They are staining images with hair follicle stem cell markers, Keratin 15 and LHX2, in wild-type mice and hCOL17A1 tg mice at 24 to 25 months of age.
Figure 5F:
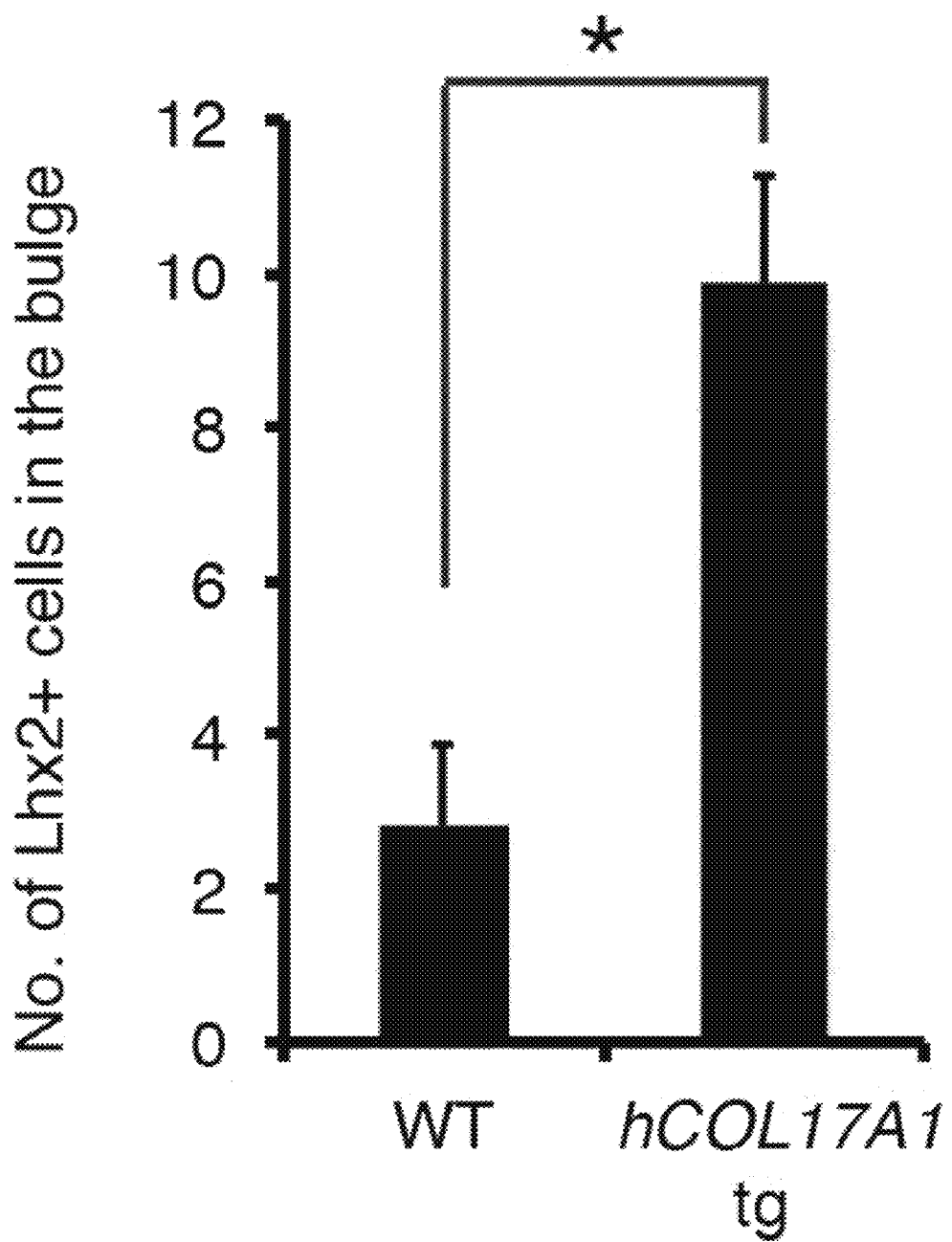
FIG. 5F It is a graph showing a quantitative analysis of the number of LHX2+ nuclei in the bulge by immunostaining.

Example 5: Forced Expression of COL17A1 in Hair Follicle Stem Cells Protects their Depletion and Hair Follicle Aging FIG. 5A shows photos of hair coats on the backs of wild-type and human COL17A1 transgenic (hCOL17A1 tg) mice at 17 months, 24 months, and 32 months of age. The hair loss seen in the wild type was alleviated in hCOL17A1 tg mice. FIG. 5B shows histological images of wild-type mice and hCOL17A1 tg mice at 24 to 25 months of age. Arrows indicate miniaturized hair follicles at Stages III and IV. Arrowheads show hair follicles at Stage I. FIG. 5C is a graph showing hair follicle number per mm in wild-type mice and hCol17a1 tg mice at 24 to 25 months of age. Three mice (N=3) for each group. FIG. 5D is a graph showing the number of hair follicles at each hair follicle stage per mm in wild-type mice and hCOL17A1 tg mice at 24 to 25 months of age. FIG. 5E shows staining images with hair follicle stem cell markers, Keratin 15 and LHX2, in wild-type mice and hCOL17A1 tg mice at 24 to 25 months of age. The reduction of hair follicle stem cell marker expression seen in the wild-type mice was rescued in hCOL17A1 tg mice. FIG. 5F shows a quantitative analysis of the number of LHX2+ nuclei in the bulge by immunostaining. The reduction of LHX2+ cells by aging was rescued in hCOL17A1 tg mice.

Figure 6A:
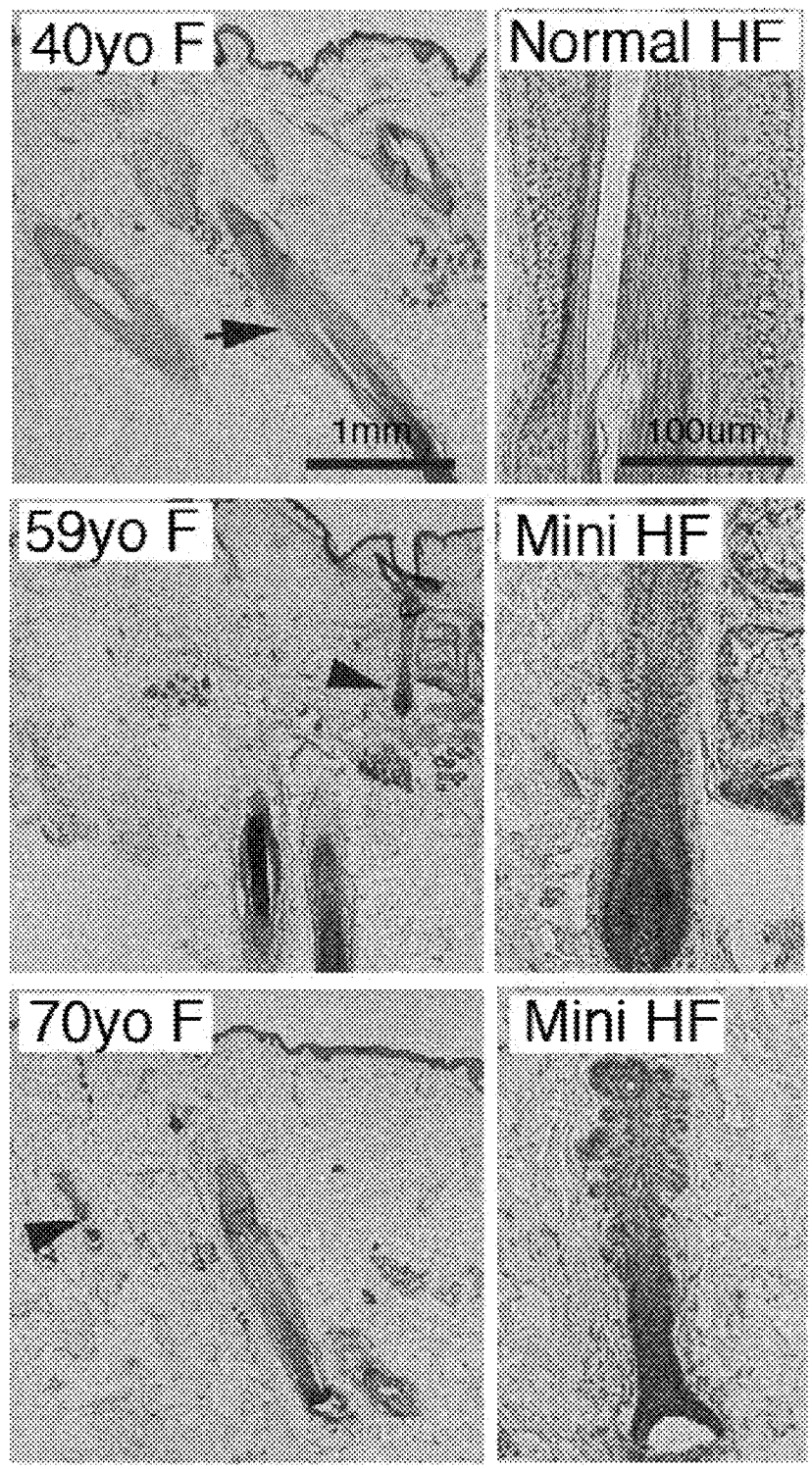
FIG. 6A They are hematoxylin and eosin stained images of human scalps from aged (59- and 70-year-old) and from middle-aged (40-year-old) women.
Figure 6B:
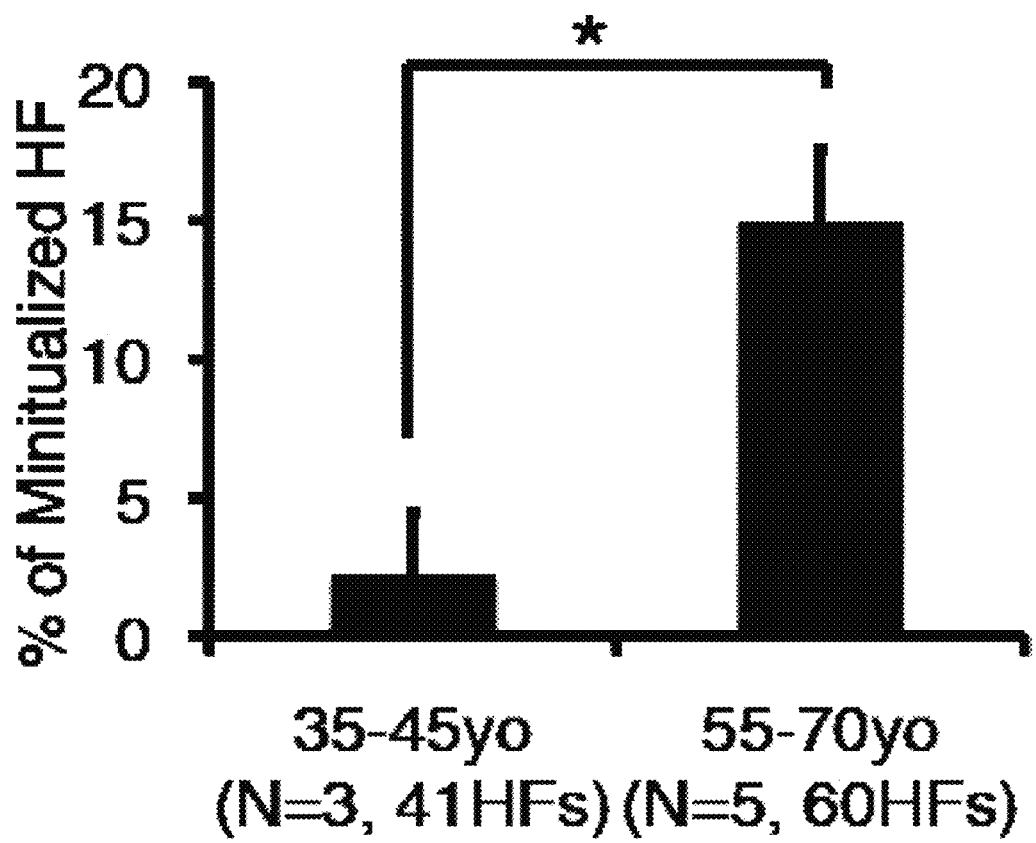
FIG. 6B It is a graph showing percentage of miniaturized hair follicles.
Figure 6C:
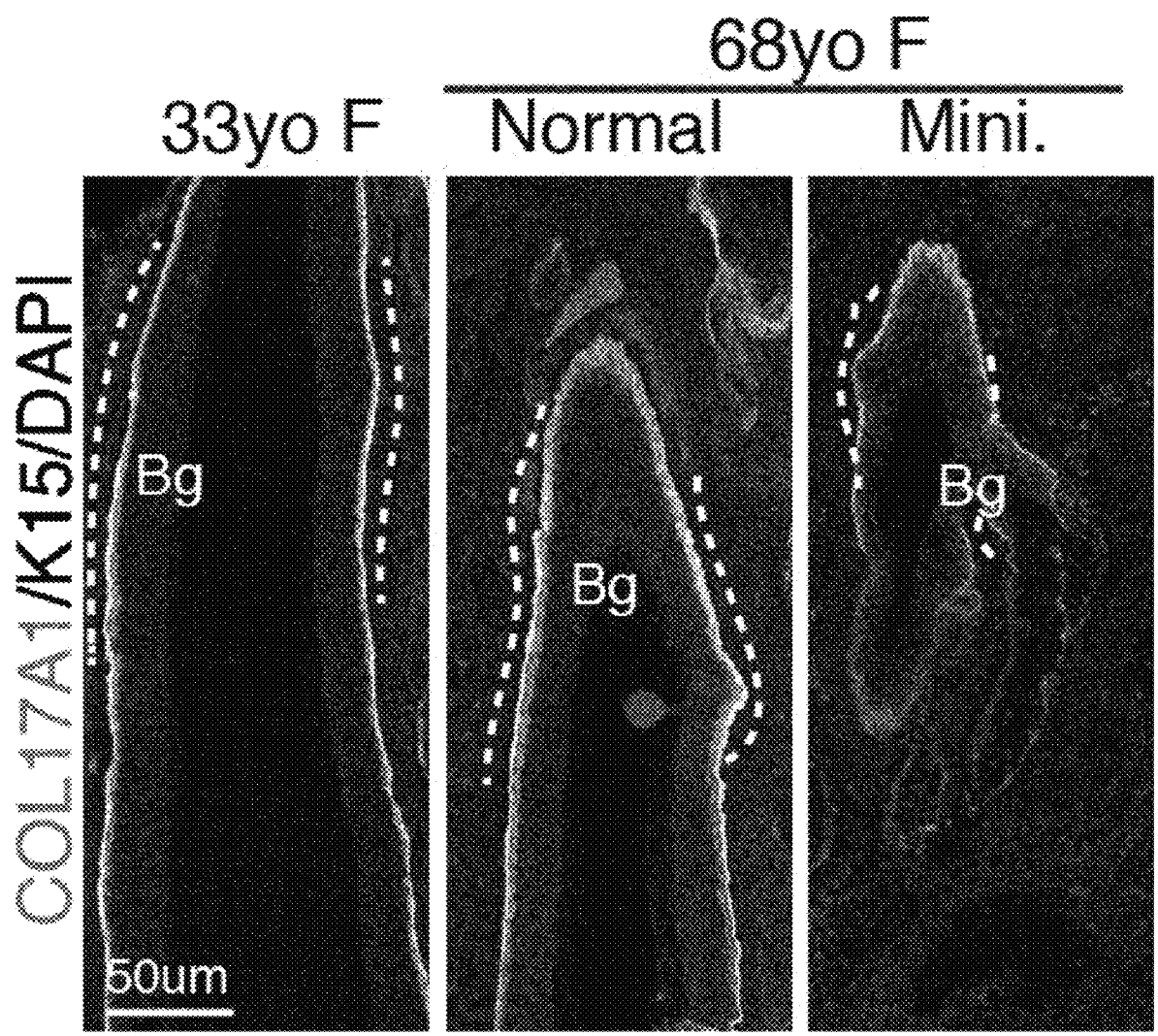
FIG. 6C It is an immunostaining image showing an expression analysis of hair follicle stem cell markers in young and aged hair follicles.
Figure 6D:
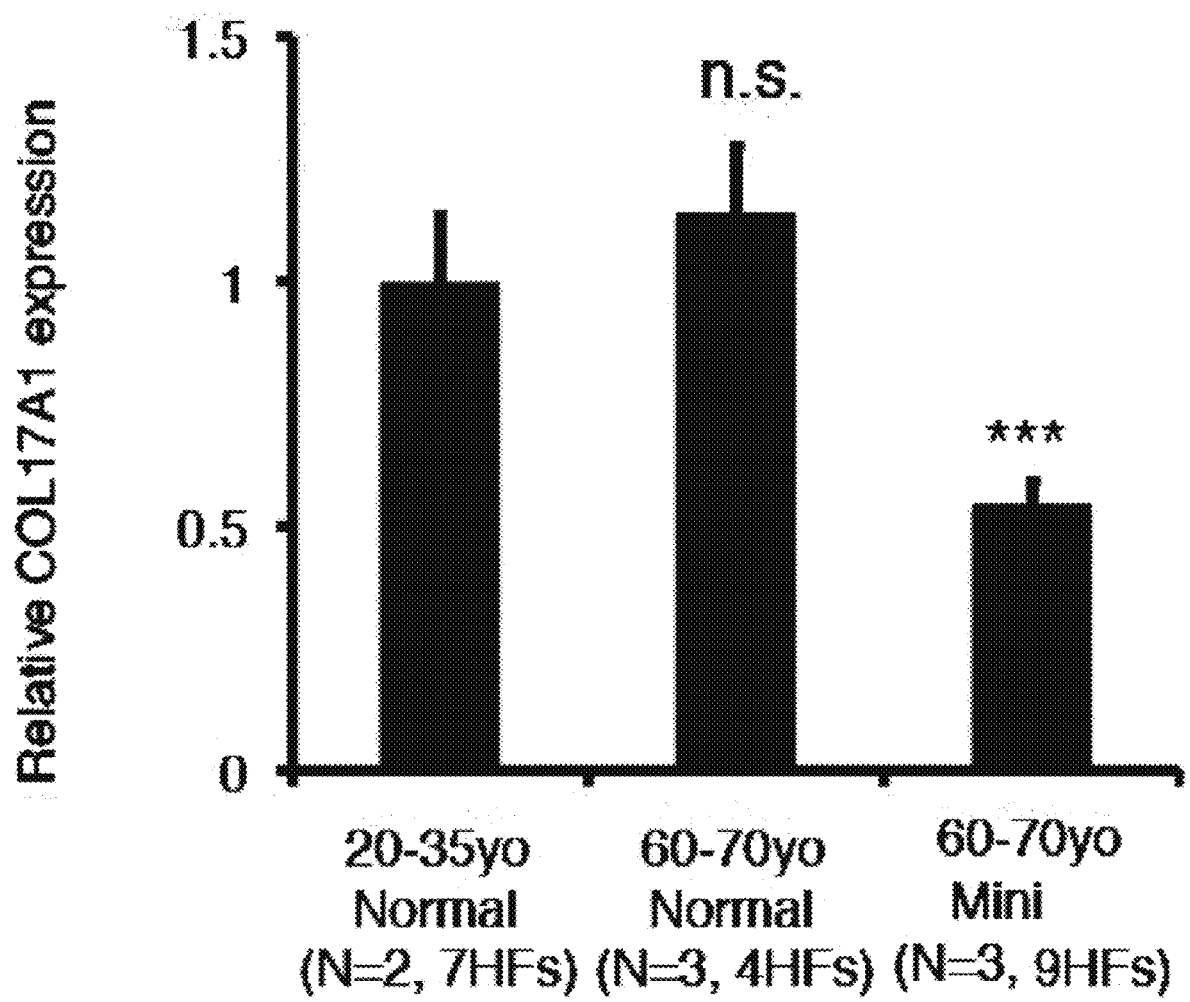
FIG. 6D It is a graph showing a quantitative analysis of fluorescence intensities for human COL17A1.
Figure 6E:
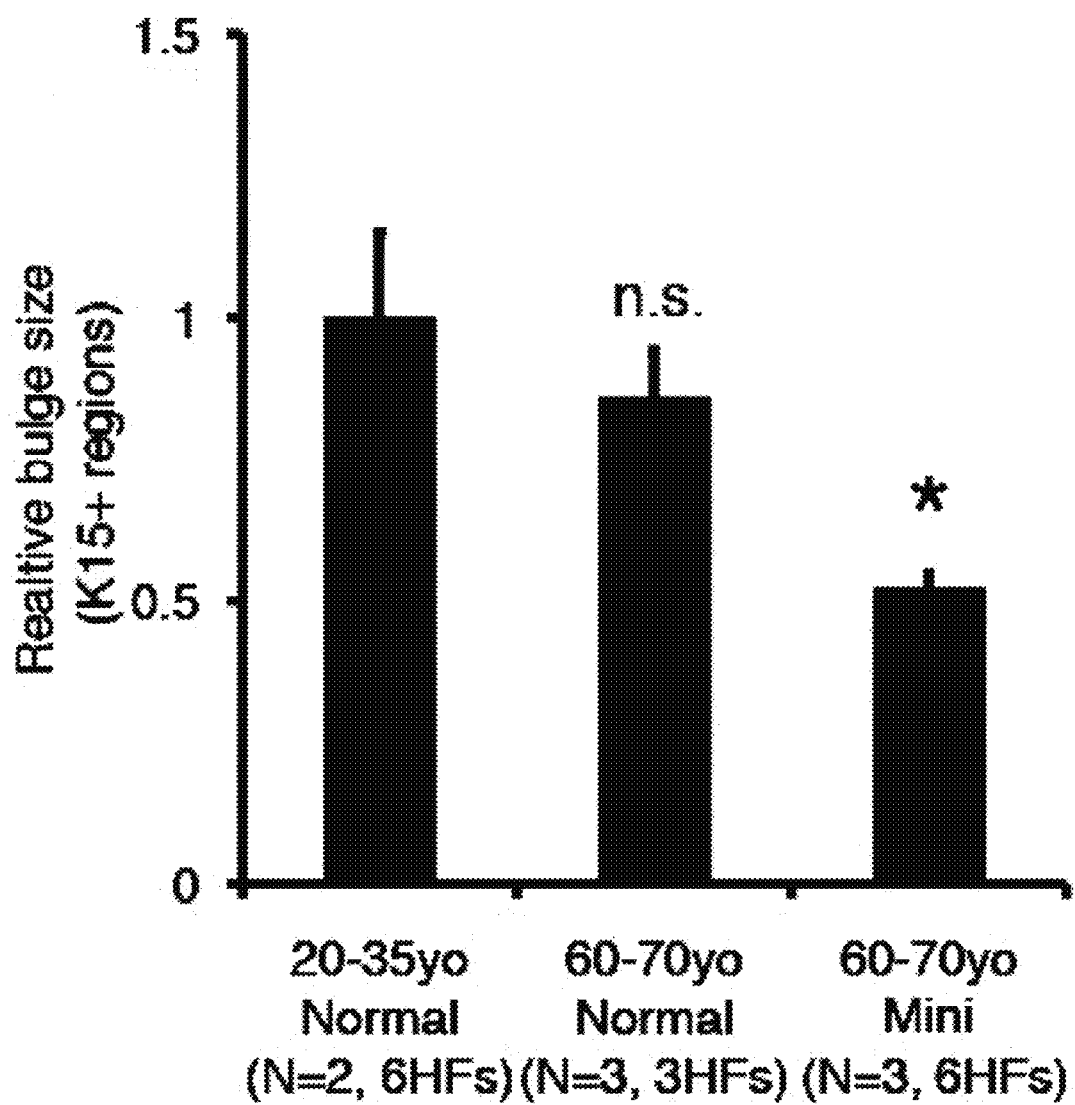
FIG. 6E It shows a size analysis of Keratin 15+ bulge area.
Figure 6F:
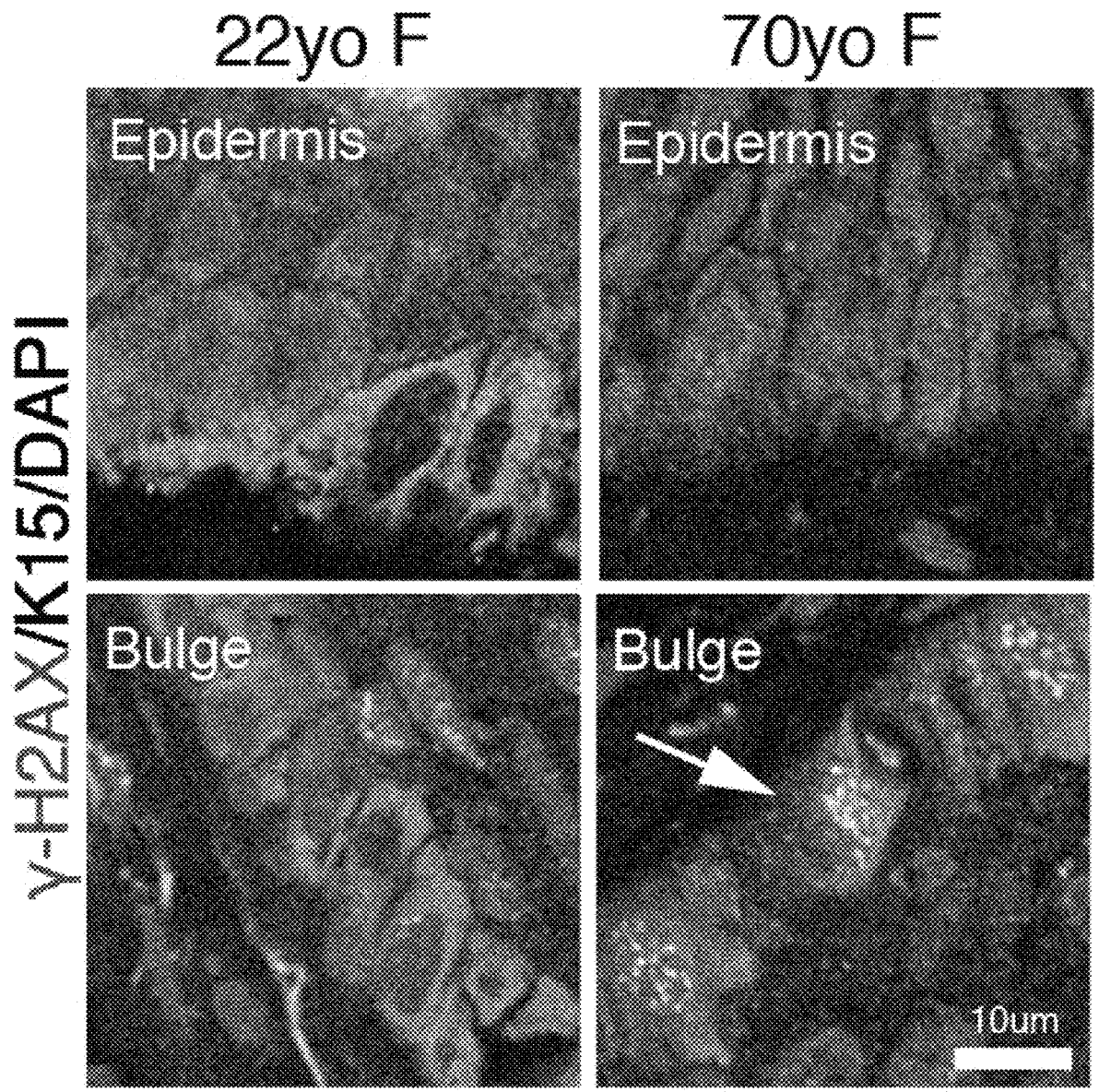
FIG. 6F It is a photo showing γ-H2AX foci formation in Keratin 15+ epidermis and bulges of human scalps at each age.
Figure 6G:
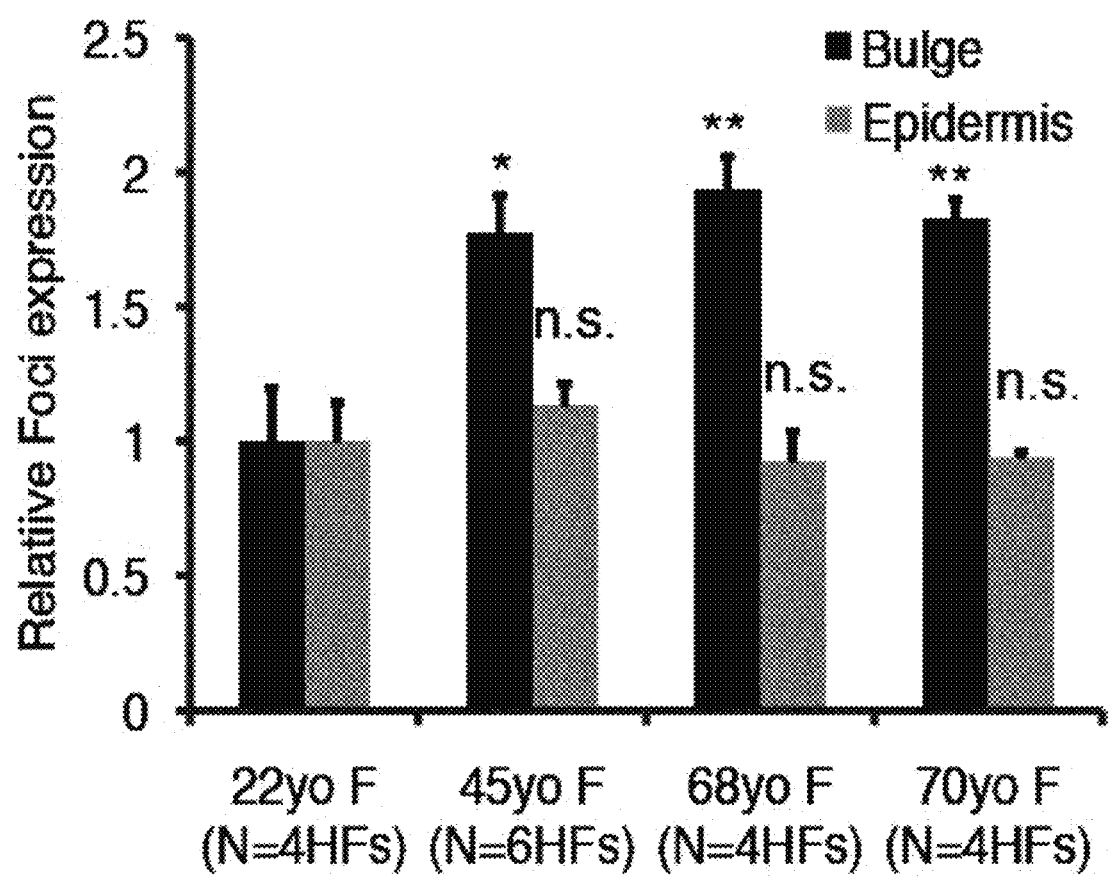
FIG. 6G It is a graph showing a quantitative analysis of γ-H2AX foci fluorescence intensity.
Figure 6H:
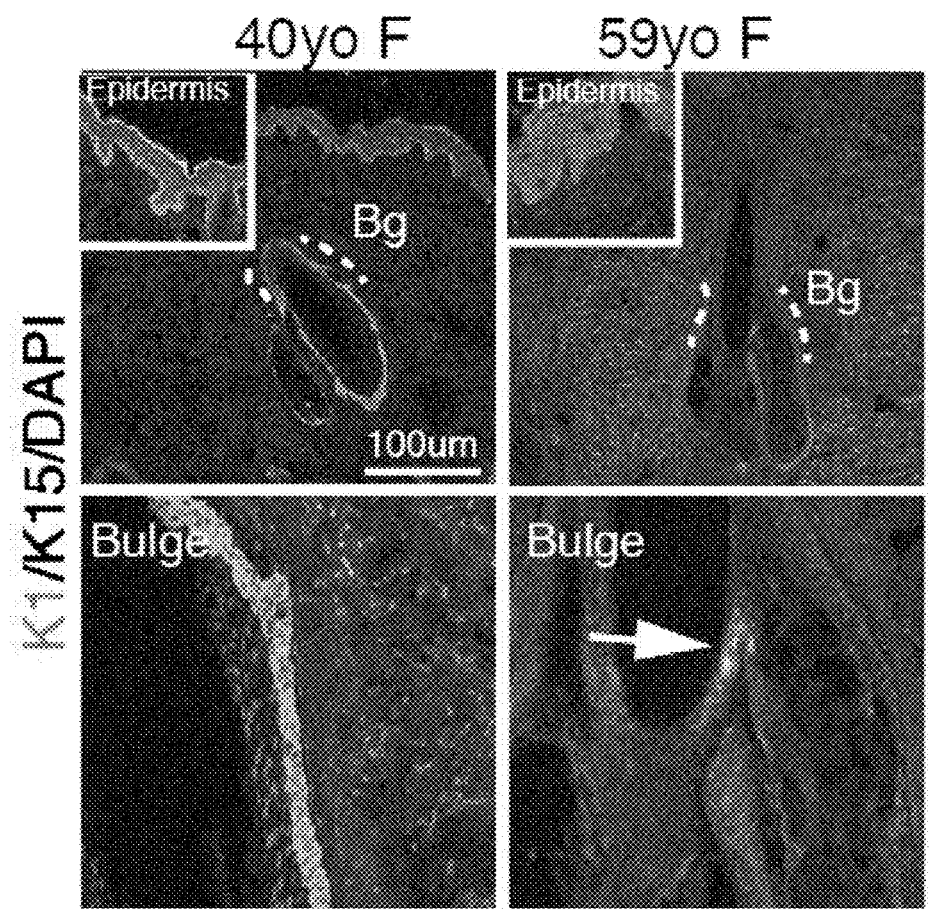
FIG. 6H It is a photo showing ectopic epidermal differentiation in the human bulge area.

Example 6: Observation of Mouse Hair Follicle Miniaturization with Reduction of COL17A1 Expression on Human Scalp FIG. 6A shows hematoxylin and eosin stained images of human scalps from aged (59- and 70-year-old) and middle-aged (40-year-old) women. Arrows indicate normal hair follicles, and arrowheads indicate miniaturized hair follicles. FIG. 6B is a graph showing percentage of miniaturized hair follicles. Miniaturized hair follicles were significantly increased in aged (55- to 70-year-old) hair follicles. FIG. 6C shows an expression analysis of hair follicle stem cell markers in young and aged hair follicles. These are immunostaining images of human COL17A1 and Keratin 15 in normal or miniaturized hair follicles in human scalps from 33-year-old and 68-year-old women. FIG. 6D is a graph showing a quantitative analysis of fluorescence intensities for human COL17A1. Human COL17A1 expression was significantly down-regulated in aged miniaturized hair follicles. FIG. 6E shows a size analysis of Keratin 15+ bulge area. The bulge size was significantly diminished in aged (60- to 70-year-old) miniaturized hair follicles. FIG. 6F shows γ-H2AX foci formation in Keratin 15+ epidermis and bulges of human scalps at each age. FIG. 6G shows a quantitative analysis of γ-H2AX foci fluorescence intensity. The fluorescence level was significantly increased in the aged (40- to 70-year-old) bulge areas but not in the epidermal areas. FIG. 6H shows ectopic epidermal differentiation in the human bulge area. Representative immunostaining images of human hair follicles for Keratin 1 and Keratin 15 are shown. Keratin 1 expression was induced in the 59-year-old bulge area.

Example 7: Mechanisms for Hair Follicle Aging

FIGS. 7A and 7B show a schematic diagram for the mechanism of hair follicle aging. The hair follicle stem cell pool is maintained in a long quiescent state during aging (Stage Ia). Hair follicle stem cells demonstrating DNA damage response trigger COL17A1 proteolysis through induction of ELANE protease (Stage Ib). Those hair follicle stem cells with weakly positive COL17A1 expression lose their stem cell signature and induce epidermal differentiation in the niche. Those "aged" hair follicle stem cells migrate up toward the epidermis through the junctional zone with hair cycling. They terminally differentiate into cornified keratinocytes to be eliminated from the skin surface, thereby causing the stepwise miniaturization of hair follicles and hair thinning and loss.

Example 8: Induction of COL17A1 Expression by Apocynin

Figure 8:
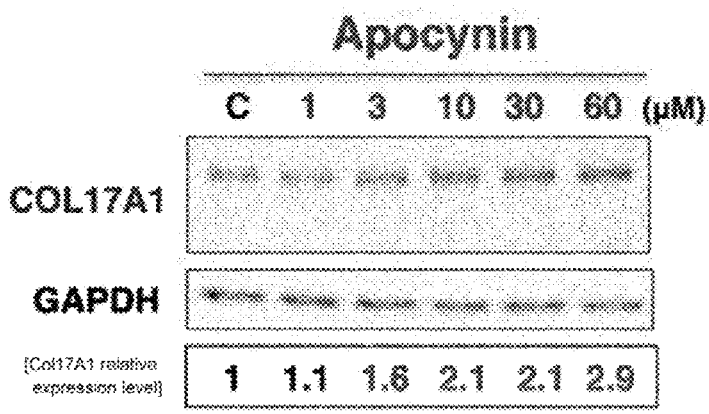
FIG. 8 It is an electrophoresis photo showing induction of COL17A1 by apocynin.

HaCat cells (human epidermal keratinocyte strain) were seeded in 10% FBS-containing D-MEM medium in a 6-well plate at $1\times10^5$ cells per well, and apocynin was added to be 1-60 µM. After 48 hours of culturing, an anti-Col17A1 antibody was used as the primary antibody, and Western blotting was carried out. An anti-GAPDH antibody was used as the internal control. The 180 KDa band of Col17A1 and the internal control GAPDH band were quantified for their densities using an LAS-3000 luminescence image analyzer. As a result, an increase of Col17A1 was observed along with the increase of apocynin, and it was understood that apocynin has an effect of increasing Col17A1 expression (FIG. 8).

Example 9: Induction of COL17A1 Expression by Ascorbic Acid

Figure 9:
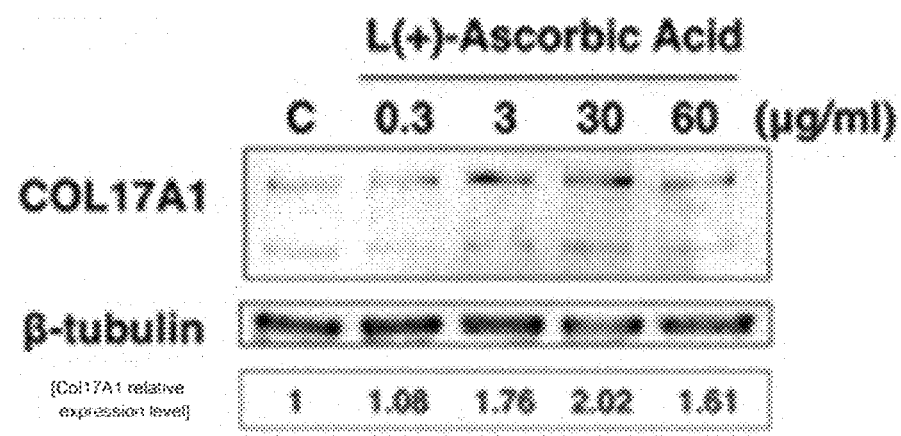
FIG. 9 It is an electrophoresis photo showing induction of COL17A1 by acorbic acid.

HaCat cells (human epidermal keratinocyte strain) were seeded in 10% FBS-containing D-MEM medium in a 6-well plate at $1\times10^5$ cells per well, and ascorbic acid (Wako Pure Chemical Industries, Ltd.) was added to be 0.3-60 jag/ml. After 48 hours of culturing, an anti-Col17A1 antibody was used as the primary antibody, and Western blotting was carried out. An anti-β-tubulin antibody was used as the internal control. The 180 KDa band of Col17A1 and the internal control β-tubulin band were quantified for their densities using an LAS-3000 luminescence image analyzer. As a result, an increase of Col17A1 was observed along with the increase of ascorbic acid, and it was understood that ascorbic acid has an effect of increasing Col17A1 expression (FIG. 9).

Example 10: Induction of COL17A1 Expression by MMP Inhibitor Marimastat

Figure 10:
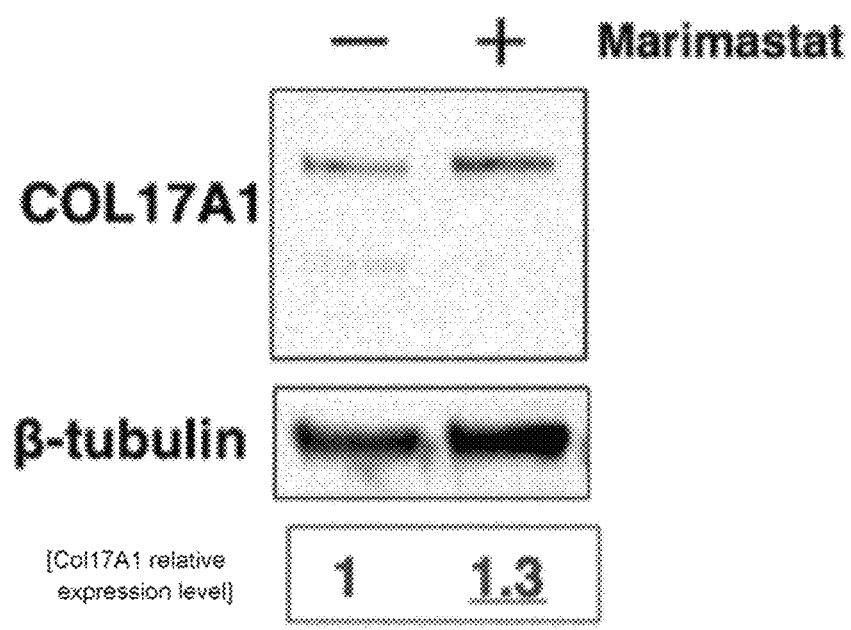
FIG. 10 It is an electrophoresis photo showing induction of COL17A1 by Marimastat.

HaCat cells (human epidermal keratinocyte strain) were seeded in 10% FBS-containing D-MEM medium in a 6-well plate at $1\times10^5$ cells per well, and Marimastat (MMP inhibitor) was added to be 3 µM. After 48 hours of culturing, an anti-Col17A1 antibody was used as the primary antibody, and Western blotting was carried out. An anti-β-tubulin antibody was used as the internal control. The 180 KDa band of Col17A1 and the internal control β-tubulin band were quantified for their densities using an LAS-3000 luminescence image analyzer. As a result, an increase of Col17A1 was observed by addition of Marimastat, and it was understood that Marimastat has an effect of increasing Col17A1 expression (FIG. 10).

Example 11: Hair-Increasing Effect of Apocynin in Aged Mice

Figure 11:
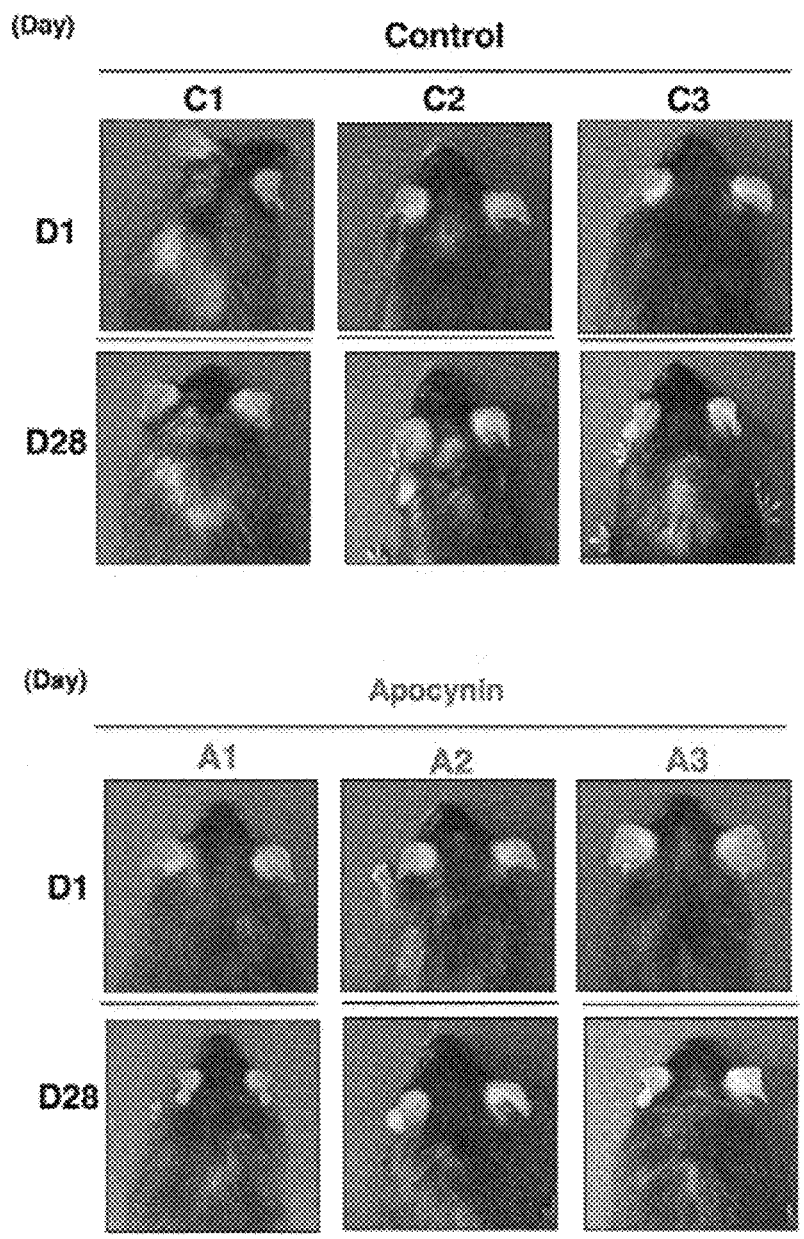
FIG. 11 It is a photo showing the hair-increasing effect of apocynin in aged mice.

Apocynin (A727200; Tront Research Chemicals) was adjusted to the concentration of 20 mM with DMSO, and 200 LM apocynin solution (1% apocynin 20 mM, 49% water, 50% ethanol) was prepared as the solution to be applied on mice. As the control solution, 1% DMSO (Sigma Aldrich), 49% water, 50% ethanol was prepared. After an anesthetic procedure was performed on five 27-month-old and one 26-month-old female C57BL/6NCrSlc mice, hair on the back of the neck was removed. The three mice in the control solution treatment group were applied with 100 µl of the control solution, and the apocynin solution treatment group with 100 µl of the 200 µM apocynin solution for 28 days. For the follow-ups, photo images of the representative first day (day 1) and the last day (day 28) are shown (FIG. 11). On day 28, the apocynin-administered group showed a significant hair growth effect compared to the control group.

Figure 12:
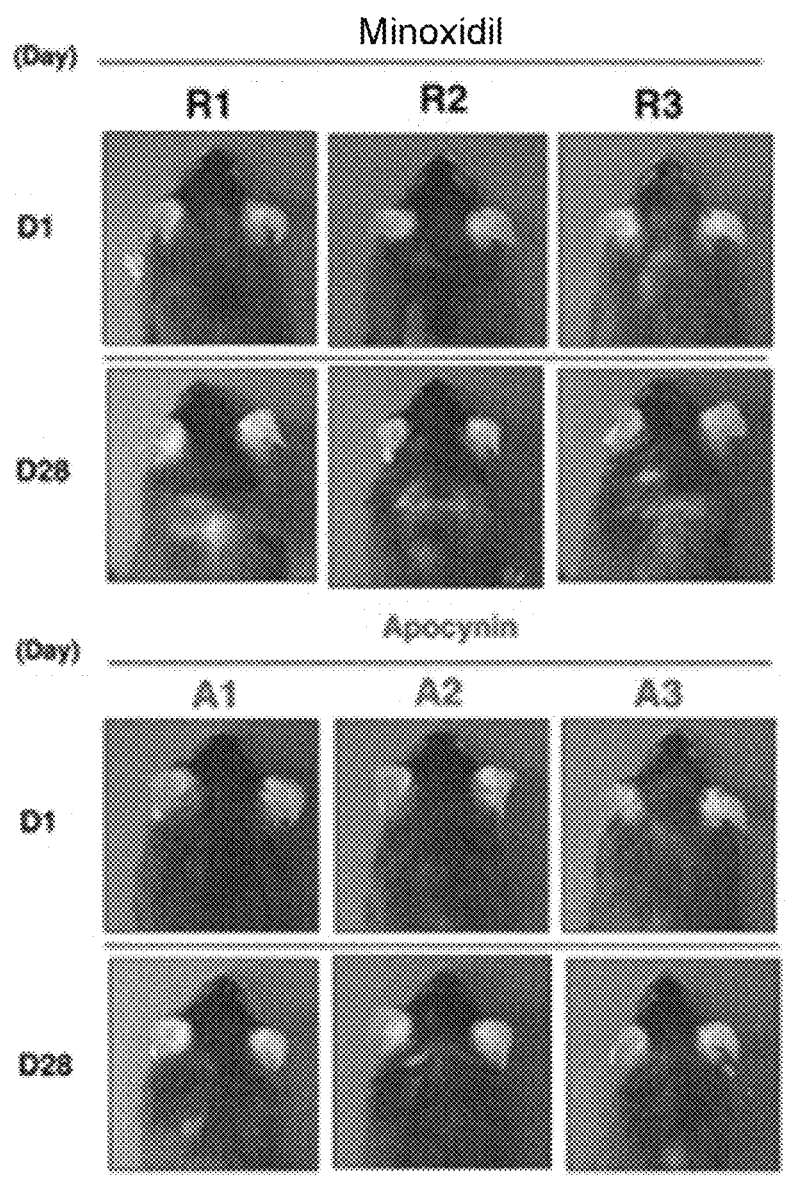
FIG. 12 It is a photo showing comparison of the hair-increasing effects of minoxidil (upper) and apocynin (lower) in aged mice.

Example 12: Comparison of the Hair-Increasing Effects of Apocynin and Minoxidil in Aged Mice Apocynin (A727200; Tront Research Chemicals) was adjusted to the concentration of 20 mM with DMSO, and 200 LM apocynin solution (1% apocynin 20 mM, 49% water, 50% ethanol) was prepared as the solution to be applied on mice. As the control solution, 1% DMSO (Sigma Aldrich), 49% water, 50% ethanol was prepared. For the minoxidil solution, Ri-UP X5 PLUS® (5 g/100 ml, Taisho Pharmaceutical Co., Ltd.) was used. After six 17-month-old female C57BL/6NCrSlc mice were anesthetized by inhalation of isoflurane (Pfizer), the hair on the back of the neck was removed. The three mice in the minoxidil treatment group were applied with 100 µl of minoxidil, and the apocynin treatment group with 100 µl of the 200 µM apocynin solution for 28 days. For the follow-ups, photo images of the representative first day (day 1) and the last day (day 28) are shown (FIG. 12). On day 14, the apocynin-administered group showed a significant hair growth effect compared to the minoxidil-administered group.

Example 13: Application Test of Sivelestat on the Back of Irradiated Mice

Figure 13:
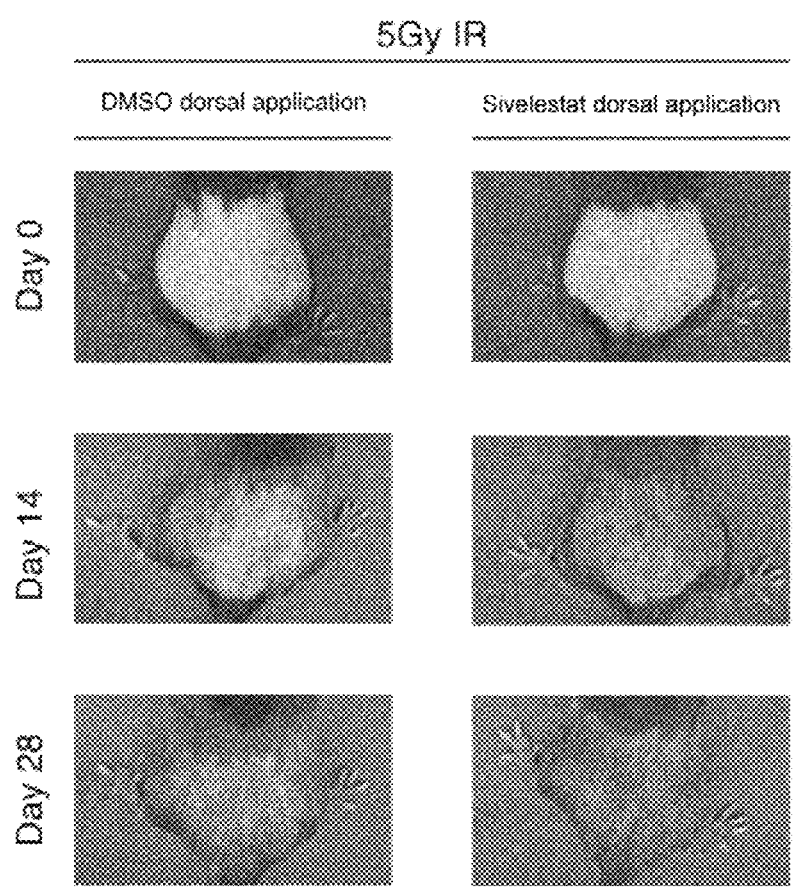
FIG. 13 It is a photo showing the effect of dorsal application of Sivelestat in irradiated mice.

The hair on the lower back of 7-week-old male C57BL/6NCrSlc mice was removed. Sivelestat was dissolved in DMSO to be 10 mg/ml and 125 µl (=1250 g) thereof was applied on the back of the sivelestat group mice. On the back of the control group mice, 125 µl of DMSO was applied. After application on the back, the skin of the two groups of mice (day 0) was irradiated with a low voltage radiation of 5 Gy using CABINET X-RAY SYSTEM (Faxitron X-ray Corporation). Up to day 4, the same medicinal agents described above were applied on the back once a day (for a total of 5 times), and weekly follow-ups were carried out after that. As a result, suppression of graying was seen 14 weeks and 28 weeks in the administered group after administration (FIG. 13). The hair had the tendency to grow faster in the administered group compared to the control group.

Example 14: Test of Intradermal Administration of Sivelestat in Irradiated Mice

The hair on the lower back of 7-week-old male C57BL/6NCrSlc mice was removed. Sivelestat was dissolved in DMSO to be 5 mg/ml and 200 µl (=1000 µg) thereof was administered intradermally on back of the sivelestat group mice. On the back of the control group mice, 200 µl of DMSO was administered intradermally. After intradermal administration, the skin of the two groups of mice (day 0) was irradiated with a low voltage radiation of 5 Gy using CABINET X-RAY SYSTEM (Faxitron X-ray corporation).

Figure 14:
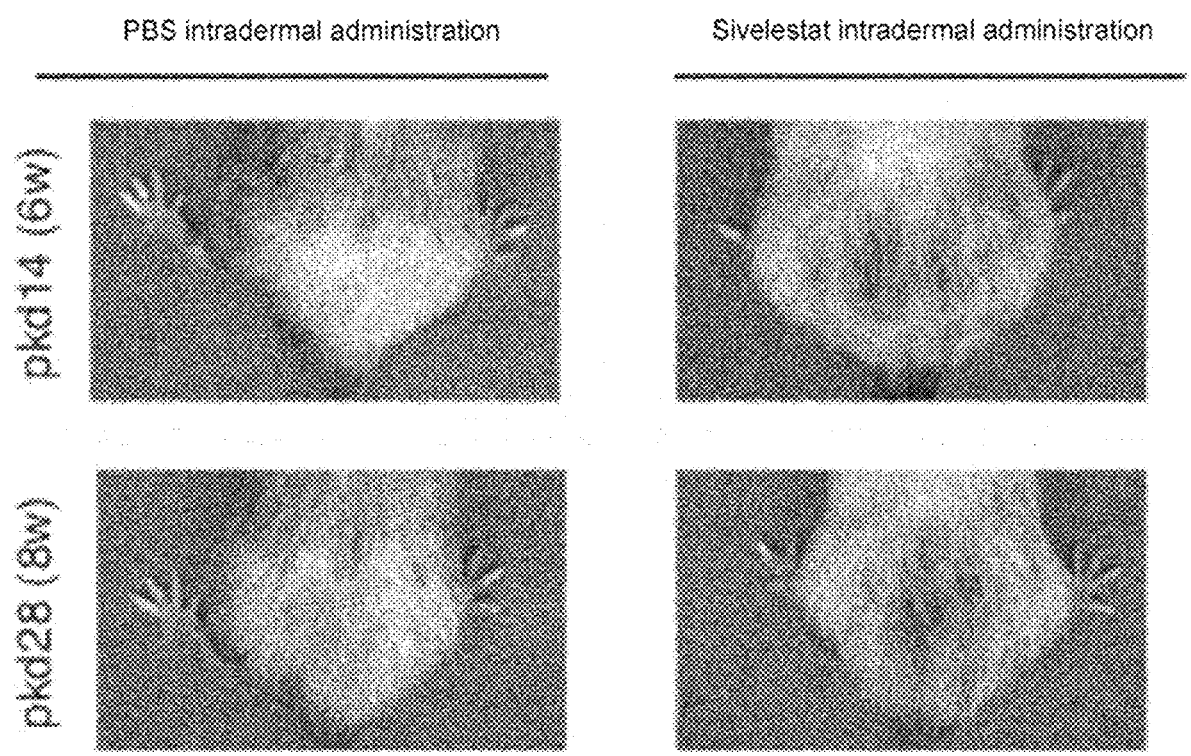
FIG. 14 It is a photo showing the effect of intradermal administration of Sivelestat in irradiated mice.

Up to day 4, the same medicinal agents described above were intradermally administered on the back once a day (for a total of 5 times), and weekly follow-ups were carried out after that. As a result, suppression of graying was seen 14 weeks and 28 weeks in the administered group after administration (FIG. 14). The hair had the tendency to grow more in the administered group compared to the control group.

The present specification shows the preferred embodiments of the present invention, and it is clear to those skilled in the art that such embodiments are provided simply for the purpose of exemplification. A skilled artisan may be able to make various transformations, and add modifications and substitutions without deviating from the present invention. It should be understood that the various alternative embodiments of invention described in the present specification may be used when practicing the present invention. Further, the contents described in all publications referred to in the present specification, including patents and patent application documents, should be construed as being incorporated the same as the contents clearly written in the present specification by their citation.

INDUSTRIAL APPLICABILITY

The inventors discovered that type XVII collagen (Col17A1) expression in aged mouse and human hair follicle stem cells is reduced, and that the expression of Col17A1 in mouse hair follicle stem cells is reduced as a result of Col17A1 degradation caused by irradiation. Further, they revealed that neutrophil elastase (ELANE) is involved in Col17A1 degradation. They confirmed that by forcedly expressing COL17A1 in mouse hair follicles and basal cells of the epidermis, aging-associated changes in hair follicle stem cells are suppressed and stem cells are maintained, which postpone changes in the hair follicles and the whole skin. Based on the above, COL17A1 expressed by hair follicle stem cells is thought to suppress aging-associated changes in hair follicles and skin with aging or X-ray radiation. For example, it should be understood by skilled artisans that using neutrophil elastase to suppress COL17A1 degradation may be applicable to the anti-aging of hair follicles and skin, suppression or improvement of graying, suppression or improvement of hair loss, and hair growth. There are few existing medicaments that suppress or improve hair loss or graying, and since their effects are insufficient, there is a high market demand.

The invention claimed is:

1. A method for suppressing or improving hair graying in a mammal, comprising administering to the mammal a stabilizing agent of type XVII collagen expression, wherein the stabilizing agent of type XVII collagen expression is selected from the group consisting of an MMP inhibitor, an NADPH oxidase inhibitor, an oxidation inhibitor, and an ADAM inhibitor.

2. The method according to claim 1, wherein the MMP inhibitor is selected from the group consisting of Marimastat, Batimastat, PD166793, Ro32-3555, WAY170523, UK370106, TIMP1, TIMP2, TIMP3, and TIMP4.

3. The method according to claim 1, wherein the NADPH oxidase inhibitor is selected from the group consisting of apocynin, AEBSF, GK-136901, ML171, VAS2870, and VAS3947.

4. The method according to claim 1, wherein the oxidation inhibitor is selected from the group consisting of ascorbic acid, edaravone, α-tocopherol, glutathione, catechin, and resveratrol.

5. The method according to claim 1, wherein the ADAM inhibitor is selected from the group consisting of TAPI-2, Secophenol, GI254023X, Erythrolosamine, TIMP1, TIMP2, TIMP3, and TIMP4.

6. A method for suppressing or improving hair graying in a human subject, comprising administering apocynin to the human subject.

* * * * *